(12) United States Patent
Kelley et al.

(10) Patent No.: US 10,073,079 B2
(45) Date of Patent: Sep. 11, 2018

(54) DEVICE FOR CAPTURE OF PARTICLES IN A FLOW

(71) Applicant: The Governing Council of the University of Toronto, Toronto (CA)

(72) Inventors: Shana Olwyn Kelley, Toronto (CA); Edward Hartley Sargent, Toronto (CA); Mohamad Reza Mohamadi, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 187 days.

(21) Appl. No.: 14/783,494

(22) PCT Filed: Apr. 11, 2014

(86) PCT No.: PCT/CA2014/050371
§ 371 (c)(1),
(2) Date: Oct. 9, 2015

(87) PCT Pub. No.: WO2014/166000
PCT Pub. Date: Oct. 16, 2014

(65) Prior Publication Data
US 2016/0061811 A1    Mar. 3, 2016

Related U.S. Application Data

(60) Provisional application No. 61/810,905, filed on Apr. 11, 2013, provisional application No. 61/877,524, filed on Sep. 13, 2013.

(51) Int. Cl.
*G01N 33/49* (2006.01)
*B03C 1/01* (2006.01)
(Continued)

(52) U.S. Cl.
CPC ...... *G01N 33/491* (2013.01); *B01L 3/502761* (2013.01); *B03C 1/01* (2013.01);
(Continued)

(58) Field of Classification Search
CPC ........... G01N 33/491; G01N 33/54326; G01N 15/0656; G01N 15/00; G01N 15/0606;
(Continued)

(56) References Cited

U.S. PATENT DOCUMENTS

| | | | |
|---|---|---|---|
| 5,427,663 A * | 6/1995 | Austin | B01J 19/0093 204/450 |
| 2004/0072278 A1* | 4/2004 | Chou | G01N 35/00 435/29 |

(Continued)

OTHER PUBLICATIONS

Tibbe, A. G. et al., "Optical Tracking and Detection of Immunomagnetically Selected and Aligned Cells", Nat. Biotechnol. 17, 1210-3 (1999).
(Continued)

*Primary Examiner* — Melanie Yu Brown
(74) *Attorney, Agent, or Firm* — Ridout & Maybee LLP

(57) ABSTRACT

Devices and methods for capture of target particles in a flow. There is a plurality of flow rate-reducing structures in a flow chamber, each structure including a trapping surface shaped to reduce flow rate in a vicinity of the trapping surface. Reduced flow rate in the vicinity of the trapping surface is non-zero and has a magnitude lower than that of flow rate in other regions of the flow chamber. The reduced flow rate is sufficiently low for an attraction force acting on the target particles to overcome drag force on the target particles, to promote capture of particles in the vicinity of the trapping surface. The device may exhibit different sorting zones for capturing particles that experience different amounts and/or types of attraction force. The device may enable sorting of
(Continued)

cells according to their level of display of specific protein surface markers.

23 Claims, 50 Drawing Sheets

(51) Int. Cl.
| | |
|---|---|
| *B03C 1/033* | (2006.01) |
| *B03C 1/034* | (2006.01) |
| *B03C 1/28* | (2006.01) |
| *B03C 1/30* | (2006.01) |
| *G01N 15/00* | (2006.01) |
| *G01N 15/06* | (2006.01) |
| *B01L 3/00* | (2006.01) |
| *G01N 33/543* | (2006.01) |
| *G01N 33/574* | (2006.01) |
| *G01N 27/00* | (2006.01) |
| *G01N 1/40* | (2006.01) |

(52) U.S. Cl.
CPC ............ *B03C 1/034* (2013.01); *B03C 1/0335* (2013.01); *B03C 1/288* (2013.01); *B03C 1/30* (2013.01); *G01N 15/00* (2013.01); *G01N 15/0606* (2013.01); *G01N 15/0656* (2013.01); *G01N 27/00* (2013.01); *G01N 33/54326* (2013.01); *G01N 33/57434* (2013.01); *B01L 3/502746* (2013.01); *B01L 2200/0668* (2013.01); *B01L 2300/087* (2013.01); *B01L 2300/0816* (2013.01); *B01L 2300/0877* (2013.01); *B01L 2400/043* (2013.01); *B01L 2400/0487* (2013.01); *B01L 2400/086* (2013.01); *B03C 2201/18* (2013.01); *B03C 2201/26* (2013.01); *G01N 1/4077* (2013.01); *G01N 2015/0053* (2013.01); *G01N 2015/0065* (2013.01)

(58) Field of Classification Search
CPC .... G01N 33/57434; G01N 27/00; B03C 1/01; B03C 1/0335; B03C 1/034; B03C 1/288; B03C 1/30; B01L 3/502761
See application file for complete search history.

(56) References Cited

U.S. PATENT DOCUMENTS

| | | | | |
|---|---|---|---|---|
| 2007/0031819 | A1* | 2/2007 | Koschwanez | B01L 3/502707 435/4 |
| 2013/0017538 | A1* | 1/2013 | Ionescu-Zanetti | C12Q 1/6806 435/6.11 |
| 2014/0154703 | A1* | 6/2014 | Skelley | B01L 3/502761 435/7.23 |

OTHER PUBLICATIONS

Galanzha, E. I. et al., "In Vivo Magnetic Enrichment and Multiplex Photoacoustic Detection of Circulating Tumour Cells", Nat. Nanotechnol. 4, 855-60 (2009).
Pantel, K. & Brakenhoff, R. H., "Dissecting the Metastatic Cascade", Nat Rev. Cancer 4, 448-56 (2004).
Steeg, P. S., "Tumor Metastasis: Mechanistic Insights and Clinical Challenges", Nat. Medicine 12, 895-904 (2006).
Pantel, K., Brakenhoff, R. H. & Brandt, B., "Detection, Clinical Relevance and Specific Biological Properties of Disseminating Tumour Cells", Nat Rev. Cancer 8, 329-40 (2008).
Nagrath, S. et al., "Isolation of Rare Circulating Tumour Cells in Cancer Patients by Microchip Technology", Nature 450, 1235-9 (2007).
Adams, A. A et al., "Highly Efficient Circulating Tumor Cell Isolation From Whole Blood and Label-Free Enumeration Using Polymer-Based Microfluidics With an Integrated Conductivity Sensor", J. Am. Chem. Soc. 130, 8633-41 (2008).
Stott, S. L. et al.,"Isolation of Circulating Tumor Cells Using a Microvortex-Generating Herringbone-Chip", Proc. Natl. Acad. Sci., U.S.A. 107, 18392-7 (2010).
Lien, K.-Y.et al. "Rapid Isolation and Detection of Cancer Cells by Utilizing Integrated Microfluidic Systems", Lab on Chip 10, 2875-86 (2010).
Saliba, A.-E. et al., "Microfluidic Sorting and Multimodal Typing of Cancer Cells in Self-Assembled Magnetic Arrays", Proc. Natl. Acad. Sci., U.S.A. 107, 14524-9 (2010).
Wang, S. et al. "Highly Efficient Capture of Circulating Tumor Cells by Using Nanostructured Silicon Substrates with Integrated Chaotic Micromixers", Angew. Chem. Intl Ed. 50, 3084-8 (2011).
Hoshino, K. et al., "Microchip-Based Immunomagnetic Detection of Circulating Tumor Cells", Lab on a Chip 11, 3449-57 (2011).
Kang, J. H. et al., "A Combined Micromagnetic-Microfluidic Device for Rapid Capture and Culture of Rare Circulating Tumor Cells", Lab on a Chip 12, 2175-81 (2012).
Schiro, P. G. et al. 'Sensitive and High-Throughput Isolation of Rare Cells from Peripheral Blood with Ensemble-Decision Aliquot Ranking', Angew. Chem. Intl Ed. 51, 4618-22 (2012).
Gleghorn, J. P. et al. "Capture of Circulating Tumor Cells from Whole Blood of Prostate Cancer Patients Using Geometrically Enhanced Differential Immunocapture (GEDI) and a Prostate-Specific Antibody", Lab on a Chip 10, 27-9 (2010).
Tan, S. J., Yobas, L., Lee, G. Y. H., Ong, C. N. & Lim, C. T. "Microdevice for the Isolation and Enumeration of Cancer Cells from Blood", Biomedical Microdevices 11, 883-92 (2009).
Zheng, S. et al."3D Microfilter Device for Viable Circulating Tumor Cell (CTC) Enrichment from Blood", Biomedical Microdevices 13, 203-13 (2011).
McCloskey, K. E., Chalmers, J. J. & Zborowski, M., "Magnetic Cell Separation: Characterization of Magnetophoretic Mobility", Anal. Chem. 75, 6868-6874 (2003).
Estes, M. D., Ouyang, B., Ho, S. & Ahn, C. H., "Isolation of Prostate Cancer Cell Subpopulations of Functional Interest by Use of an On-Chip Magnetic Bead-Based Cell Separator", J. Micromech. Microeng. 19, 095015 (2009).
Talasaz, A. H. et al., "Isolating Highly Enriched Populations of Circulating Epithelial Cells and Other Rare Cells from Blood Using a Magnetic Sweeper Device", Proc. Natl. Acad. Sci., U.S.A. 106, 3970-5 (2009).
McCloskey, K. E., Chalmers, J. J. & Zborowski, M., "Magnetophoretic Mobilities Correlate to Antibody Binding Capacities", Cytometry 40, 307-15 (2000).
Teste, B. et al., "Magnetic Core Shell Nanoparticles Trapping in a Microdevice Generating High Magnetic Gradient", Lab on a Chip 11, 833-40 (2011).
Baccelli, I. et al., "Identification of a Population of Blood Circulating Tumor Cells from Breast Cancer Patients That Initiates Metastasis in a Xenograft Assay", Nat. Biotechnol. 31, 539-544 (2013).
Zhang, L. et al. "The Identification and Characterization of Breast Cancer CTCs Competent for Brain Metastasis", Sci. Transl. Med. 5, 180ra48 (2013).
Soleymani, L., Fang, Z., Sargent, E H. & Kelley, S. O., "Programming the Detection Limits of Biosensors Through Controlled Nanostructuring", Nature Nanotechnol. 4, 844-8 (2009).
Soleymani, L. et al, "Hierarchical Nanotextured Microelectrodes Overcome the Molecular Transport Barrier to Achieve Rapid, Direct Bacterial Detection", ACS Nano 5, 3360-6 (2011).
Fang, Z. et al., "Direct Profiling of Cancer Biomarkers in Tumor Tissue Using a Multiplexed Nanostructured Microelectrode Integrated Circuit", ACS Nano 3, 3207-3213 (2009).
Vasilyeva, E. et al., "Direct Genetic Analysis of Ten Cancer Cells: Tuning Sensor Structure and Molecular Probe Design for Efficient mRNA Capture", Angew. Chem. Intl Ed. 50, 4137-4141 (2011).

(56) References Cited

OTHER PUBLICATIONS

Lapierre, M. A., O'Keefe, M. M., Taft, B. J. & Kelley, S. O., "Electrocatalytic Detection of Pathogenic DNA Sequences and Antibiotic Resistance Markers", Anal. Chem. 75, 6327-6333 (2003).

Xia, Y. and Whitesides, G. M., "Soft Lithography", Angew. Chem. Intl Ed. 37, 550-575 (1998).

Schneider, C.A., Rasband, W.S., Eliceiri, K.W., "NIH Image to ImageJ: 25 Years of Image Analysis", Nat. Methods 9, 671-675, (2012).

Armstrong, A.J. et al., "Circulating Tumor Cells from Patients with Advanced Prostate and Breast Cancer Display Both Epithelial and Mesenchymal Markers", Mol. Cancer Res. 9, 997-1007 (2011).

\* cited by examiner

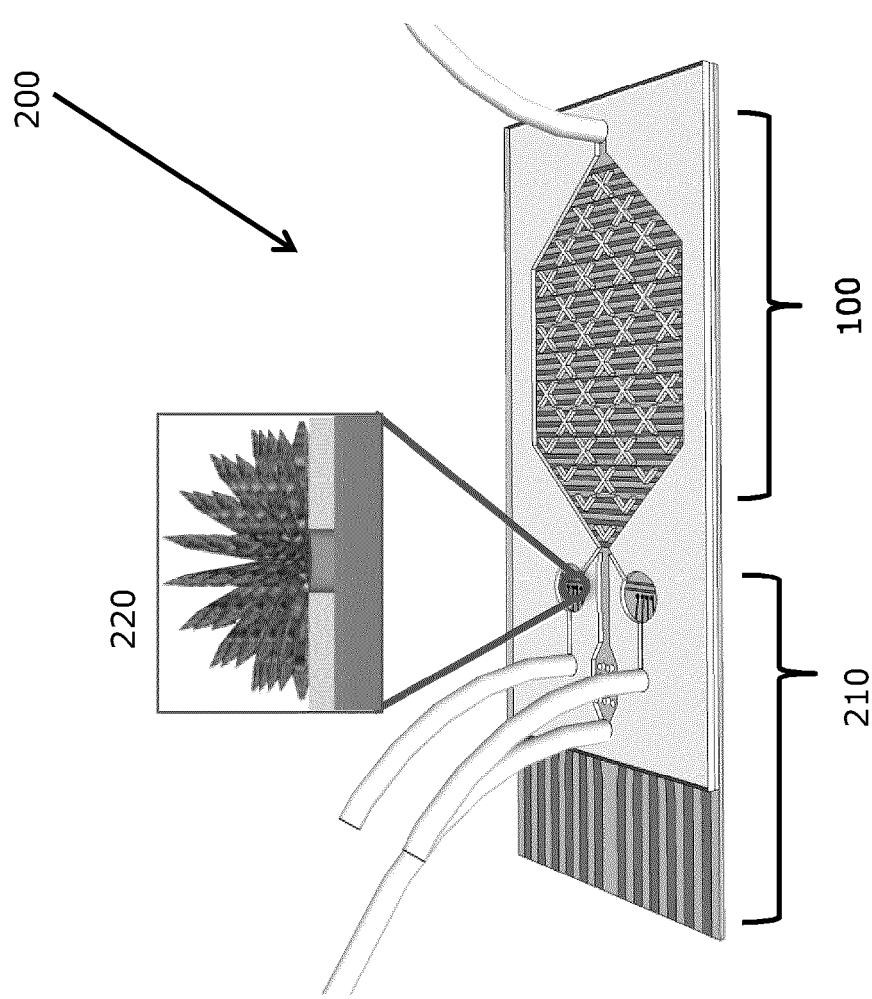

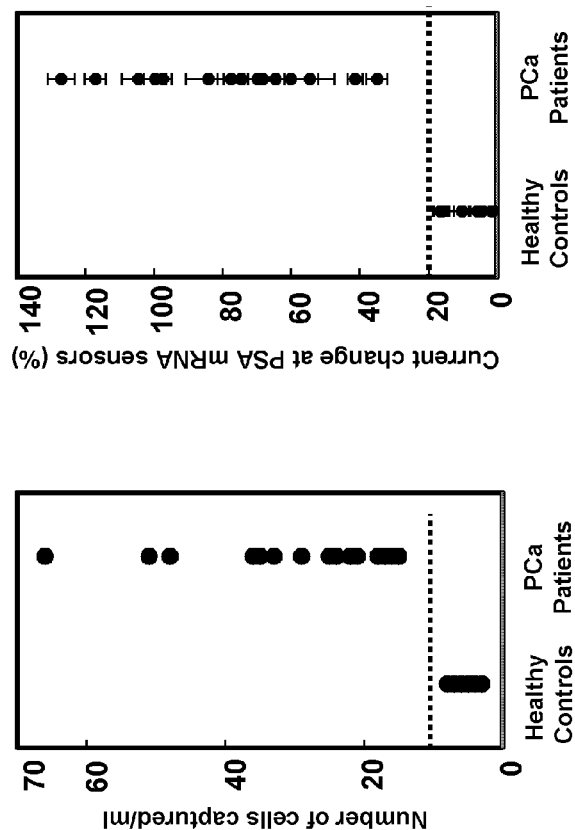
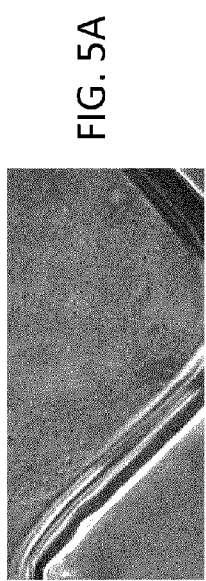
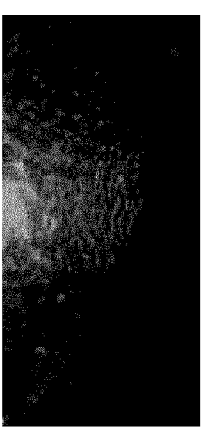
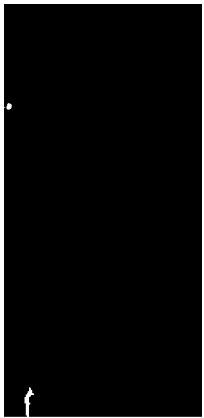
FIG. 5A
FIG. 5B
FIG. 5C
FIG. 5D
FIG. 5E
FIG. 5F
FIG. 5G

DEVICE FOR CAPTURE OF PARTICLES IN A FLOW

CROSS-REFERENCE TO RELATED APPLICATIONS

The present disclosure claims priority from U.S. Provisional Patent Applications Nos. 61/810,905, filed Apr. 11, 2013; and 61/877,524, filed Sep. 13, 2013, the entireties of which are hereby incorporated by reference.

TECHNICAL FIELD

The present disclosure relates generally to devices for capture of particles in a flow. In particular, the present disclosure relates to devices including flow rate-reducing structures in a flow chamber.

BACKGROUND

Rapidly growing solid tumors are known to shed circulating tumor cells (CTCs) that, in turn, then enter the bloodstream[3-4]. CTCs can produce metastatic tumors at sites remote from the primary tumor, and these secondary tumors may be the source of deadly metastatic disease. Early, sensitive detection of CTCs may provide an avenue to early cancer diagnosis[5]. Furthermore, a better understanding of CTCs' genetic makeup may inform the development of advanced treatments against metastatic cancer.

The very low abundance of CTCs in whole blood—where they are outnumbered by blood cells by about a billion to one—makes the isolation and analysis of CTCs challenging. Achieving more efficient, specific capture of CTCs may therefore be desirable in the field of nanobiotechnology.

There has been interest in development of fluidic devices for CTC capture[6-14]. Approaches based on affinity capture[6-8,15], magnetic sorting[9], and size-based separation[16-17] have been reported, often used in conjunction with imaging or off-chip conventional gene expression profiling methods that are used for characterization. However, the very low levels of CTCs present in patient blood samples typically necessitate that several milliliters of whole blood be processed. Thus, it may be desirable to achieve sufficient throughput, as well as sufficient capture yield.

Magnetic nanoparticles (also referred to as nanobeads) have been investigated for targeting CTCs. Magnetic nanobeads can be made specific to CTCs through the attachment of an antibody against a cell-surface marker, for example. Because thousands of nanobeads can attach to a cell[18], this approach may allow specific targeting of CTCs within the large blood samples that may need to be processed for highly sensitive analysis. Magnetic nanobeads, unlike magnetic microbeads[19-21], may offer stability in solution over the time intervals typically needed to process a typical whole blood sample.

Combining magnetic nanobeads with sufficiently efficient and practical fluidic separation has, to date, been unsuccessful, possibly because magnetic nanobeads typically possess a low inherent magnetic susceptibility[18,21-22]. Practical magnetic fields that can be applied in a fluidic device are, when combined with the typical low magnetic susceptibilities of the nanobeads, likely incapable of overcoming the drag forces produced by even slowly flowing liquids. A common method for trapping magnetic microparticles involves placing a permanent magnet or an electromagnet close to the microfluidic channel[13]. However, trapping of sub-100 nm nanobeads typically requires high-gradient magnetic fields that can be difficult to achieve in compact devices.

It has been shown that patient CTCs are relatively heterogeneous, and that it is specific subpopulations with different gene expression profiles that tend to give rise to metastases. Therefore, it would be useful to have more straightforward methods for gene expression-based CTC sorting.[23-24]

SUMMARY

In some example aspects, the present disclosure provides devices for capture of target particles in a flow, in which the device may include: a flow chamber in fluid communication with a flow inlet and a flow outlet; and a plurality of flow rate-reducing structures in the flow chamber, each structure comprising a trapping surface shaped to reduce flow rate in a vicinity of the trapping surface; wherein reduced flow rate in the vicinity of the trapping surface is non-zero and has a magnitude lower than that of flow rate in other regions of the flow chamber; and wherein the reduced flow rate is sufficiently low for an attraction force acting on the target particles to overcome drag force on the target particles, to promote capture of particles in the vicinity of the trapping surface.

In some example aspects, the present disclosure provides methods for capturing target particles in a sample, in which the method may include: introducing the sample containing the target particles to the device described above, the target particles being susceptible to a magnetic attraction force; applying a magnetic field to the flow chamber while flowing the sample through the flow chamber, the magnetic field having a gradient over the flow chamber; removing the magnetic field; and eluting the target particles captured in the flow chamber.

In some example aspects, the present disclosure provides systems for detecting target particles in a sample, in which the system may include the device as described above, which may be referred to as a capture device; and a detection device comprising sensing electrodes; wherein the sensing electrodes generate an electrical signal in response to contact of the target particles with the sensing electrodes.

In some example aspects, the present disclosure provides a device, such as an integrated chip, that provides automated sorting and capturing of target particles (e.g., microparticles, such as cells), where the particles are susceptible to a magnetic attraction force (e.g., coated with different numbers of magnetic nanoparticles). The device may enable sorting of cancer cells according to the cells' level of display of specific protein surface markers. The device may also allow profiling of a patient's heterogeneous sub-population of CTCs in each patient's blood samples, which profiles can in turn be separately analyzed.

BRIEF DESCRIPTION OF THE DRAWINGS

Reference will now be made to the drawings, which illustrate example embodiments of the present disclosure, and in which:

FIG. 4A is a schematic of an example of the disclosed device, used with an example detection chip;

FIGS. 5A-5E show optical and fluorescent images of captured target cells in an example of the disclosed device;

FIG. 5F is a chart showing example counts of target cells captured in an example of the disclosed device;

FIG. 5G is a chart showing example results from electrochemical sensing of target cells in an example of the disclosed device;

It will be noted that throughout the appended drawings, like features are identified by like reference numerals.

DETAILED DESCRIPTION

Magnetic nanobeads may serve as a tool for the labeling of cancer cells for their specific identification[1-2]. Compared with conventional microbeads, nanobeads may have improved colloidal stability, which may be useful for processing larger samples. The nanoscale dimensions of nanobeads may provide the opportunity for thousands (or more) of specificity-enhancing recognition events to occur on the surface of a cell. However, cells that are labeled with magnetic nanobeads may be difficult to capture because their orders-of-magnitude lower magnetic susceptibilities, compared to microbeads, typically result in unacceptably low capture efficiencies or require the use of impractically slow flow rates and/or impractically strong magnetic fields.

In various examples and embodiments, the present disclosure provides example devices for capture of particles in flow. Such devices may be useful for capture of cells, such as for magnetic nanobead-mediated capture of target rare cells (e.g., CTCs). The disclosed devices may include flow rate-reducing structures that give rise to localized regions of lower flow rate, also referred to as flow-velocity valleys. The presence of such low flow velocity regions may enable capture of particles, such as low-magnetic susceptibility labeled cells.

The present disclosure describes the use of example devices for capture of magnetically labeled cells, as an illustrative example. In particular, the capture of CTCs that are labeled with magnetic nanobeads is described as an example. However, the present disclosure may also be suitable for capture of other particles, including non-biological particles (e.g., other magnetically labeled particles or magnetic nanobeads), and/or for capture of particles without the assistance of a magnetic field (e.g., using complementary antibodies, functional groups or other targeting techniques). The present disclosure may also be suitable for capture of particles with the assistance of a magnetic field without the use of magnetic labeling, for example where the particles themselves are magnetic (e.g., the particles themselves are magnetic nanobeads).

Example studies (described further below) found that low-magnetic susceptibility labeled cells may be captured using an example of the disclosed device with near 100% efficiency. These example studies found relatively efficient capture of as few as 3 cells in each milliliter of blood.

In some examples, the disclosed device may be used with chip-based genetic analysis, for example for profiling of the expression of prostate-specific genes in captured cells, such as CTCs captured from whole blood. Example studies described herein show that such profiling may be possible both in model samples and in samples obtained from prostate cancer patients. The present disclosure may provide a sample-to-answer testing approach that may enable genetic confirmation of the presence of target cells, such as CTCs, in a patient sample.

Figures 1A, 1B:
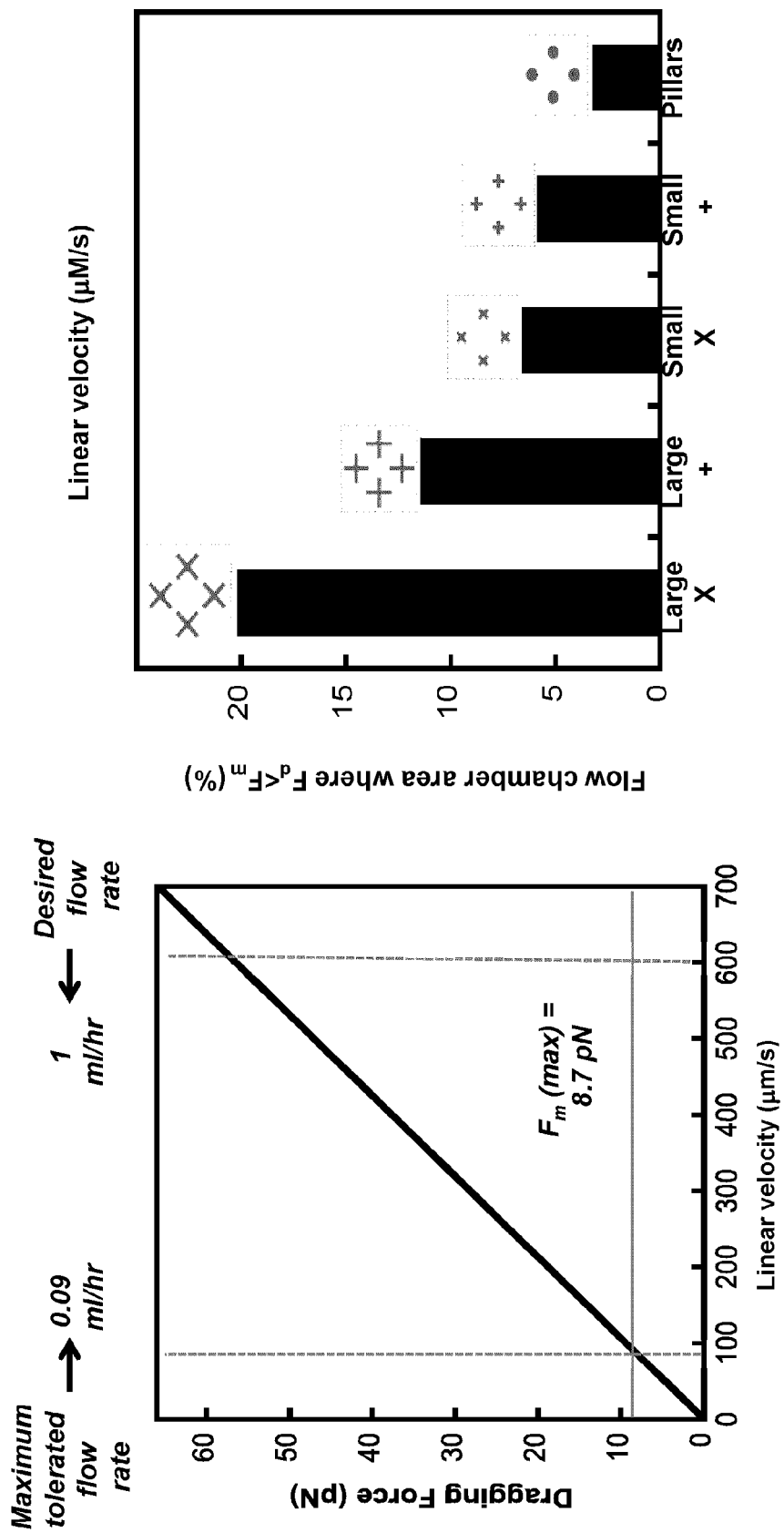
FIG. 1A is a chart showing example simulations illustrating the relationship between drag force and linear flow velocity.
FIG. 1B is a chart showing example simulation results of drag force in various example flow rate-reducing configurations.

To assist in understanding of the present disclosure, the flow rate in conventional flow channels is first considered. FIG. 1A is a chart illustrating the flow vs. capture tradeoff in an example conventional flow channel. A typical maximal magnetic force produced by a typical array of strong magnets (e.g., effecting a magnetic field strength in the range of about 0.5 to about 1 T) acting on a cell labeled with magnetic nanobeads is about 8.7 pN. The magnetic force exerted on the cell may be dependent on a number of factors, for example the size of the magnetic nanobead, the number of nanobeads attached to the cells, the size of the cell and/or the strength of the applied magnetic field. 8.7 pN may be a typical magnitude for the magnetic force exerted on the labeled cell. The present disclosure may be applicable even for magnetic forces that are slightly higher or slightly lower, within practical limits.

The highest flow rate that is compatible with captured cells (that is, where the magnetic force $F_m$ is sufficient to overcome the drag force compelling the cell to flow) was found to be about 0.09 mL/hr (equal to about 100 µm/s average linear velocity in the flow channel), which typically leads to processing long times for 2-to-3 mL samples that may be impractical and may not be advantageous for the survival of fragile cells. Typically a flow rate of about 1 mL/hr (about 600 µm/s) is desirable. If higher flow rates are used to speed up processing, a cell bound by even thousands of magnetic nanobeads may be overwhelmed by the drag force (which is proportional to the cell velocity), and may not be captured but instead be washed out by the flow.

Figure 10:
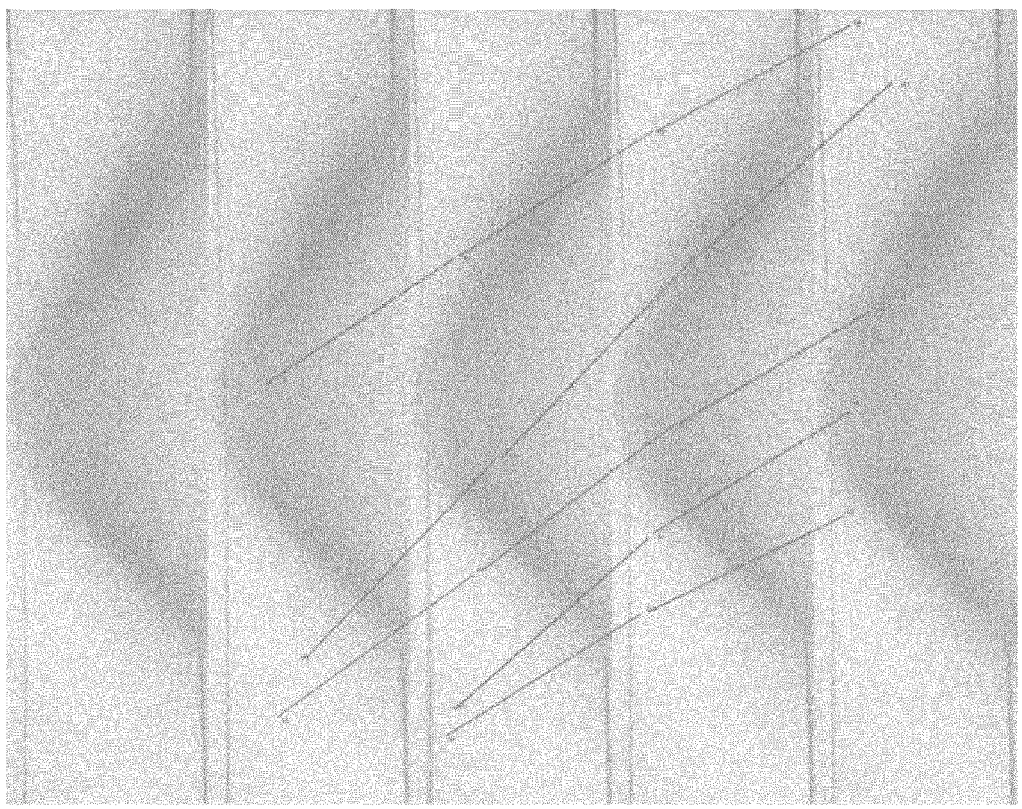
FIG. 10 is a series of images illustrating example flow of magnetically labeled cells in the absence of flow rate-reducing structures.

FIG. 10 is a series of images illustrating how magnetically labeled particles in an example flow (flowing from top to bottom in the images) are attracted to a magnet (located on the right side of the images) but are not captured by the magnet.

The present disclosure provides devices in which a plurality of flow rate-reducing structures is provided in the flow channel (more generally referred to as a flow chamber), in order to help improve capture of particles (e.g., cells labeled with magnetic nanobeads) in the flow. The presence of flow rate-reducing structures may create localized regions of lower flow rate in the flow chamber. The lower flow rate experienced by particles in such regions may allow for capture of the particles (e.g., the reduced flow rate may allow the magnetic force to overcome the drag force on the particles).

Flow rate-reducing structures, which may be microfabricated structures, may be provided in the flow chamber to create flow "velocity valleys" (VVs)—that is, localized regions having lower flow rate, in which particles (e.g., targeted cells) may accumulate. These structures may be designed to avoid trapping of non-target particles. For example, despite being lower in flow rate, the regions of lower flow rate may still have enough flow velocity (that is, the flow rate may be at least non-zero) for non-target particles to be washed from the device, while target particles may be trapped in the low flow rate region. Capture of the target particles may be assisted by an attractant, such as an attracting force (e.g., a magnetic force exerted by an applied magnetic field on magnetically susceptible particles) and/or an attracting functional group.

Once capture of the target particles (e.g., target cells) is complete, the target particles may be eluted for analysis in a small volume by removing the attractant acting on the target particles (e.g., via removal of the magnetic field for example). In some examples, the captured particles may be eluted by applying a strong wash; this may be suitable where the captured particles are unlikely to be sheared or otherwise damaged by a strong wash.

Figure 1C:
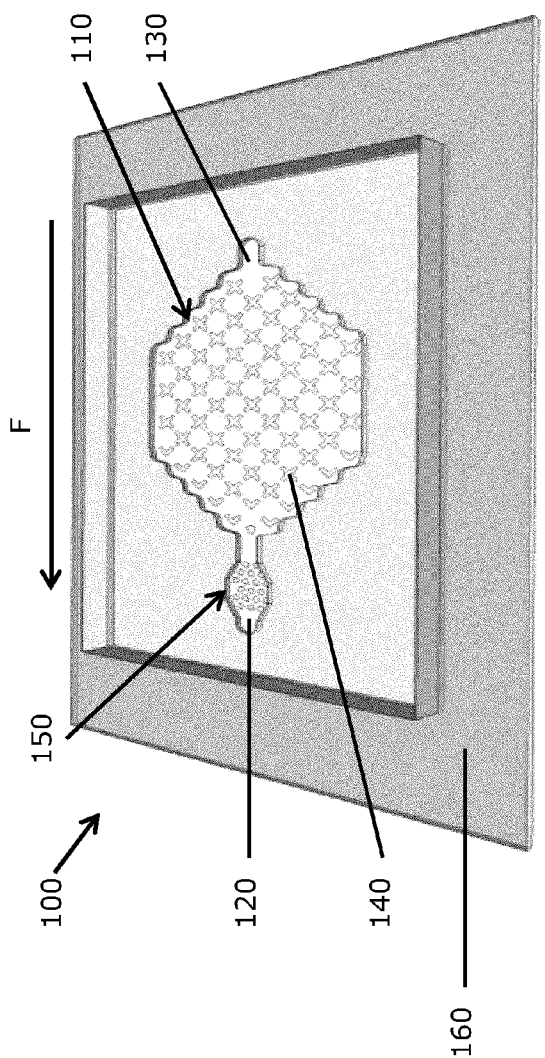
FIGS. 1C-1F show schematics of an example of the disclosed device, and example simulations of flow and magnetic field in the example device.

FIG. 1C shows a schematic of an example device 100 in accordance with the present disclosure. The example device 100 may be in the form of a microfluidic chip. The device 100 may include a flow chamber 110 in fluid communication with a flow inlet 120 for receiving a sample (e.g., a medium carrying target particles as well as non-target particles, for example a blood sample carrying both target CTCs as well as other cells) and a flow outlet 130. There may be a plurality of flow rate-reducing structures 140 in the flow chamber 110. Each flow rate-reducing structure 140 may be configured to generate one or more localized areas of reduced flow rate in portion(s) of its immediate vicinity. In this example, each flow rate-reducing structure 140 includes at least one concave face that is concave facing the direction of flow F, for example in an X-shaped configuration. The design of flow rate-reducing structures 140 and different possible variations are discussed further below.

The flow chamber 110 may also include a filter portion 150, which may serve to filter out certain non-target particles (e.g., debris, skin cells or other clearly non-target particles), for example by including structures that may block larger particles from advancing further into the flow chamber 110. In this example, the device 100 may include a substrate 160 supporting the flow chamber 110, although in other examples a substrate 160 may not be provided.

Figure 1D:
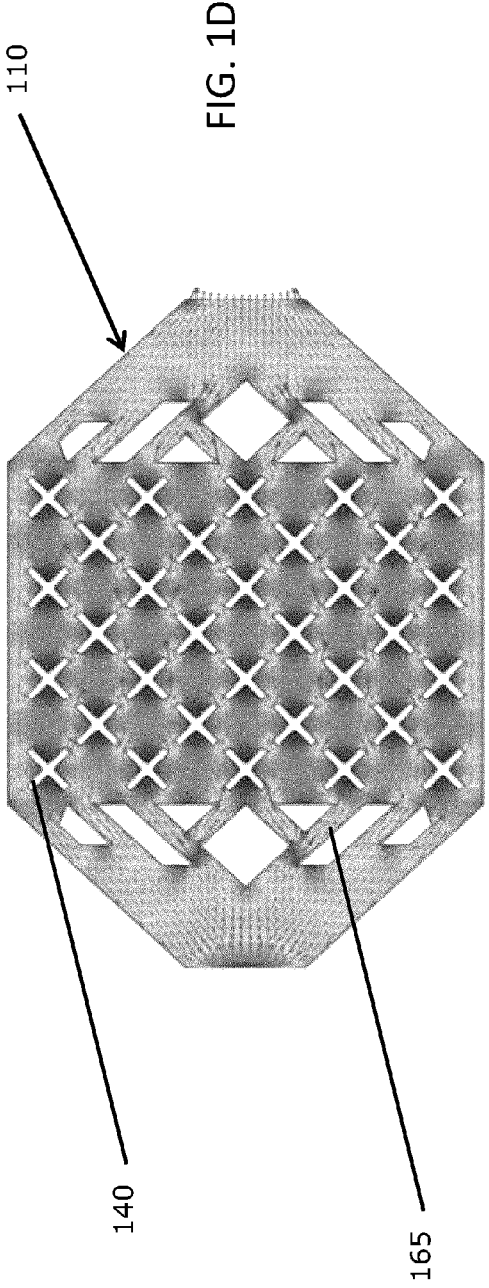

FIG. 1D is a simulation of flow velocity in an example flow chamber 110, where lower flow rates are indicated in the darker areas about the rate-reducing structures 140 and high flow rates are indicated in the lighter areas in the gaps between the arms of adjacent rate-reducing structures 140. The flow chamber 110 of FIG. 1D may be similar to the flow chamber 110 shown in FIG. 1C, however the flow chamber shown in FIG. 1D may not include the filter portion 150, and may include one or more flow-distributing channels 165, which may help to ensure an more even overall flow rate (with the exception of localized low flow rate regions generated by the flow rate-reducing structures 140) through the flow chamber 110.

Figure 1E:
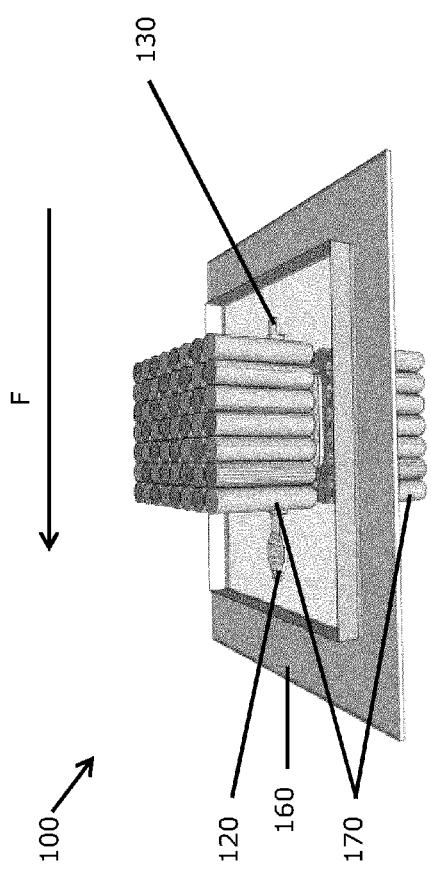

FIG. 1E shows a schematic of the example device 100 of FIG. 1C, including a magnetic arrangement 170 for applying a magnetic field to the flow chamber 110, in order to assist in capture of magnetically labeled target particles. The magnetic arrangement 170 may include magnets positioned near or adjacent to the flow chamber 110. The magnetic arrangement 170 may not be necessary where magnetic labeling is not used.

Figure 1F:
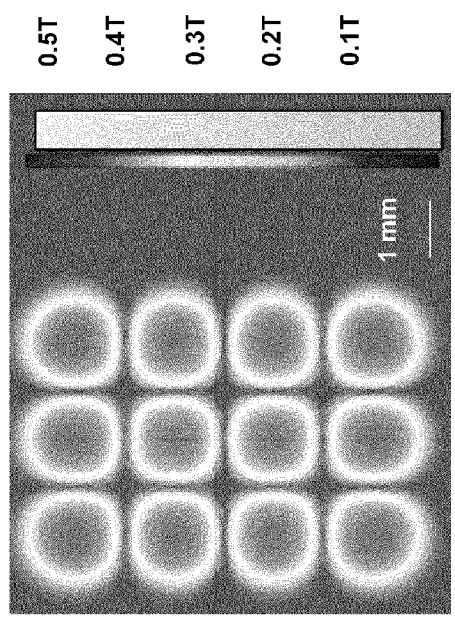

The magnetic arrangement 170 in this example may include magnets positioned in two arrays, with alternating polarities on opposing sides of the flow chamber 110. FIG. 1F shows a simulation of the magnetic field generated in the flow chamber 110, resulting from the magnetic arrangement 170 as shown. The simulation results show that the maximum magnetic strength may be expected to be found near the center of each pair of magnets in the magnetic arrangement 170, and have a maximum strength of about 0.5 T. Other magnetic arrangements 170 may be suitable, as well as other methods for generating a magnetic field (e.g., using external coils). Design of the magnetic arrangement 170 and other suitable variations are described further below.

Figure 1G:
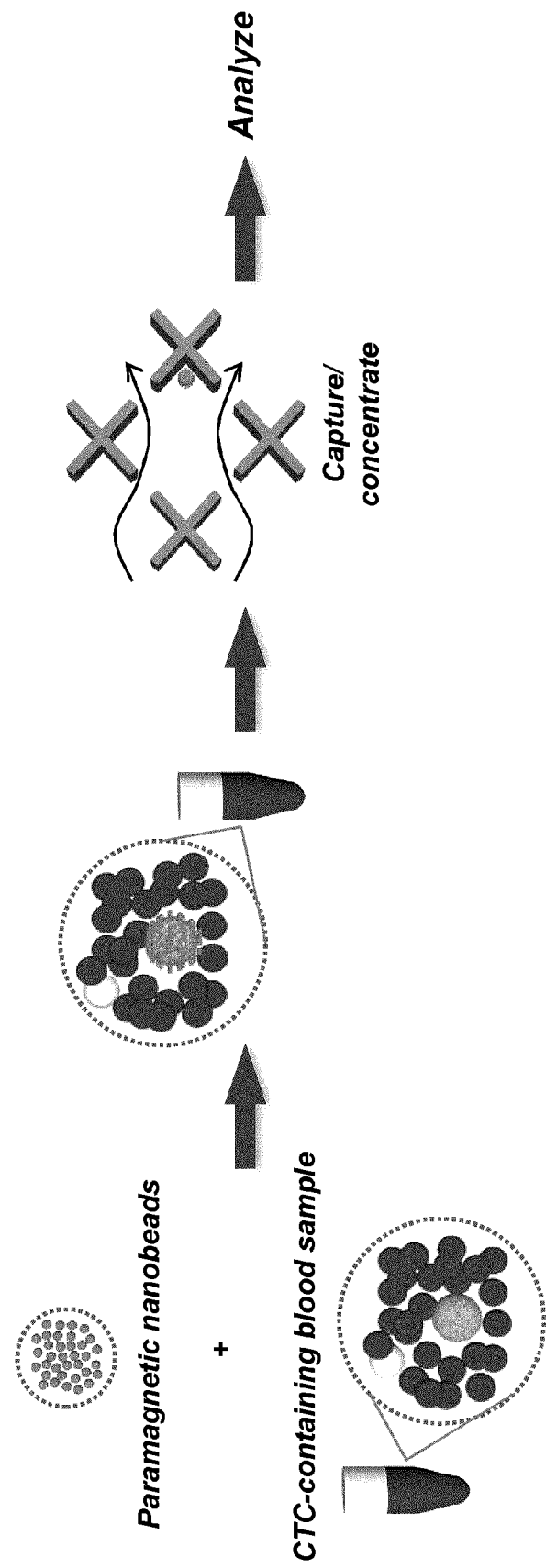
FIG. 1G illustrates an example method for capture of target particles using an example of the disclosed device.

FIG. 1G is a schematic illustrating an example of how target cells (in this case, CTCs) may be labeled with paramagnetic nanobeads and subsequently captured using an example of the disclosed device, such as that shown in FIG. 1C. As shown, paramagnetic nanobeads may be added to patient blood samples and passed through the example device. Labeled CTCs may be captured in the local regions of low flow rate generated by the flow-reducing structures in the flow chamber, while non-target cells (which do not have magnetic labeling) may be washed out. After non-target cells have been washed out, the target cells may be obtained from the device (e.g., by removing the magnetic field and applying a wash) for analysis.

A similar procedure may be used for separating other target particles (e.g., other target cells) using the disclosed device. Magnetic labeling may be used for other target cells, or other methods of attracting target cells over non-target cells may be used (e.g., labeling using complementary antibodies or functional groups). In some examples, such as where the target particles themselves are susceptible to magnetic attraction, labeling of the target particles may not be necessary.

Example Calculations and Simulations

To assist in understanding of the present disclosure, a discussion of drag forces is provided below, as well as a discussion of simulation results. This may provide information for designing suitable configurations for the flow rate-reducing structure and/or for designing a suitable magnetic field (e.g., through design of a suitable magnetic arrangement) to apply to the flow chamber. Such discussion is provided for the purpose of illustration only and is not intended to be limiting. The present disclosure is not bound to or dependent on any theories, equations or simulations discussed.

The drag and magnetic forces experienced by a magnetically susceptible particle are now described. A particle in a flow (e.g., in a flow chamber) may experience a Stokes' drag force ($F_d$):

$$F_d = 6\pi\eta R v$$

where R is the particle radius, $\eta$ is the viscosity of the aqueous medium and v is the velocity of the particle or the linear flow velocity. Linear velocity typically depends on the flow rate and cross sectional width of the flow chamber, which may be dependent on the device size and volume in which captured particles are concentrated.

Where target particles are magnetically labeled, only the target particles may experience the magnetic force ($F_m$) due to the magnetic field applied to the flow chamber, while both target and non-target particles may experience the drag force.

When the magnetic field is applied, $F_m$ acting on a single magnetic nanobead may be modeled as:

$$\vec{F}_m = V_{np} * \frac{\Delta \chi_{np}}{\mu_0}(\vec{B} \cdot \nabla)\vec{B}$$

where $V_{np}$ is the volume of a nanobead, $\chi_{np}$ is its magnetic susceptibility in aqueous solution, $\mu_0$ is the permeability of free space, and B is the magnetic flux density. $F_m$ may thus depend on both the magnitude and gradient of B.

The magnetic force acting on a magnetically labeled particle may be approximated by multiplying the magnetic force on an individual magnetic nanobead by the number of nanobeads per target particle ($N_b$):

$$\vec{F}_m = N_b * V_{np} * \frac{\Delta \chi_{np}}{\mu_0}(\vec{B} \cdot \nabla)\vec{B}$$

These modeling equations may be applied to examples of the disclosed device, in particular the example of FIG. 1C for capturing magnetically labeled CTCs from a blood sample.

In the example of FIG. 1C, the flow chamber 110 may have a total volume of about 5 μL. In capturing CTCs from a blood sample, typically more than 2 mL of the sample should be processed by the device 100. In order to process such a large volume in an acceptable time frame, typically flow rates of 1 mL/h and higher may be used. This flow rate may be equal to an average velocity v of about 600 μm/s in the flow chamber 110.

In this simulation, the applied magnetic field may be determined from simulation of the example magnet arrangement of FIG. 1E (e.g., an arrangement of small magnets each about 1.5 mm diameter and about 8 mm long, with alternate polarity). Simulation of magnetic flux density showed that B may change from about 0 to about 0.5 T repeatedly over about every 0.225 mm² of the flow chamber (see FIG. 1F).

In this simulation, the magnetic nanobeads may be 50 nm MACS magnetic nanobeads. Experimentally determined values for these magnetic nanobeads parameters are given by McCloskey et al.[18]:

$$N_b = \sim 10^4 - 10^6$$

$$V_m \Delta \chi_{np} = 2.5 \times 10^{-16} \text{ mm}^3$$

Assuming $10^5$ beads per target cell, the magnetic force distribution inside the flow chamber may be simulated using COMSOL. The maximum magnetic force exerted on a target cell ($F_{m\_max}$) in the flow chamber was determined to be about 8.7 pN.

If, in the flow chamber, the attracting magnetic force $F_m$ on a target cells is greater than the drag force $F_d$, the target cell is expected to be captured. At high flow rates, even using the highest magnetic fields that are expected to be possible using small magnets, simulation results show that it would not be possible for $F_m$ to overcome $F_d$. This was also observed experimentally in studies showing that stable capture of the target cells could not be achieved.

By introducing flow rate-reducing structures to locally slow down the flow rate in certain regions in the flow chamber, the drag force exerted on a magnetically labeled target cell in those regions would also be reduced, such that the magnetic force would overcome the drag force and the magnetically labeled target cell would be captured in the reduced flow rate region.

Simulations and Comparisons of Different Example Flow Rate-Reducing Structures

The flow rate reducing effects of different structures in the flow chamber of different structures were simulated. Structures that were simulated include X-shaped and +-shaped structures of different sizes. For comparison, the effect of round pillar structures on flow rate was also simulated. As discussed below, simulation results indicate that, of the example structures considered, X-shaped structures exhibited the greatest ability to reduce flow rate, particularly where each structures had a footprint of about 1000 microns over an area of about 1.5 mm×1.5 mm.

The simulations were carried out using COMSOL Multiphysics and Matlab (from Mathworks). All numerical simulations described in the present disclosure were developed using COMSOL. To compare performance of the structures considered, the simulation was used to calculate the percentage area of the flow chamber where $F_d$ is smaller than $F_{m\_max}$, where the magnetically labeled cells would be expected to be captured on or near the flow rate-reducing structures. $F_d$ was calculated for cells suspended in aqueous solution (dynamic viscosity η of 0.001 Pa·s) with an average linear speed v of 600 μm/s (which corresponds to the 1 mL/h flow rate used in the example studies of the present disclosure). In this simulation, the maximum magnetic force $F_{m\_max}$ was expected to be about 8.7 pN, based on typical magnet arrangements.

Figure 11:
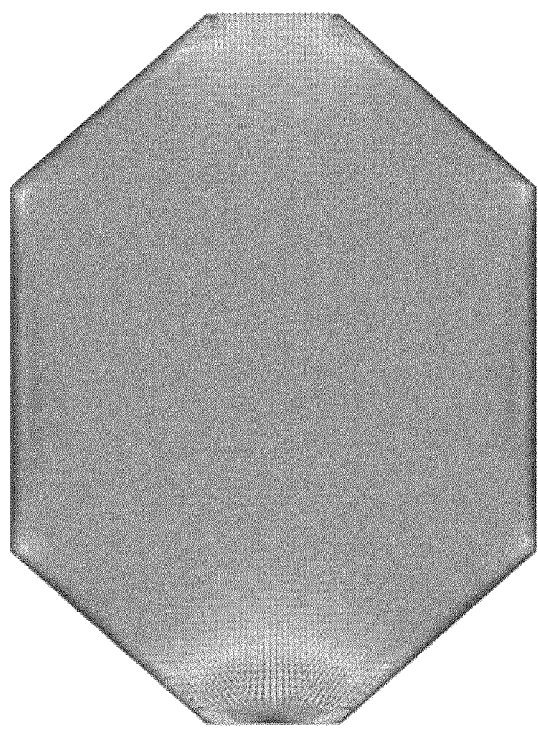
FIGS. 11 and 12 show simulation results of flow rate in example flow chambers, in the absence of flow rate-reducing structures.
Figure 12:
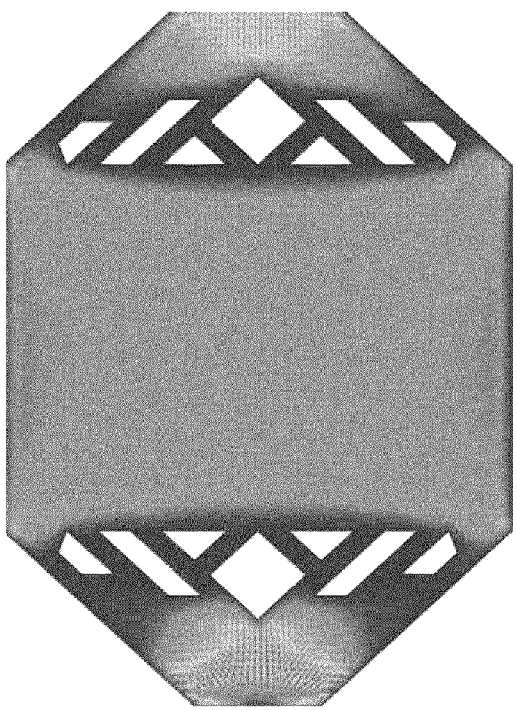

FIGS. 13-18 show flow simulation diagrams for the different structures that were simulated. Example flow velocity profiles (x-axis in μm, y-axis in 0.01*μm/s) are also shown, for flow between adjacent rate-reducing structures, along the indicated lines in each flow simulation diagram. For comparison, FIG. 11 shows a flow simulation diagram for an example flow chamber with no flow rate-reducing structures, and FIG. 12 shows a flow simulation diagram for an example flow chamber with flow-distributing channels but no flow rate-reducing structures. Local linear velocities in the simulations of FIGS. 13-18 were used to calculate the drag forces (using equations as described above). FIG. 1B shows the results of these calculations for various different example simulated structures.

Figure 6A:
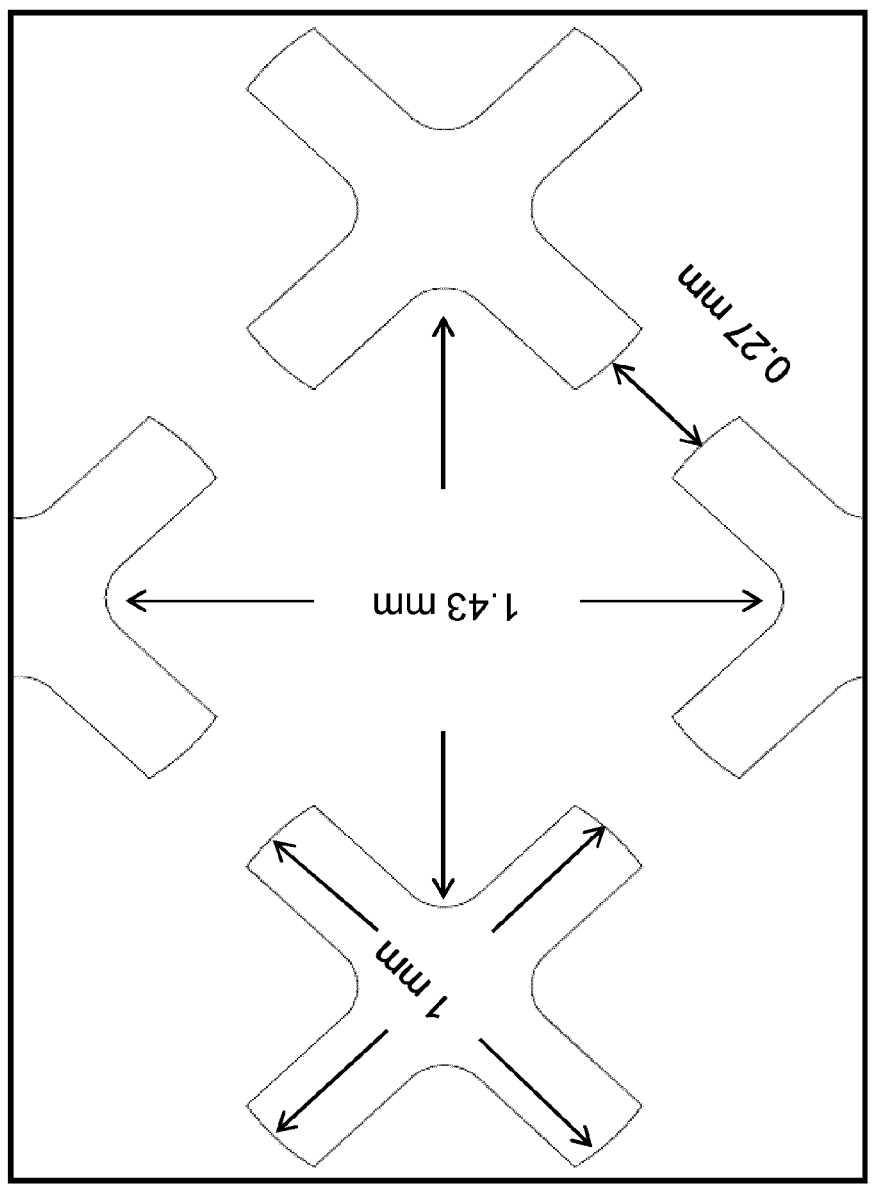
FIG. 6A is a schematic showing example dimensions for an example of the disclosed device.
Figure 14:
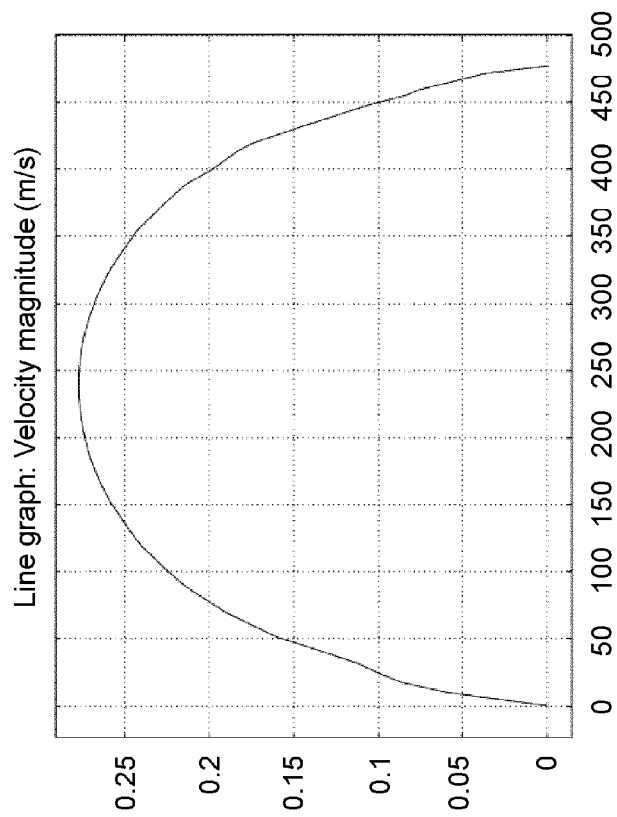
FIGS. 13 and 14 show simulation results of flow rate in an example flow chamber with pillar structures.
Figure 13:
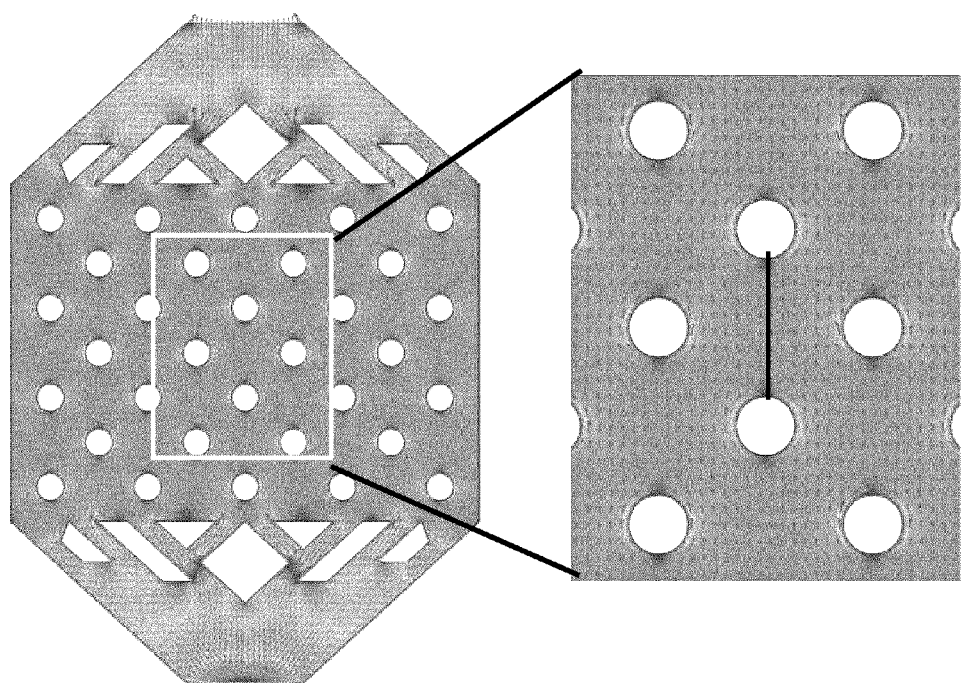
Figure 15A:
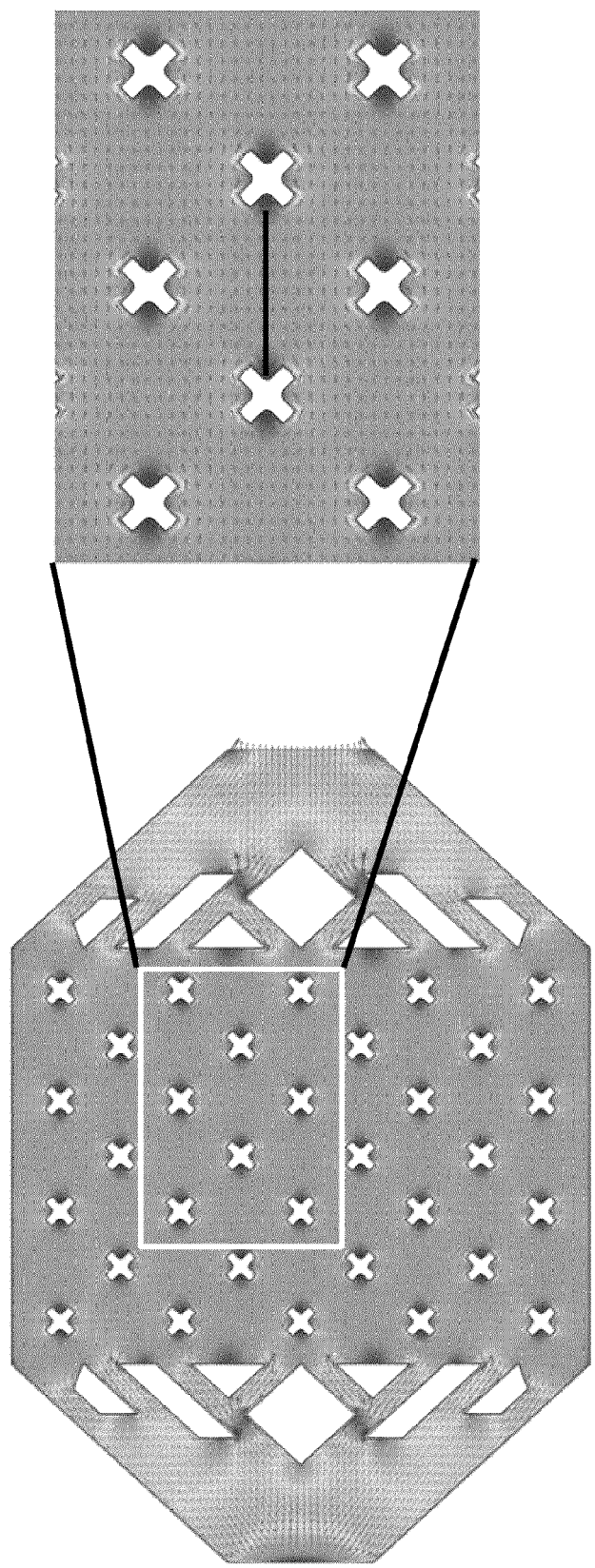
FIGS. 15A-18B show simulation results of flow rate in example flow chambers with different example configurations of flow rate-reducing structures.
Figure 15B:
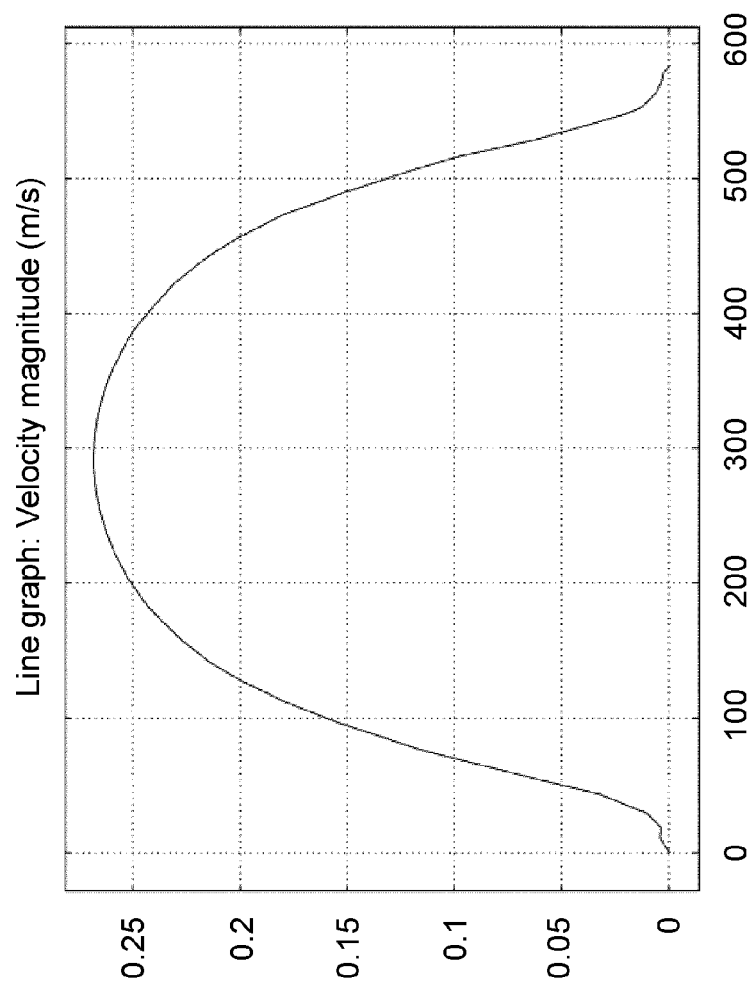
Figure 16A:
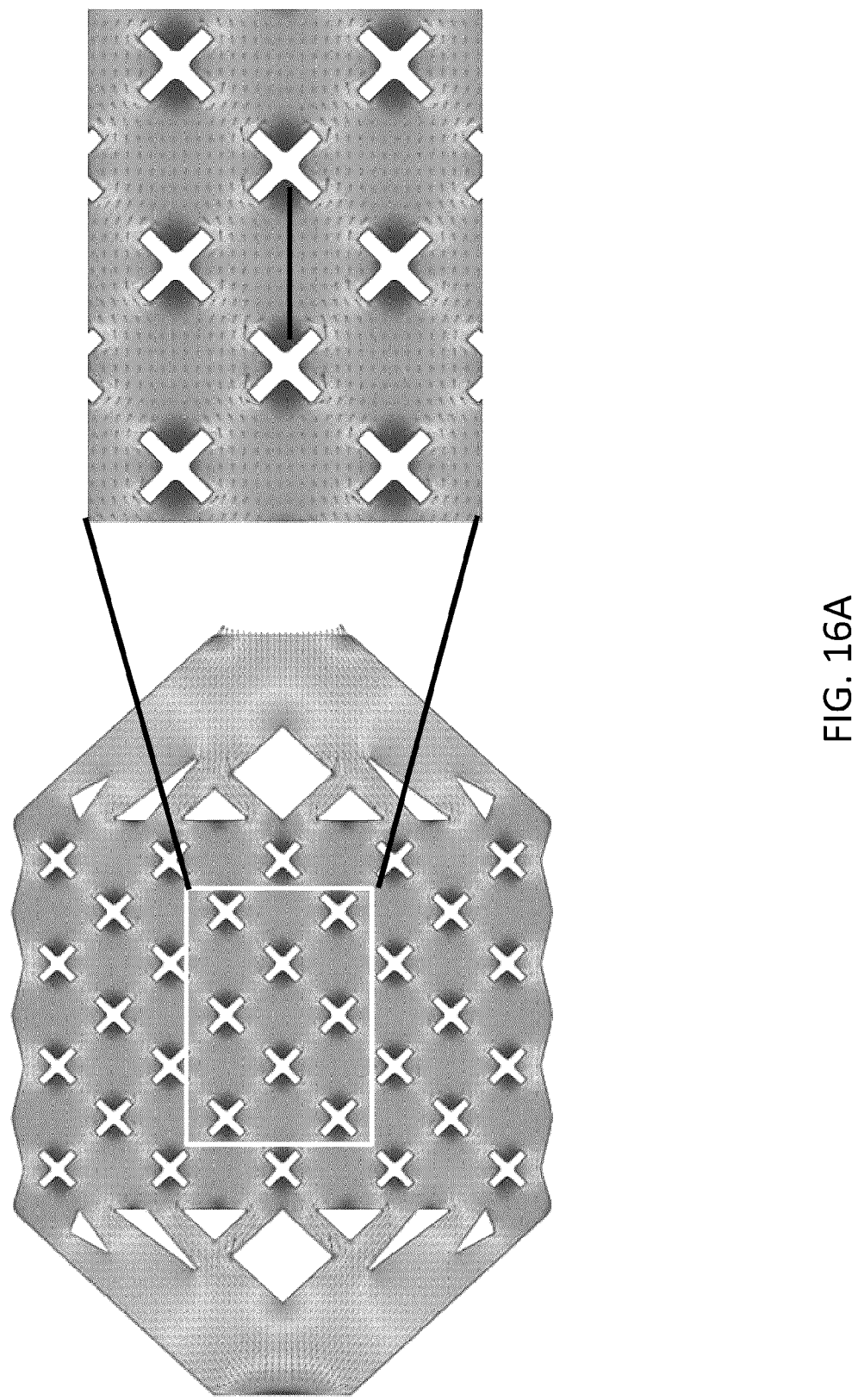
Figure 16B:
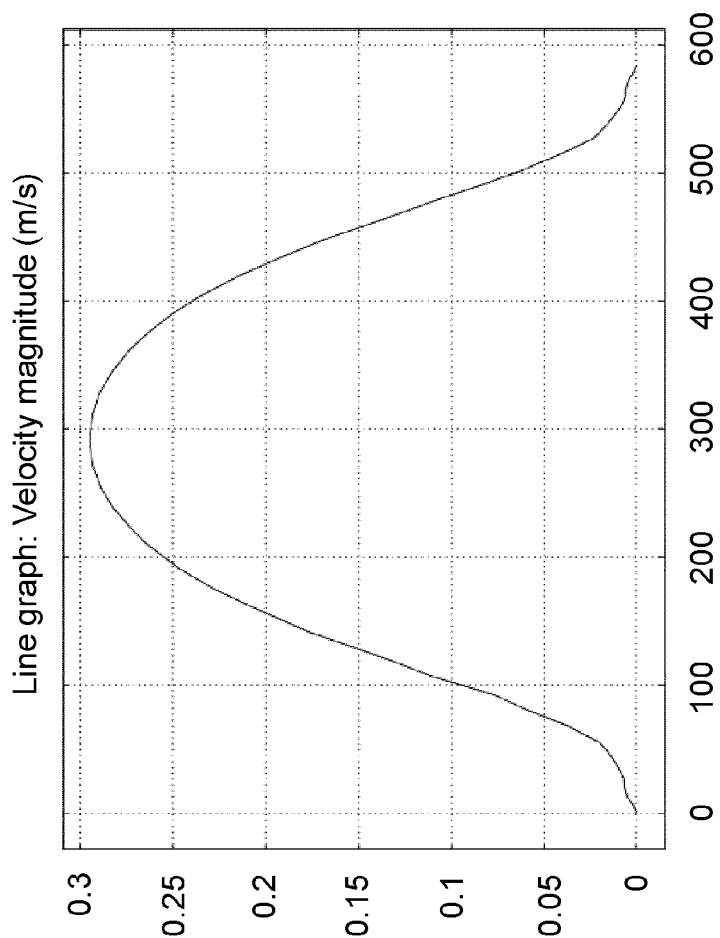
Figure 17A:
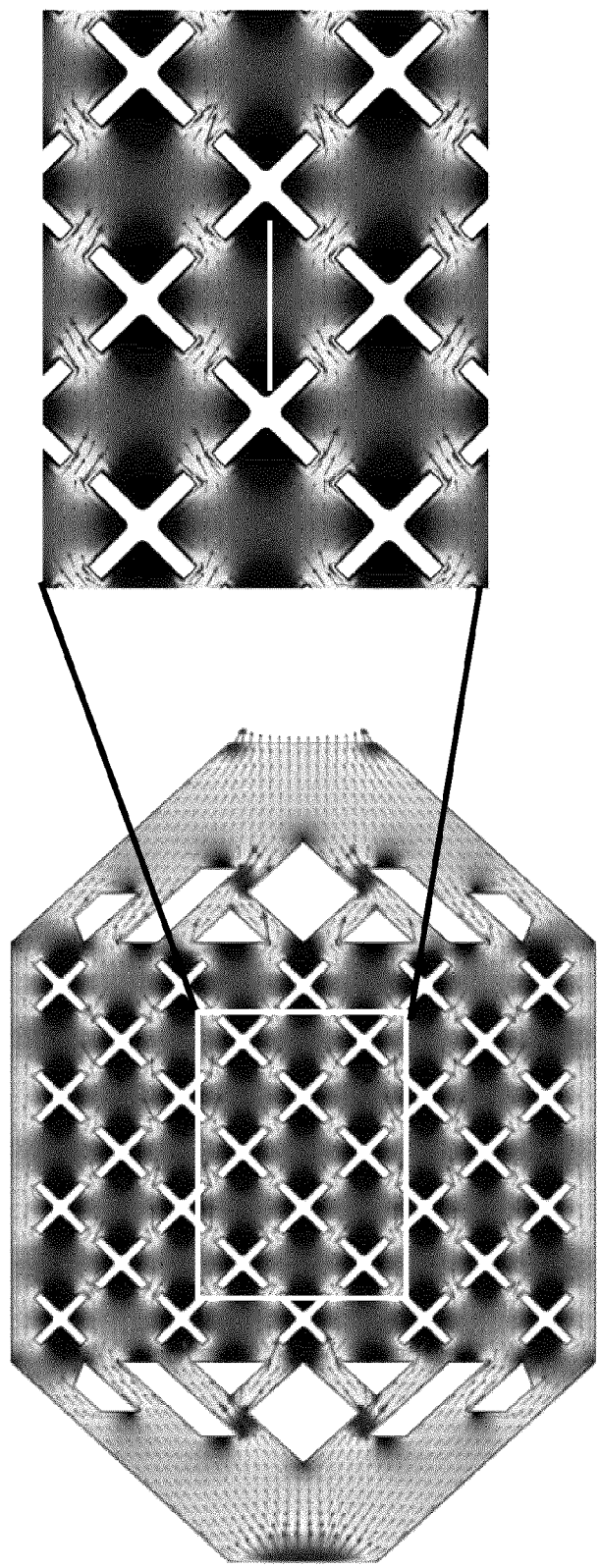
Figure 17B:
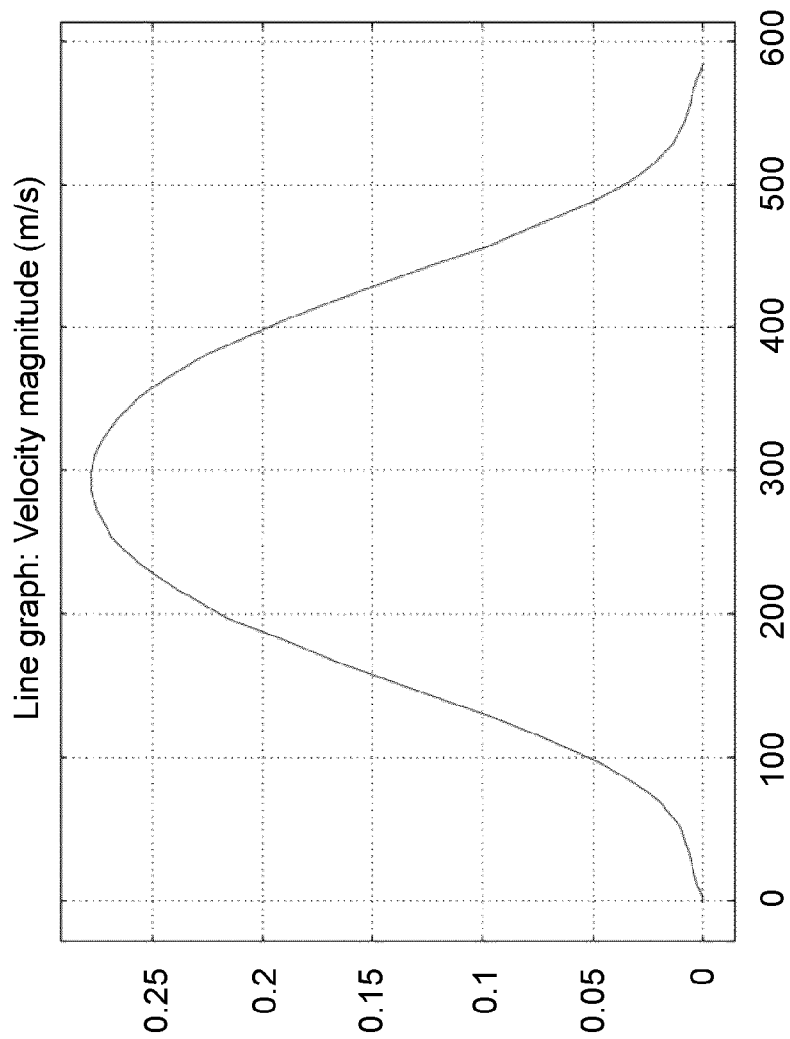
Figure 18A:
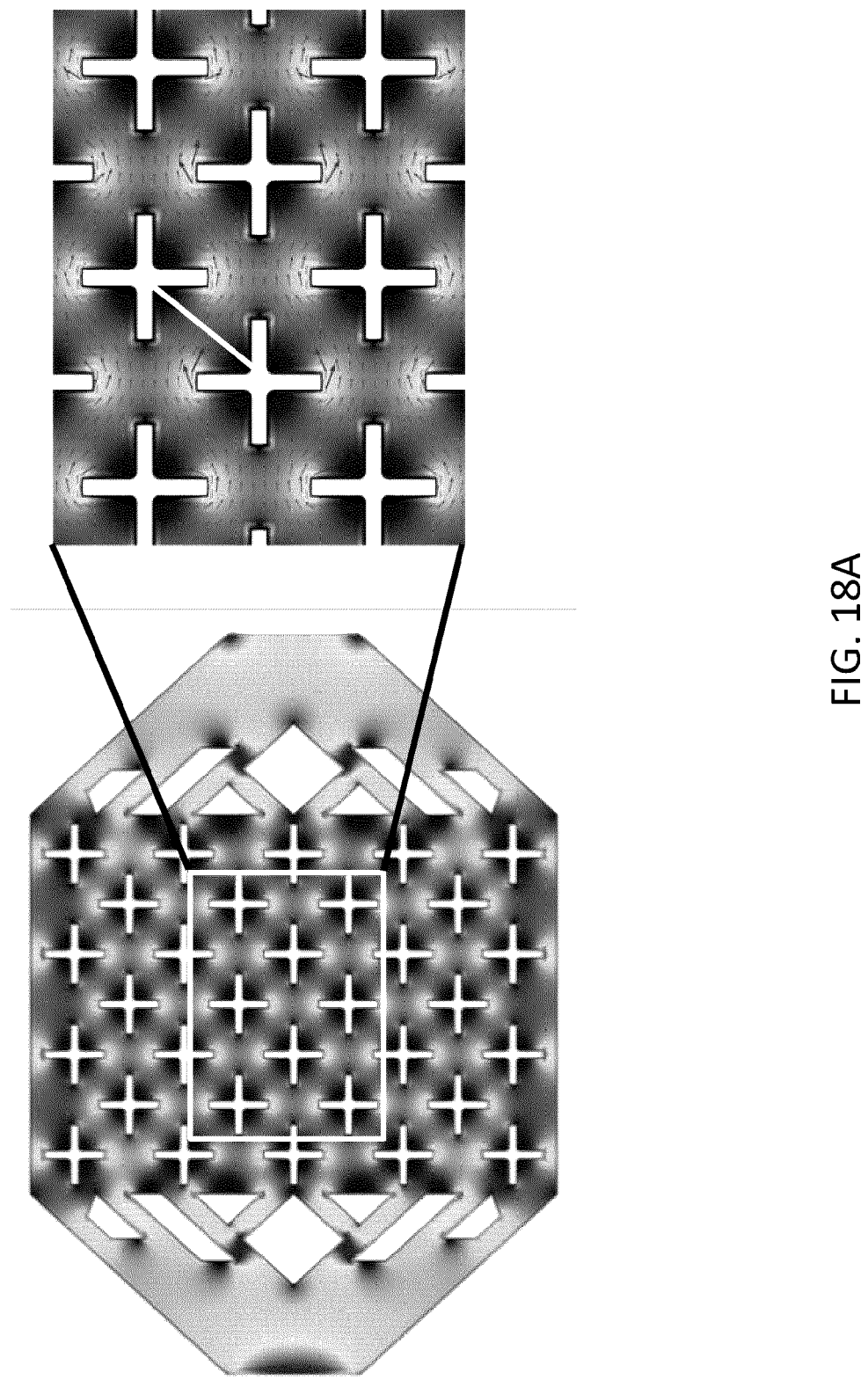
Figure 18B:
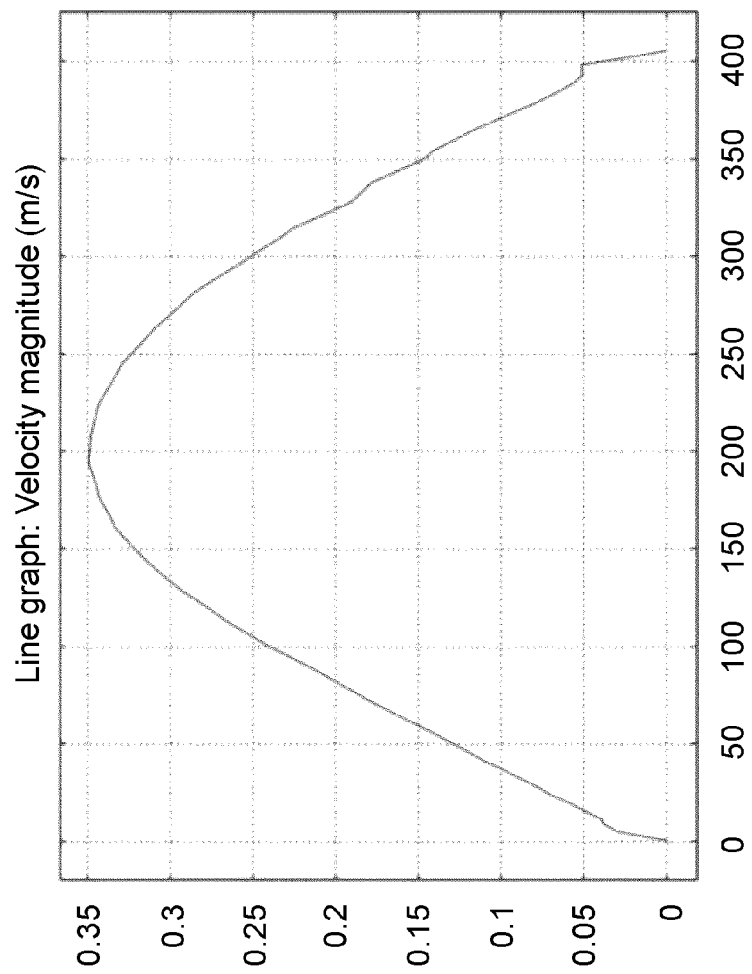

FIGS. 13 and 14 show simulation results for the example pillar structure (structure O). FIGS. 15A and 15B show simulation results for the example small X-shaped structure (structure X0). FIGS. 16A and 16B show simulation results for the example medium X-shaped structure (structure XI). FIGS. 17A and 17B show simulation results for the example large X-shaped structure (structure XII). FIGS. 18A and 18B show simulation results for the example +-shaped structure (structure +II). Example dimensions of the large X-shaped structure are shown in FIG. 6A. The medium X-shaped structure and the small X-shaped structure are ⅔- and ⅓-scale versions, respectively, of the large X-shaped structure. The large +-shaped structure has similar dimensions to the large X-shaped structure, rotated by 45 degrees.

Figure 19:
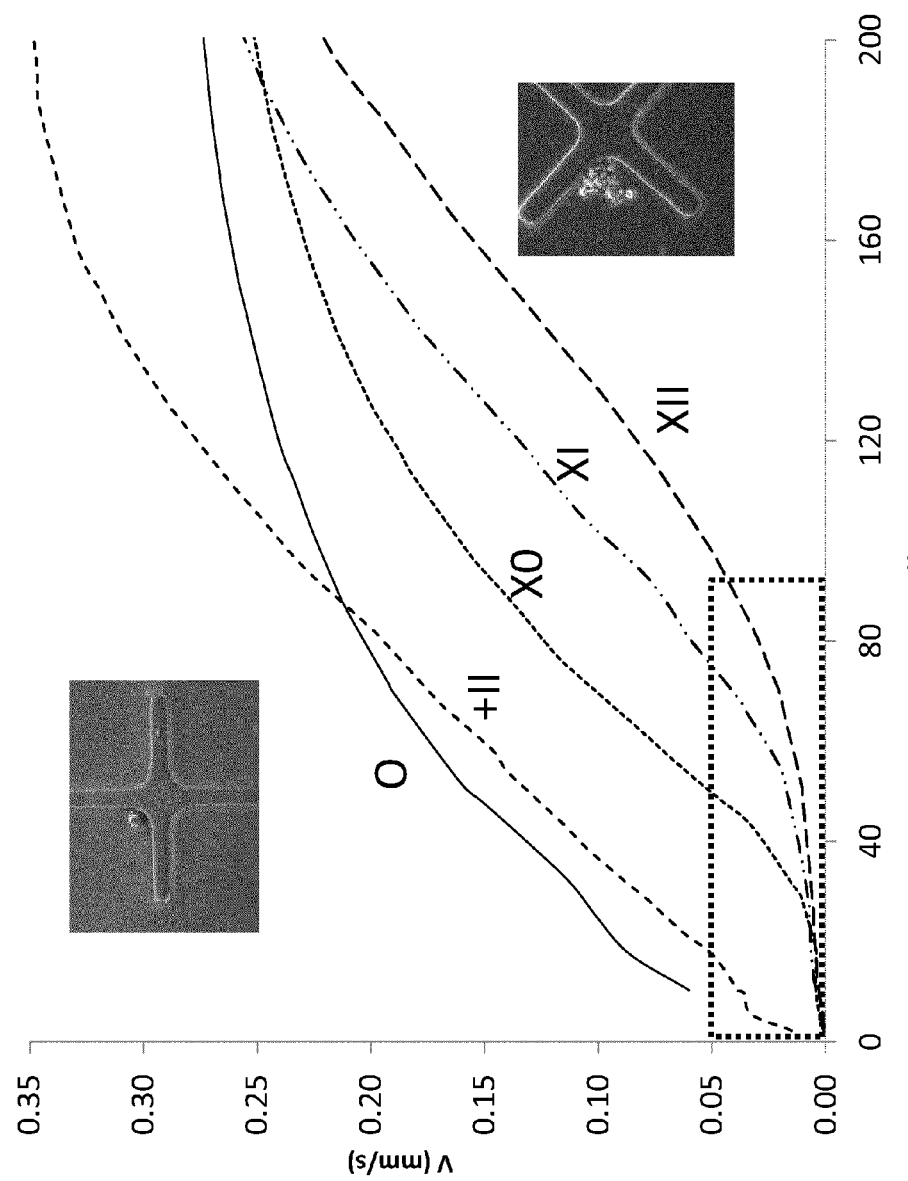
FIG. 19 is a chart comparing simulation results for the flow chambers of FIGS. 13-18B.

FIG. 19 plots the simulated flow rate (V) as a function of distance (x) from the center of the structure considered. The dotted box in FIG. 19 indicates the region in which, based on simulations, magnetic attraction ($F_{m\_max}$) on a magnetically labeled cell is strong enough to overcome drag force ($F_d$) on the cell and thus result in capture of the cell. As shown, the XII configuration (the large X-shaped structure shown in FIGS. 17A and 17B) resulted in the largest region in which $F_{m\_max}$ is greater than $F_d$. Although +-shaped structures were found to have lower capture efficiency compared to X-shaped structures, in studies investigating capture of target cells, +-shaped structures were also found to have more single cell capture.

Figure 6B:
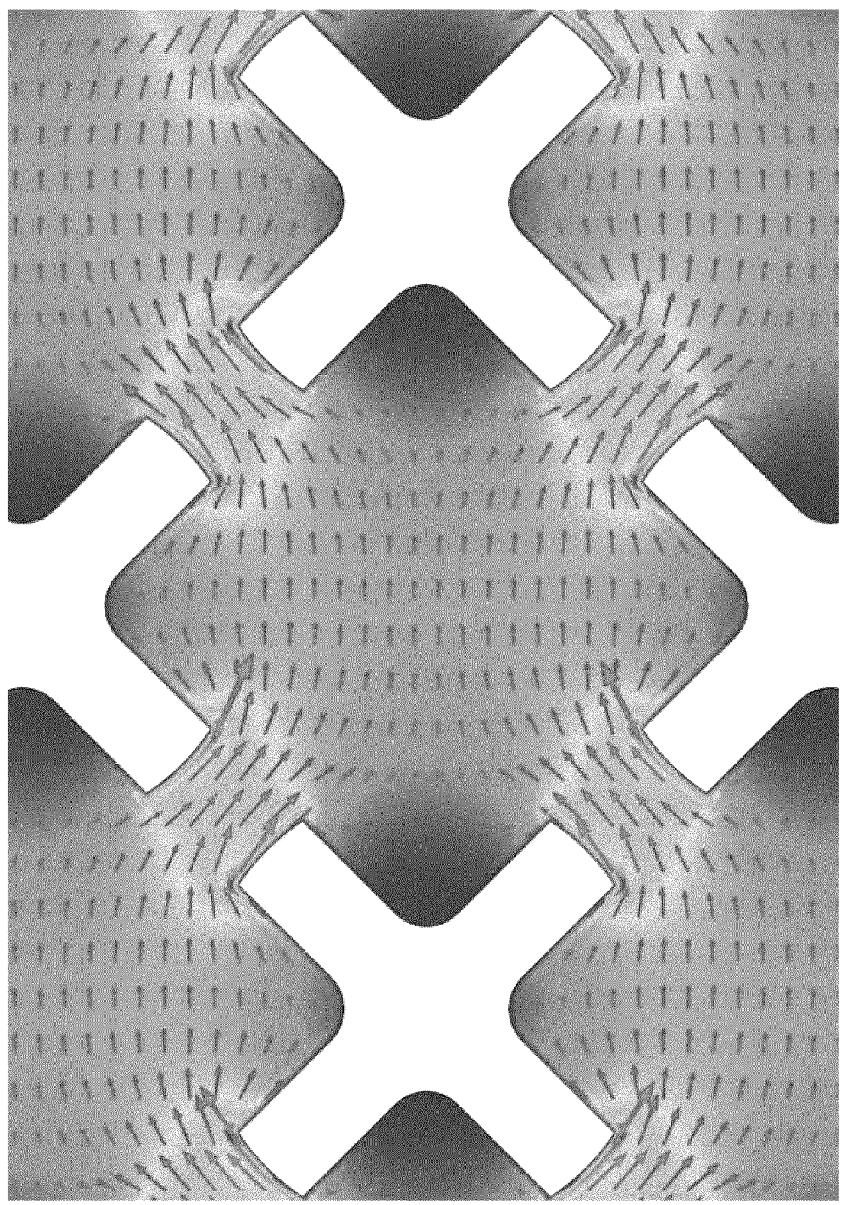
FIG. 6B shows the results of a simulation of flow in an example of the disclosed device.

FIG. 6A is a schematic showing example dimensions of the large X-shaped structures. These dimensions are provided as examples only and may be varied as appropriate (e.g., with the assistance of simulations as described above). For example, the thickness of the arms of the X-shaped structures may be varied depending on the size and/or amount of particles in the sample. FIG. 6B is a flow diagram illustrating simulated flow in the vicinity of the large X-shaped structures, where darker regions indicates regions of low flow rate.

The simulation results (see also FIG. 1B) indicated that microscale flow rate-reducing X-shaped features, in particular X-shaped structures where the each of the structures had a footprint of about 1000 microns over an area of about 1.5 mm×1.5 mm, would decrease $F_d$ below the expected $F_{m\_max}$ (in this case, about 9 pN) over about 20% of the surface area of the flow chamber. This may be expected to produce a sufficient region in which a magnetically labeled particle could be captured, and consistently retained. A relatively compact device (e.g., a few mm long) including such flow-reducing structures may offer a sufficient number of capture opportunities to produce a relatively efficient overall capture yield.

Discussion of Example Flow Rate-Reducing Structures

Although certain example configurations of flow rate-reducing structures are described herein, other configurations may be suitable. A suitable flow rate-reducing structure may be any structure configured to interrupt flow in the flow chamber and configured to reduce flow rate in a vicinity of the structure. The flow rate-reducing structure may have a trapping surface that is shaped to reduce the local flow rate compared to the general flow rate of the flow chamber, and target particles may be captured at or near the trapping surface. Although flow rate is reduced by the flow rate-reducing structure, the reduced flow rate may still be non-zero. This may help to ensure that non-target particles are not inadvertently trapped in a "dead zone" in the flow chamber and may help to ensure that non-target particles are washed out.

The local flow rate may be reduced by the flow rate-reducing structure by a sufficient amount such that an attracting force (e.g., a magnetic attracting force or an attraction to a complementary functional group or antibody) may be stronger than the drag force acting on the target particle, resulting in the capture of the target particle. The amount of flow rate reduction necessary to achieve this effect may be dependent on the overall flow rate in the flow chamber, the characteristics of the target particles and/or the strength of the attracting force, among other factors. These factors may be simulated (e.g., as described above) in order to determine the amount of flow rate reduction desired. Simulations may also be carried out to assist in designing a suitable flow rate-reducing structure.

For example, the flow rate-reducing structure may include a concave surface for trapping target particles, where the concave surface is concave towards the direction of flow. This may result in an arc-shaped flow rate-reducing structure.

In some examples (such as in the configurations discussed above) the flow rate-reducing structure may have a trapping surface defined by two joined arms (e.g., X-shaped, V-shaped or +-shaped structures). X-shaped or +-shaped structures may be able to capture more target particles than V-shaped structures, since X-shaped or +-shaped structures may provide more trapping surfaces, may generate a greater region of localized low flow rate, and may enable trapping of target particles in more than one direction.

The flow rate-reducing structure may also be designed (e.g., with the assistance of simulations) to ensure that non-target particles may escape from being captured. For example, a non-target particle may not be washed out from a trapping surface that is too deep and this may result in the inadvertent capture of non-target particles. It has been found, in the example simulations described above, that an angle of about 90° between the arms of X-shaped and +-shaped structures enabled the capture of target particles while allowing non-target particles to be washed out.

In general, simulations and routine experimentation, such as those disclosed herein, may be used to design and select a suitable configuration for the flow rate-reducing structure, for different conditions (e.g., different flow medium; different types, sizes and/or shapes of target and non-target cells; different strength of attractive force; or different flow rates; among others). The flow rate-reducing structure may be designed such that, for a given set of conditions, the region where the attractive force (e.g., magnetic force) attracting the target cell is greater than the drag force is increased; while the region where linear flow velocity is zero or near zero (which would result in "dead end" trapping of non-target particles) is decreased.

FIGS. 27A-27C, 28A-28C and 29 illustrate how simulations may be used to assist in design of a suitable configuration for the flow rate-reducing structure. The simulation results shown in these figures were calculated using the simulation parameters discussed above, to simulate capture of CTCs in a blood sample labeled with magnetic nanobeads 50 nm in diameters (and assuming $10^5$ beads per target cell), using an average flow velocity of 600 µm/s, and the attractive force of 8.7 pN acting on the target cells.

Figure 27A:
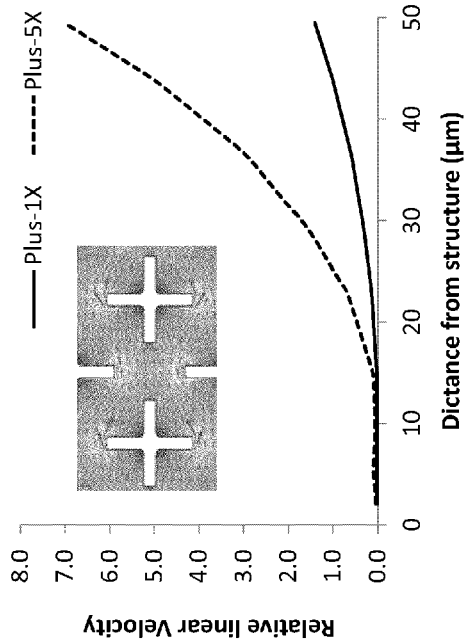
FIGS. 27A-27C, 28A-28C and 29 show charts and simulation results illustrating how a flow rate-reducing structure may be designed.
Figure 27B:
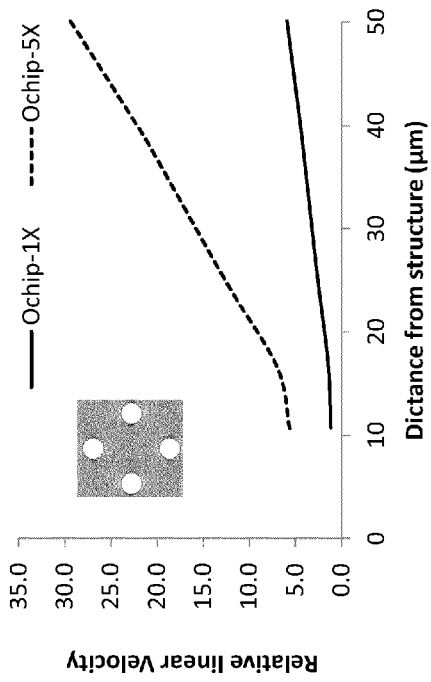
Figure 27C:
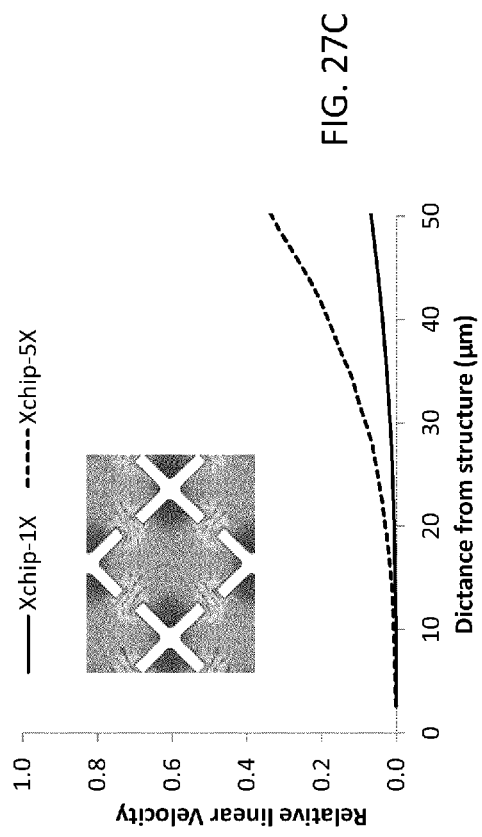

FIGS. 27A and 27B show the simulated velocity profile of the pillar structure ("Ochip") and the +-shaped structure ("Plus"), and the respective simulated flow diagrams (insets), where the overall simulated linear flow rate from inlet to outlet is at 600 µm/s ("1×") and at 3000 µm/s ("5×"). FIG. 27C shows the simulated velocity profile and simulated flow diagram of the large X-shaped structure ("Xchip"), for comparison. As shown, the linear flow velocity close to the X-shaped structure is much lower than that of the pillar structure and the +-shaped structure. Based on such simulation results, it can be expected that using the X-shaped configuration for the flow rate-reducing structure would result in a higher chance of the target particle being captured.

Figure 28A:
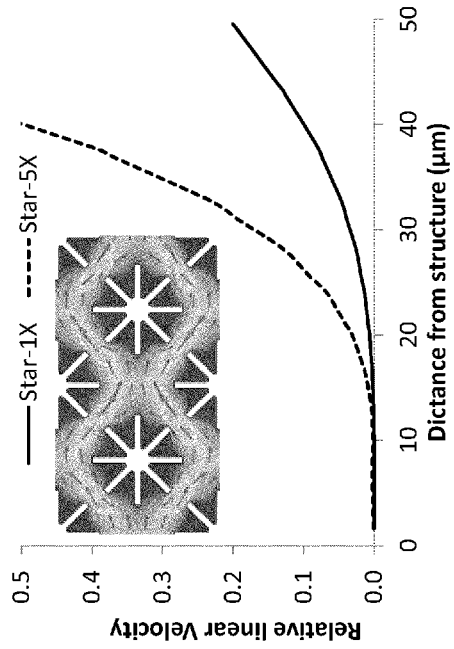
Figure 28B:
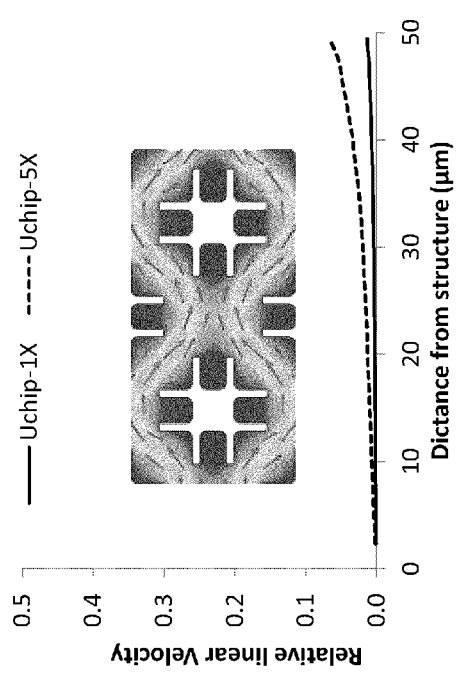
Figure 28C:
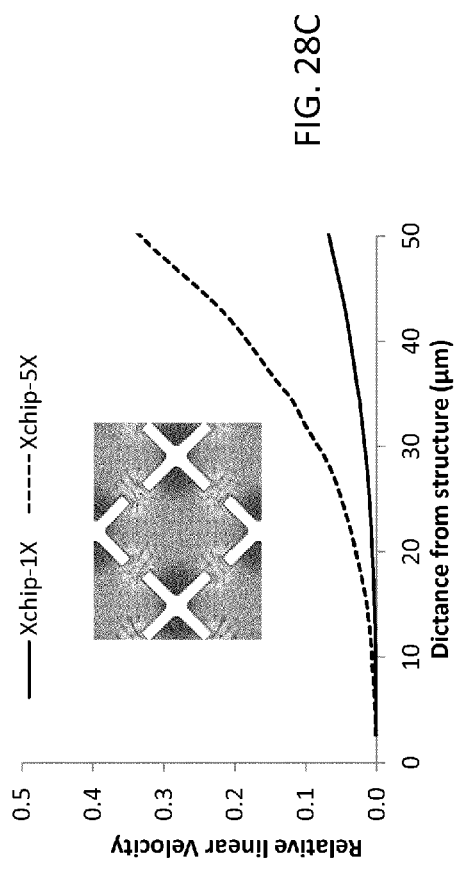

FIGS. 28A and 28B show the simulated velocity profile of a U-shaped structure ("Uchip") and a star-shaped structure ("Star"), and the respective simulated flow diagrams (insets), again where the overall simulated linear flow rate from inlet to outlet is at 600 µm/min ("1×") and at 3000 µm/min ("5×"). FIG. 28C shows the simulated velocity profile and simulated flow diagram of the large X-shaped structure, similar to FIG. 27C but at a different scale. As shown, in the U-shaped structure, the linear flow velocity near the structure is very low, even at an increased flow rate of 3000 µm/min. These simulation results indicate that the U-shaped structure can be expected to be a "dead end" structure that would result in capture of non-target particles, since any particle (whether target or non-target) that enters the low flow rate zone would not be washed out. In the star-shaped structure, the region where flow velocity is low enough for the attractive force to overcome the drag force is smaller than that of the X-shaped structure, meaning it can be expected that the star-shaped structure would have lower capture efficiency of the target particles compared to the X-shaped structure. At the same time, the simulation results for the star-shaped structure show that the linear flow velocity is at or near zero for a distance of about 15 µm from the center of the structure, which gives rise to a "dead end" zone in which non-target particles may be trapped. Thus, simulation results indicate that the U-shaped and star-shaped structures simulated in FIGS. 28A and 28B would not be suitable flow rate-reducing structures, for the particular conditions simulated.

Figure 29:
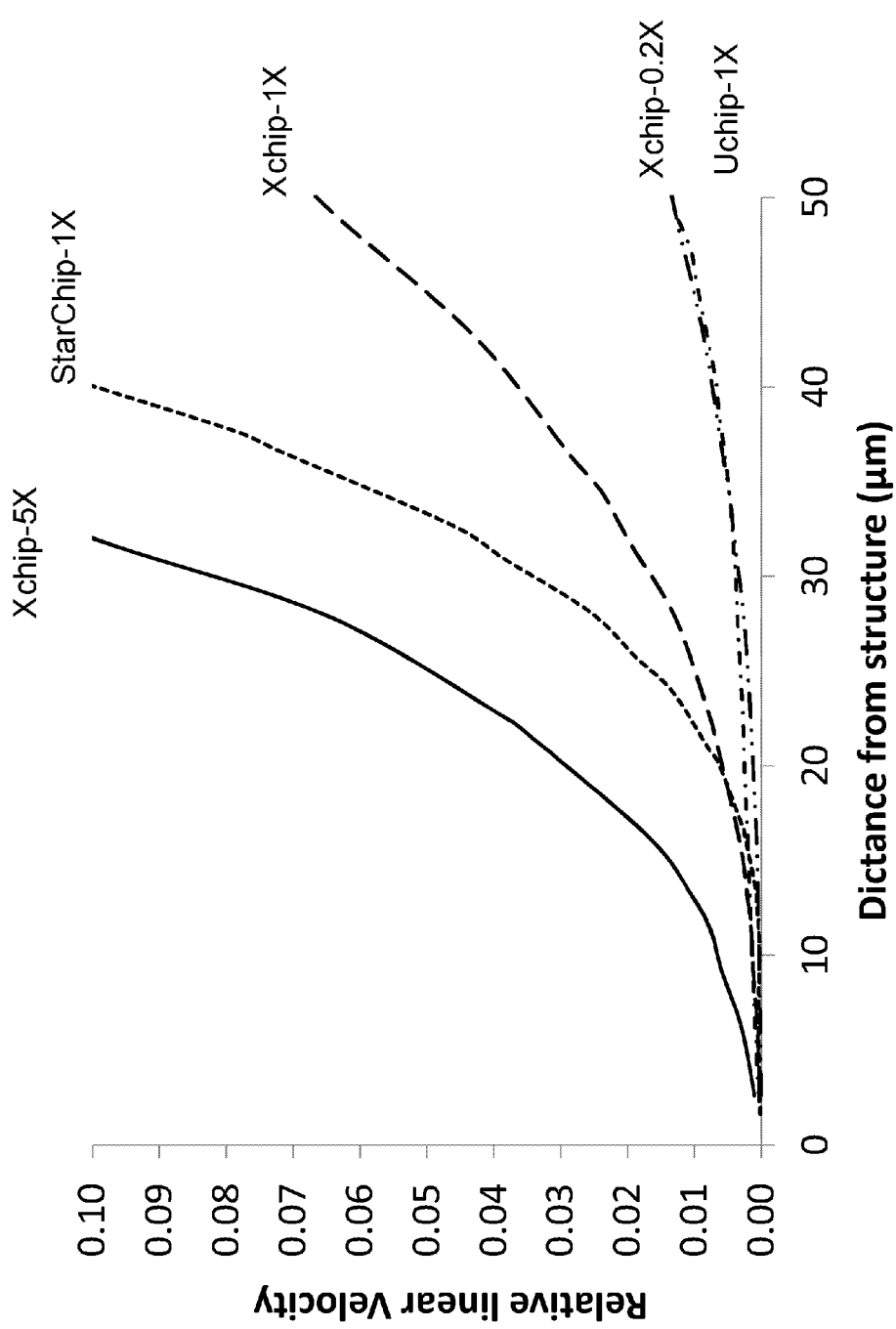

FIG. 29 is a chart comparing the simulated velocity profiles of the U-shaped and star-shaped structures compared to that of the large X-shaped structures, at average inlet to outlet flow rates of 600 µm/s ("1×"), 120 µm/s ("0.2×") and 3000 µm/s ("5×"). The velocity profile of the X-shaped structure at a flow rate of 600 µm/s ("Xchip-1×") was found to result in 100% capture efficiency of the target CTCs while capturing negligible amounts of non-target cells. The velocity profile of the X-shaped structure at a flow rate of 3000 µm/s ("Xchip-5×") was found to result in unacceptably low capture efficiency of the target CTCs, and the velocity profile of the X-shaped structure at a flow rate of 120 µm/s ("Xchip-0.2×") was found to result in unacceptably capture of non-target cells.

By comparing where a simulated velocity profile falls with respect to these known results, it may be determined whether a particular configuration would be suitable for the flow rate-reducing structure. For example, the simulated velocity profiles of the star-shaped structure and the U-shaped structure, at average flow rates of 600 µm/s, stray from the simulated velocity profile of the X-shaped at a flow rate of 600 µm/s ("Xchip-1×") significantly and thus the U-shaped structure and the star-shaped structure are not expected to be suitable configurations for the flow rate-reducing structure. Similar simulations and determination of suitability may be carried out to determine other configurations for the flow rate-reducing structure, in various other conditions.

The flow rate-reducing structures may be positioned in the flow chamber in a regular or irregular array. Using a regular spacing for the array of flow rate-reducing structures and staggering the rows of flow rate-reducing structures may help ensure higher capture efficiency of target particles. Such an arrangement of flow rate-reducing structures may help to ensure that there is little or no possibility that a particle will have a straight-line flow path through the flow chamber from the inlet to the outlet.

Figure 20A:
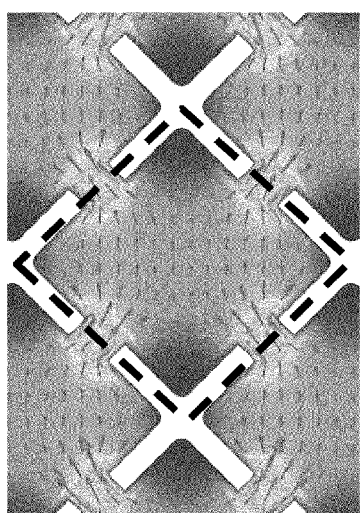
FIGS. 20A-20C illustrates the concept of a capture region in the examples of FIGS. 13, 17A and 18A.
Figure 20B:
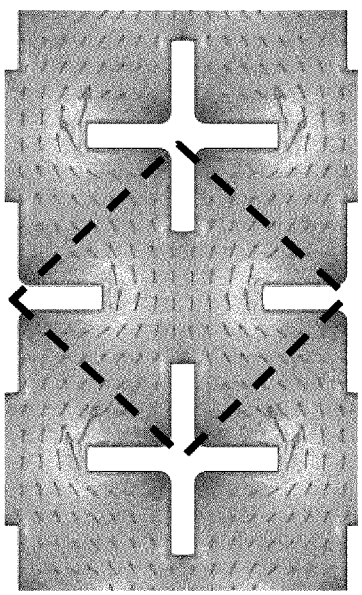
Figure 20C:
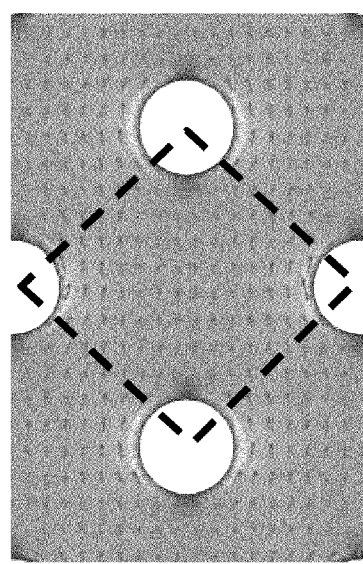

To assist in understanding the present disclosure, it may be useful to picture a capture region as a box area defined by the centers of four flow rate-reducing structures. FIGS. 20A and 20B illustrate such an area (indicated by dashed lines) for X-shaped and +-shaped structures, and associated simulated flow rates. For comparison, FIG. 20C illustrates a similar area for pillar structures. It may be that the more the flow rate is reduced within the box area, the better the capture efficiency. Another way to think about this may be to consider how well the structure traps a particle within the box area. The X-shaped structure, by having arms aligned along the edges of the box shape, may better capture particles in the box area than the +-shaped structure and much better than pillar structures. Although not shown, flow rate-reducing structures may also be configured to be an intermediate between X-shaped and +-shaped structures. That is, while X-shaped structures have arms at about 45° to the direction of flow and +-shaped structures have arms aligned with or at 90° to the direction of flow, other configurations of flow rate-reducing structures may have arms at an angle between 45° and 90° to the direction of flow, for example. This discussion of a box area is provided to assist in understanding only and is not intended to limit the present disclosure. For example, other flow rate-reducing structures may be suitable without defining any such box area.

Example Flow Chamber Designs

Figure 21C:
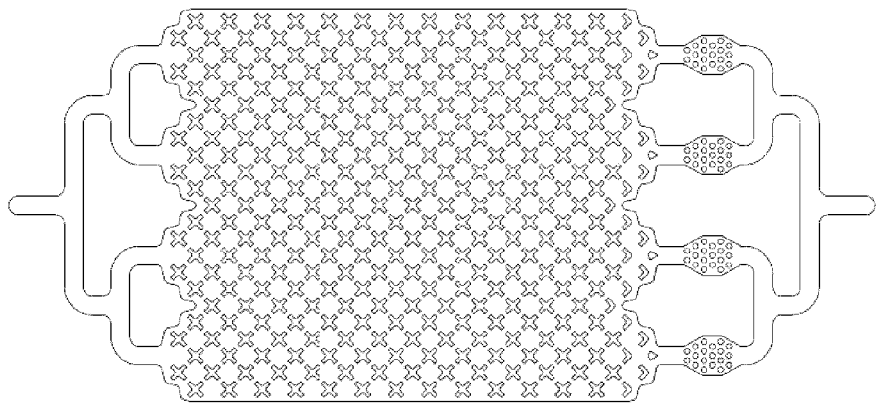
FIGS. 21A-21C are schematics of examples of the disclosed device.
Figure 21B:
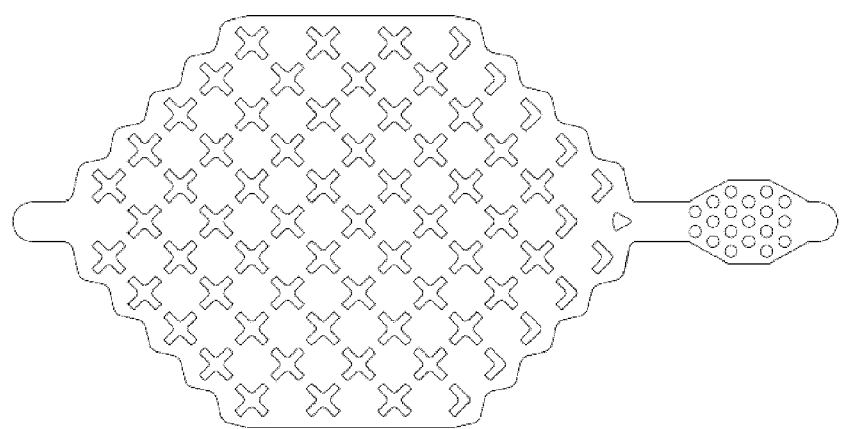
Figure 21A:
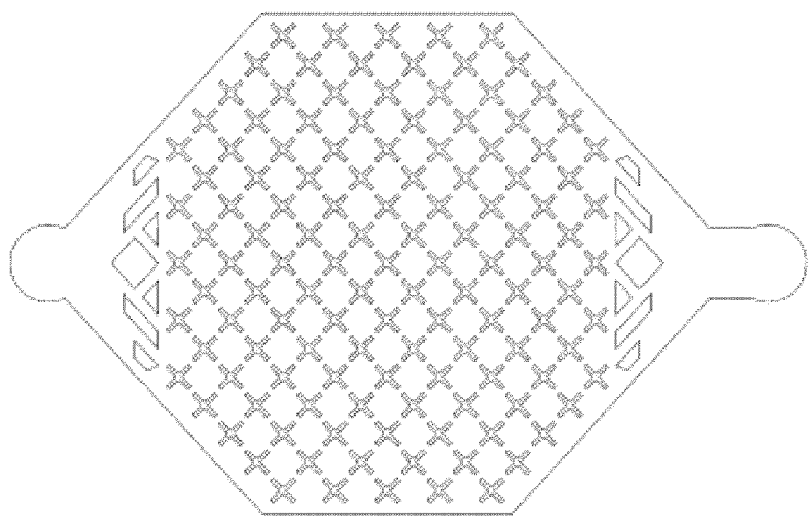

FIGS. 21A-21C show some example designs for the flow chamber, using large X-shaped flow rate-reducing structures. Although these design examples are shown with large X-shaped flow rate-reducing structures arranged in a staggered array, other flow rate-reducing structures having different configurations and/or arrangements may be used. These examples are not intended to be limiting.

FIG. 21A shows an example flow chamber in which the flow chamber includes flow-distributing channels near the flow inlet and flow outlet. In this example, the flow chamber may be about 10.3 mm long from the flow inlet to the flow outlet, and about 6.5 mm wide.

FIG. 21B shows an example flow chamber in which the flow chamber includes a filter portion for filtering out non-target particles. In this example, the flow chamber may be about 20.2 mm long from the flow inlet to the flow outlet, and about 10.4 mm wide.

FIG. 21C shows an example flow chamber including both flow-distributing channels and filter portions. In this example, the flow chamber may be about 46.5 mm long from the flow inlet to the flow outlet, and about 22 mm wide.

Example Magnetic Arrangements

An example magnetic arrangement generating a suitable magnetic field for the disclosed device was described above. It has been found that the magnetic nanobeads experience the strongest magnetic force at a magnetic field gradient. Thus, the example magnetic arrangement may be designed to generate magnetic field gradients over the entire area of the flow chamber. The location of the maximum field gradient generated may be substantially random or uncorrelated with the position of the flow rate-reducing structures. In other examples, the location of the maximum field gradient generated may be co-localized with regions of low flow in the flow chamber. It may be useful to have the magnetic field gradients substantially uncorrelated with regions of low flow, to avoid the possibility of uneven target particle distribution (which may be undesirable for imaging purposes) and/or clogging in the flow chamber. Other magnetic arrangements may be used to generate different magnetic fields.

The effectiveness of such other magnetic arrangements may be determined using simulations and calculations, such as described above, as well as through experimentation. Some other magnetic arrangements that may be considered are described below.

Figure 22:
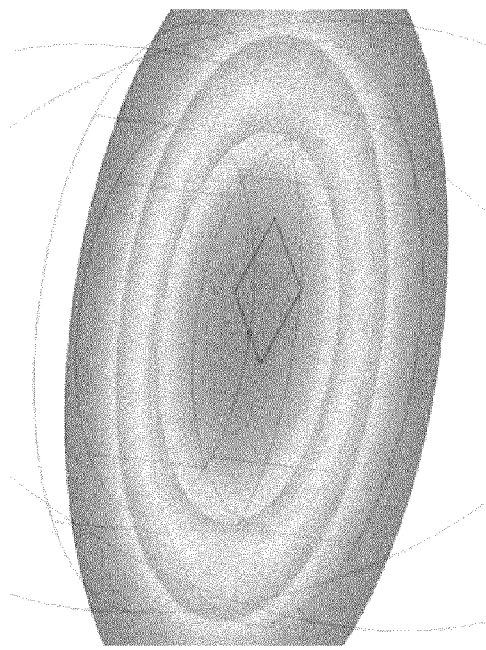
FIGS. 22-25E show simulation results of example magnet arrangements suitable for use with an example of the disclosed device.

FIG. 22 shows the simulated magnetic field generated by a single pair of annular magnets (one magnet above and one magnet below the flow chamber).

Figure 23B:
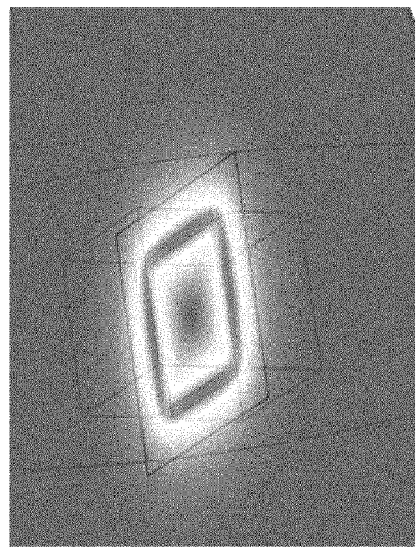
Figure 23A:
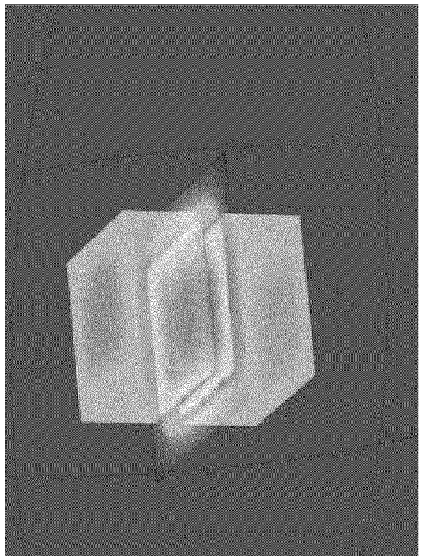

FIG. 23A shows a single pair of square magnets (one magnet above and one magnet below the flow chamber). FIG. 23B shows the resulting simulated magnetic field.

Figure 24A:
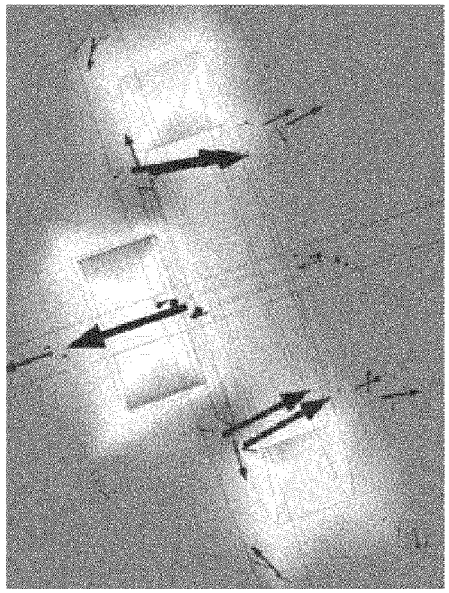
Figure 24B:
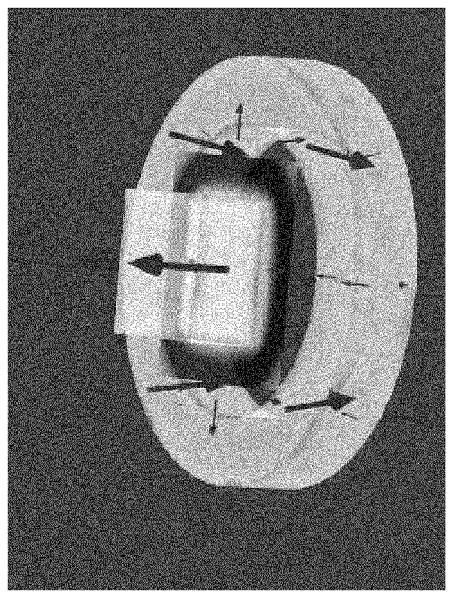
Figure 24C:
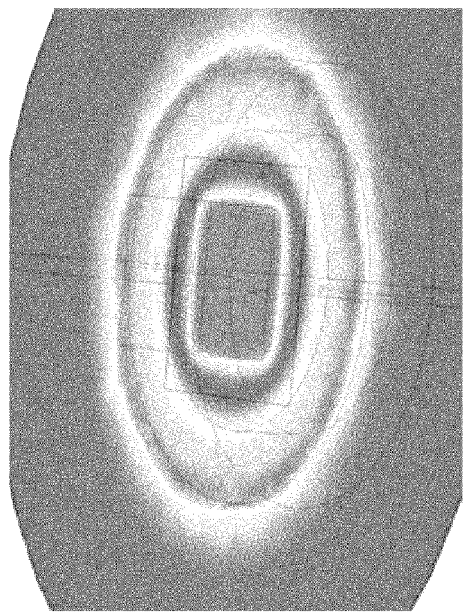

FIG. 24A shows an arrangement combining the arrangements of FIGS. 22 and 23A. FIGS. 24B and 24C show the corresponding simulated magnetic field.

Figure 25A:
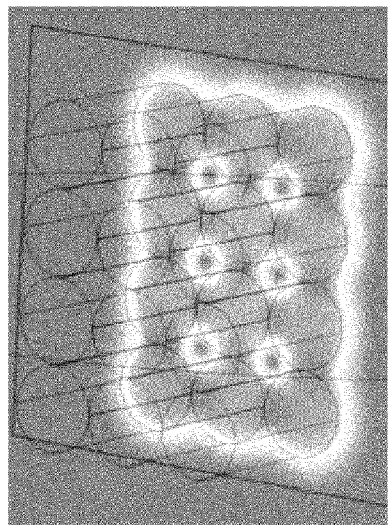
Figure 25B:
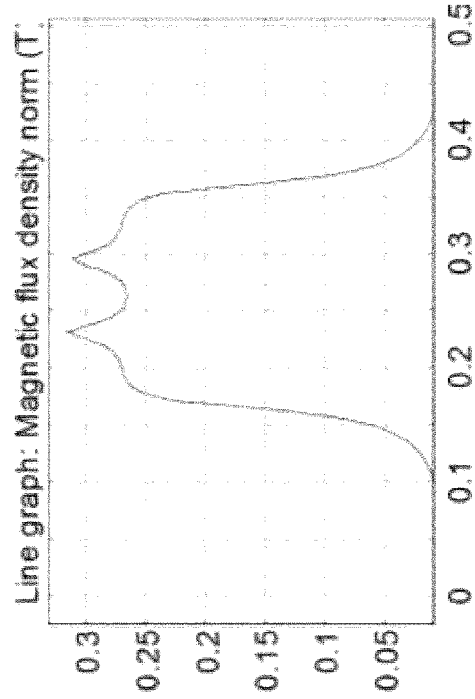
Figure 25C:
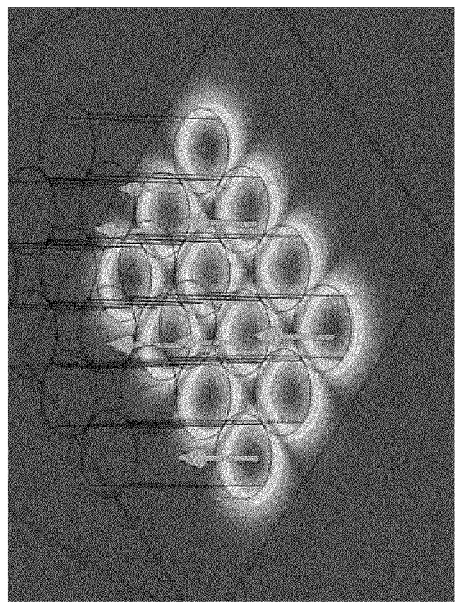
Figure 25D:
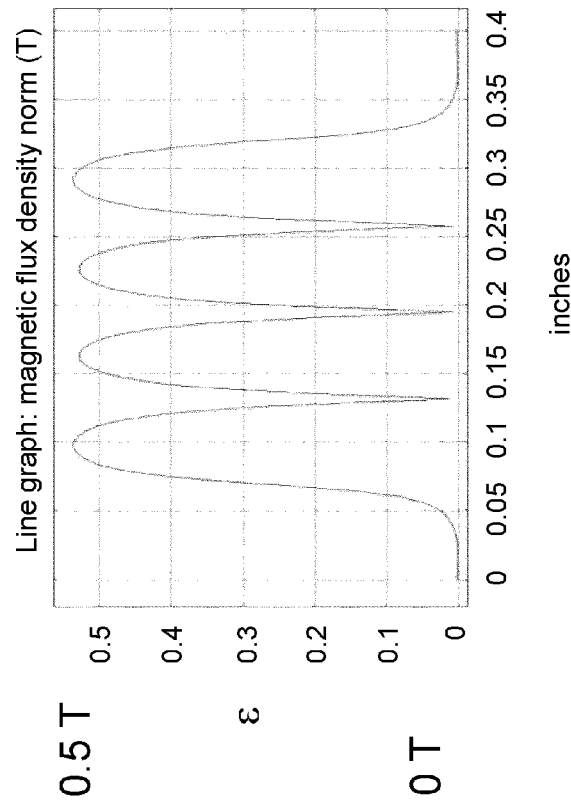
Figure 25E:
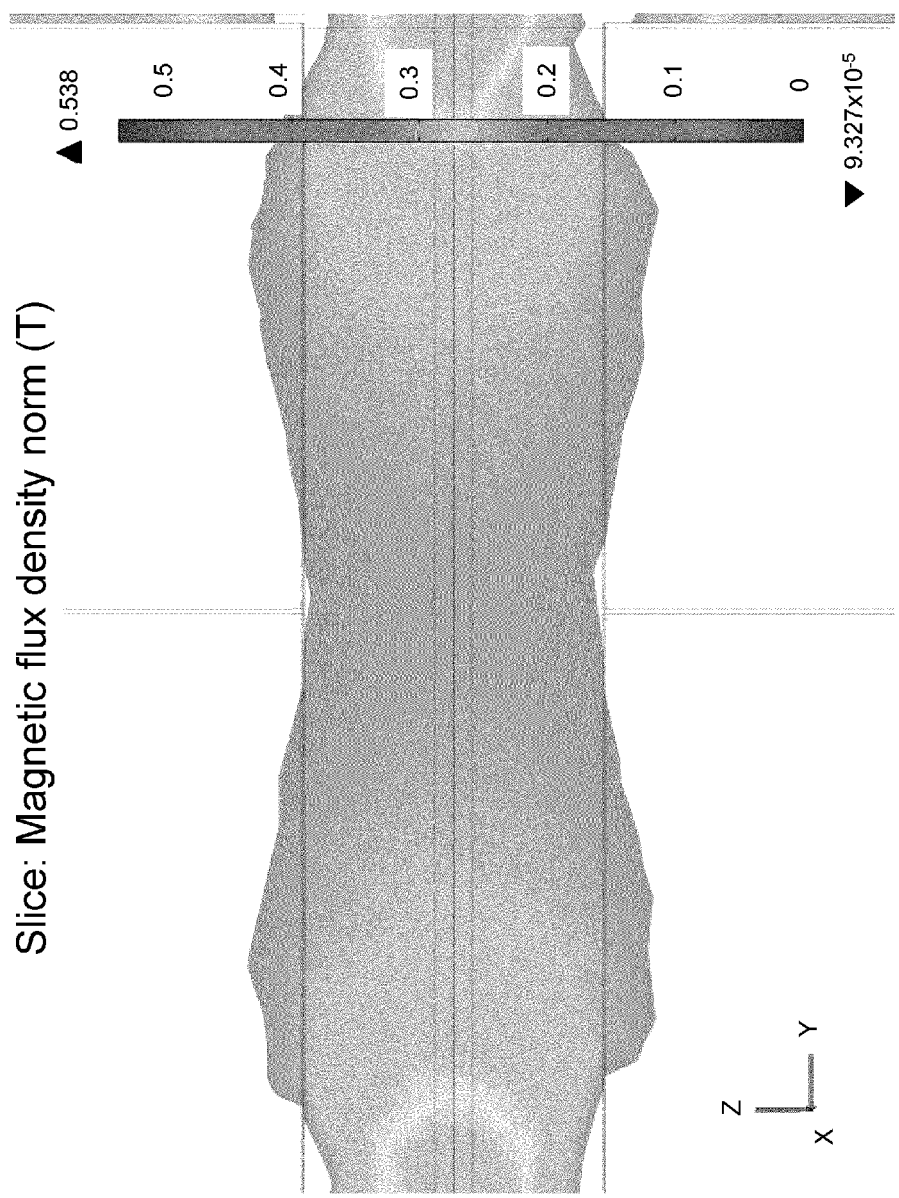

FIGS. 25A and 25B show the simulated magnetic field for a single-layer arrangement of 12 magnets. FIGS. 25C-25E show the simulated magnetic field for a double-layer arrangement (above and below the flow chamber) of 12 magnets.

These example arrangements were also tested experimentally for their influence on cell capture in the example device.

Figure 26A:
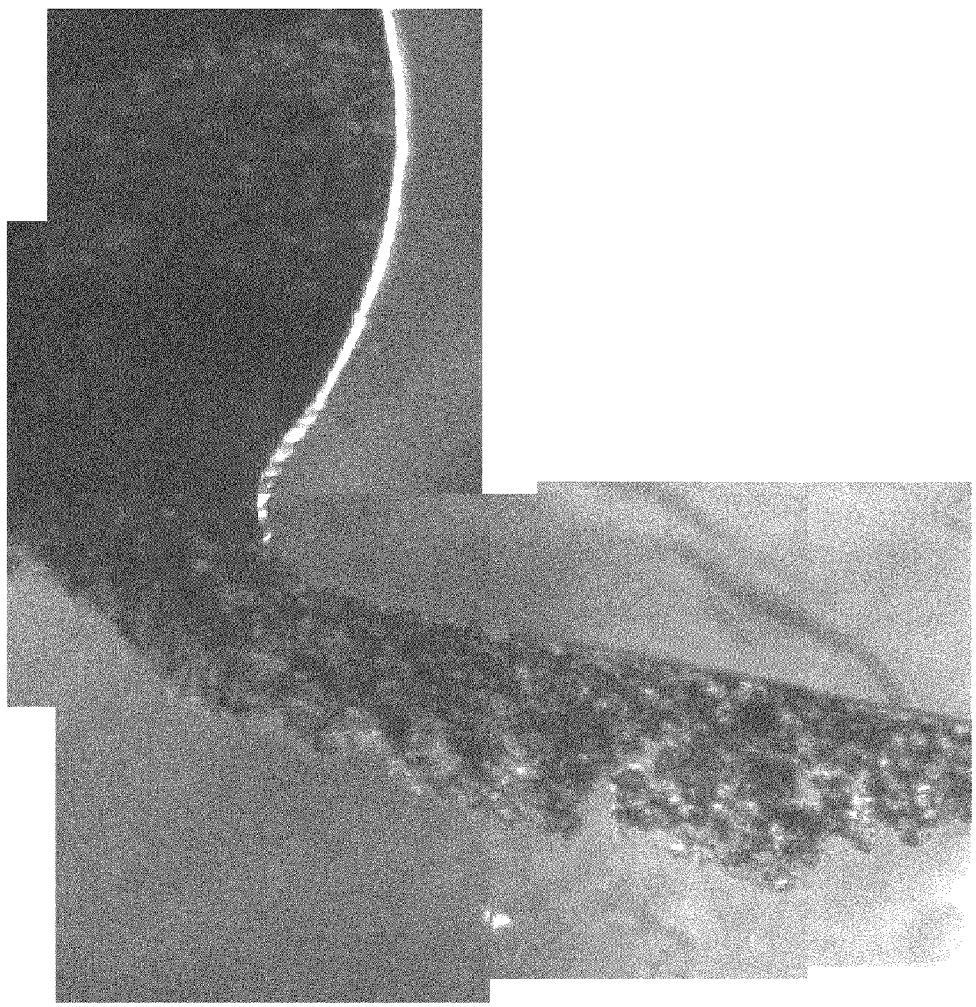
FIGS. 26A and 26B are images showing the effect of the example magnet arrangement of FIG. 22 in capturing target cells, in an example of the disclosed device.
Figure 26B:
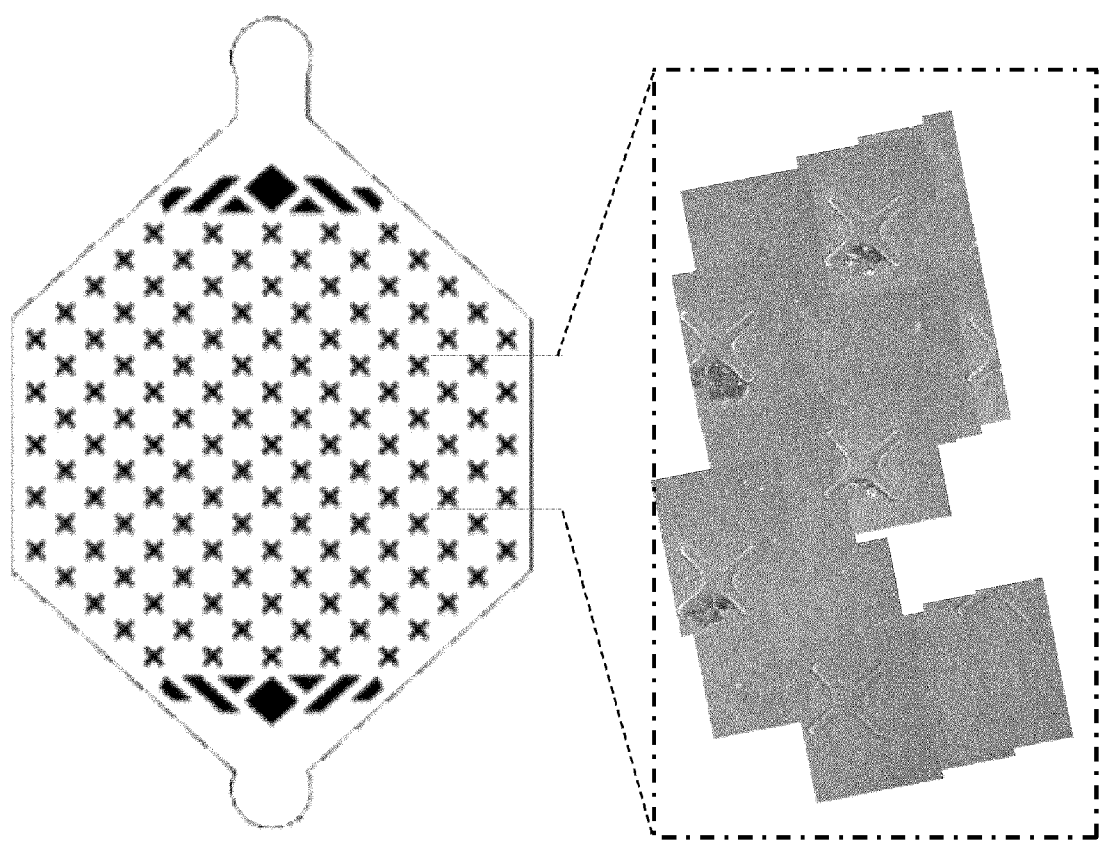

The arrangement of FIG. 22 was found to result in a capture efficiency of about 96% (out of a total of 5000 cells). However, because the resulting magnetic field was more concentrated near the flow inlet and outlet, cells were observed to be collected more near the inlet and outlet, resulting in clogging at the inlet and outlet (see FIG. 26A, for example). The captured cells were also found to be unevenly distributed in the flow chamber (see FIG. 26B, for example), which may be undesirable, as it may result in unwanted clogging of the flow chamber.

The arrangement of FIG. 24A was found to result in a capture efficiency of about 50% (out of a total of 5000 cells). A small amount of clogging at the flow inlet and flow outlet was still observed.

The arrangement of FIG. 25C was found to result in a capture efficiency of about 80% (out of a total of 5000 cells), with no clogging at the flow inlet and flow outlet.

The results of these simulations and tests suggest that a magnetic arrangement comprising a plurality of magnets arranged in two layers on either side of the flow chamber may give rise to acceptable capture efficiency while avoiding uneven distribution of captured cells. The arrangement of FIG. 25C was used in the example studies described in the present disclosure.

Example Fabrication Method

The disclosed device may be fabricated using any suitable method. In one example, an example device was fabricated in the form of a microchip. The example device was designed as shown in FIG. 1C, with X-shaped flow-reducing structures in the flow chamber. FIG. 6A is a magnified view of the X-shaped structures, showing example approximate dimensions. The example device was fabricated using rapid prototyping using poly(dimethylsiloxane) (PDMS) soft-lithography[30] starting with an SU-8 master on a silicon wafer (from University Wafer, MA). A PDMS (from Dow Chemical, MI) replica of the master was formed. After peeling the replica, holes were pierced for tubing connections. The replica was permanently sealed with a PDMS-coated glass slide. Bonding was enhanced and made irreversible by oxidizing both the replica and the cover in a plasma discharge for about 1 min prior to bonding. Silicone tubing was then added at the inlet and the outlet. The channel depth was about 50 μm. Other dimensions may be possible, depending on the application, for example. A deeper channel may be suitable for capture of larger particles, for example.

In this example, the PDMS chips were conditioned with Pluronic F68 Sigma (from St. Louis, Mo.) to reduce sample adsorption and washed with PBS (at about pH=7.4) before use. Two arrays of 56 NdFeB N52 magnets (from KJ Magnetics, PA), each about 1.5 mm diameter and about 8 mm long, were placed adjacent to the bottom and top surfaces of the chip (as shown in FIG. 1D) for the duration of the cell capture process.

Example Study

Example studies were carried out, using an example device fabricated as described above. The example device was studied in separate stages—capture of magnetic nanobeads alone; capture of target cells in a simple sample; and capture of target cells in a biological sample.

Figure 7A:
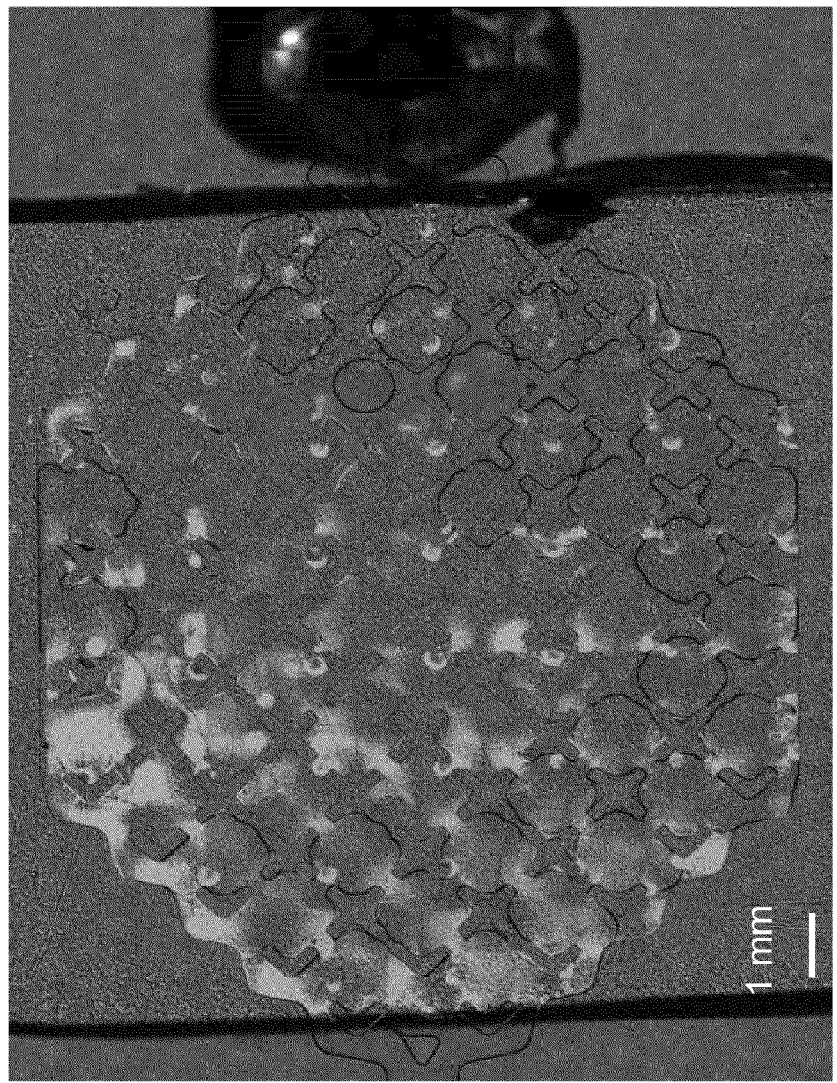
FIG. 7A is an optical microscopy image with fluorescent immunostaining of captured nanobeads in an example of the disclosed device.
Figure 7B:
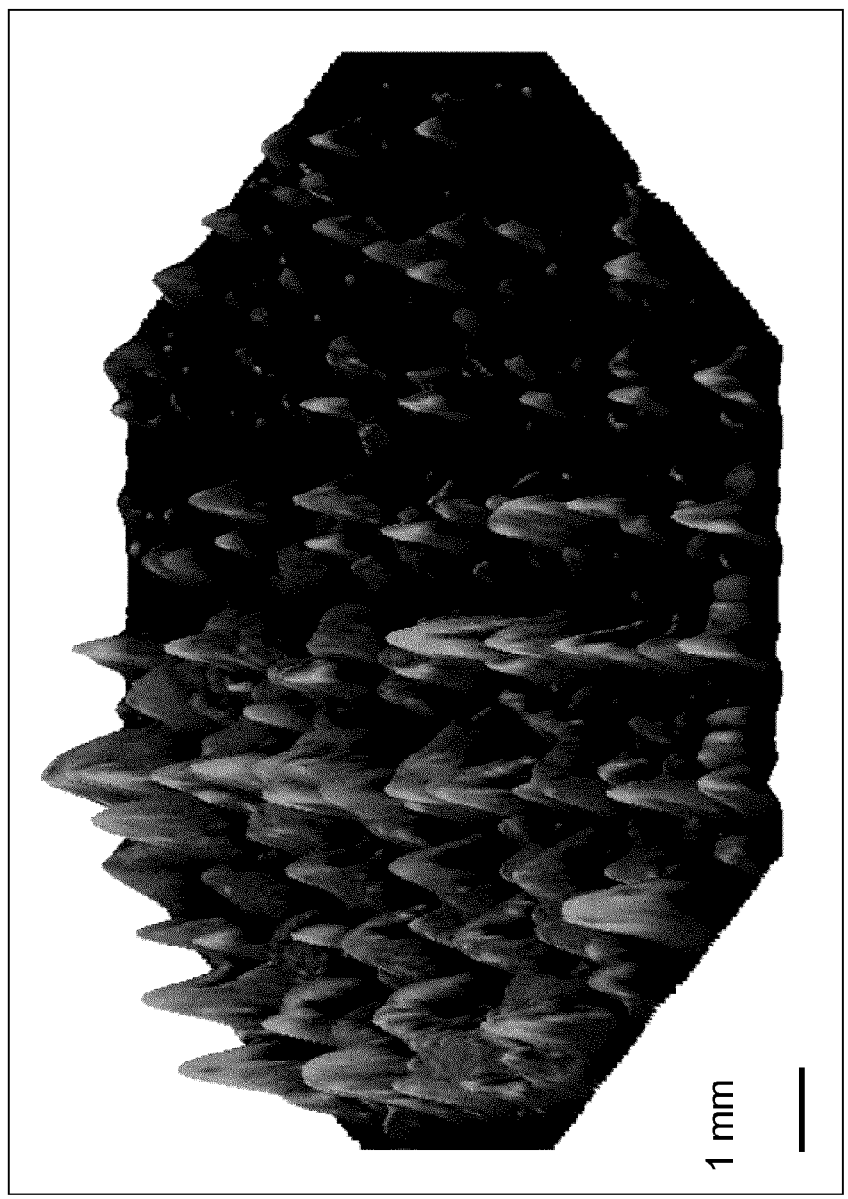
FIG. 7B is a 3D surface plot showing an example distribution of nanobeads captured in an example of the disclosed device.

FIGS. 7A and 7B are diagrams illustrating capture of magnetic nanobeads in the example device of FIG. 1C. FIG. 7A is an optical microscopy image of the device merged with fluorescent immunostaining of captured nanobeads inside the device. FIG. 7B is a 3D surface plot showing distribution of the nanobeads in the device. Nanobeads were observed to be captured throughout the flow chamber, but appeared to be more highly concentrated in area closer to the flow inlet (left side of image).

In the next stage, the device was studied using samples containing a known amount of target cells with a known amount of control non-target cells. The target cells were CTCs, namely VCaP cells—prostate cancer cells that over-express EpCAM—while the non-target cells were control U937 cells, which do not over-express EpCAM. The samples were mixed with paramagnetic nanobeads (about 50 nm in diameter) coated with anti-EpCAM, an antibody against the epithelial cell adhesion molecule that is often over-expressed in cancer cells and found on the surfaces of many types of CTCs. This was done to selectively label CTCs in the samples with the paramagnetic nanobeads. The sample was then introduced to the example device, at flow rate of 2 mL/h using a syringe pump. Next, about 200 µL PBS-EDTA was introduced into the device at a rate of about 2 mL/h (over about 6 min) to remove non-target cells.

In this example study, the efficiency of capture was measured by staining enucleated cells, and counting cells visualized with microscopy. This study also investigated immunostaining of the captured cells, by lysing the captured cells and performing mRNA analysis.

Taking away the applied magnetic field (e.g., by positioning the magnets away from the device) led to release of the captured target cells from the device. A low flow rate wash was then used to wash out the target cells. This may be an advantage of the disclosed device over devices that capture cells through an affinity to the device itself[6-8]. When the cell has an affinity to the device itself, strong agents and/or high flow rate washes may be required to release the captured cells from the device, which may result in damage to the cells. In contrast, the disclosed device may enable a very gentle approach to cellular release (such as by simply removing a magnetic field), which may help to facilitate the post-capture analysis of the cells without excessive perturbation. In some examples, such as where the disclosed device is used to capture more robust particles, such as non-cellular material, or more robust cells, a less delicate technique for removing captured particles from the disclosed device may be acceptable and appropriate.

Figure 2B:
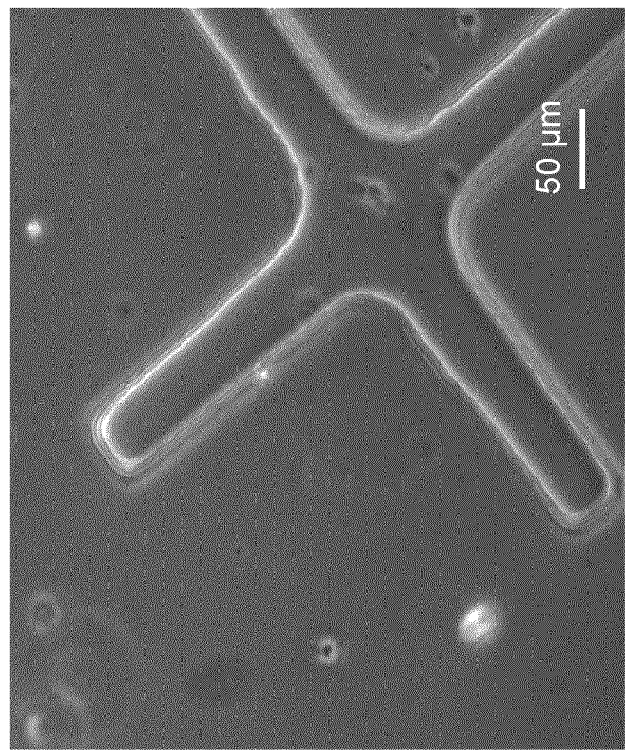
FIGS. 2A and 2B are images showing examples of capture of target cells and non-capture of non-target cells.
Figure 2A:
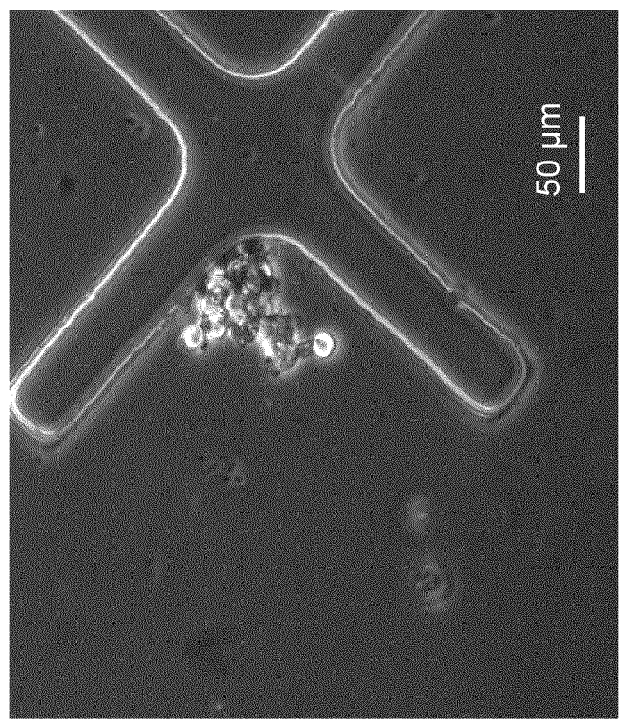

Using the approach described above, cells were observed to be captured in the expected portions of the flow-reducing structures. As shown in FIG. 2A, magnetically labeled VCaP cells—prostate cancer cells that over-express EpCAM—were captured at the X-shaped flow-reducing structure. As shown in FIG. 2B, control U937 cells, which do not over-express EpCAM and which therefore were not magnetically labeled, were not captured.

Figure 2C:
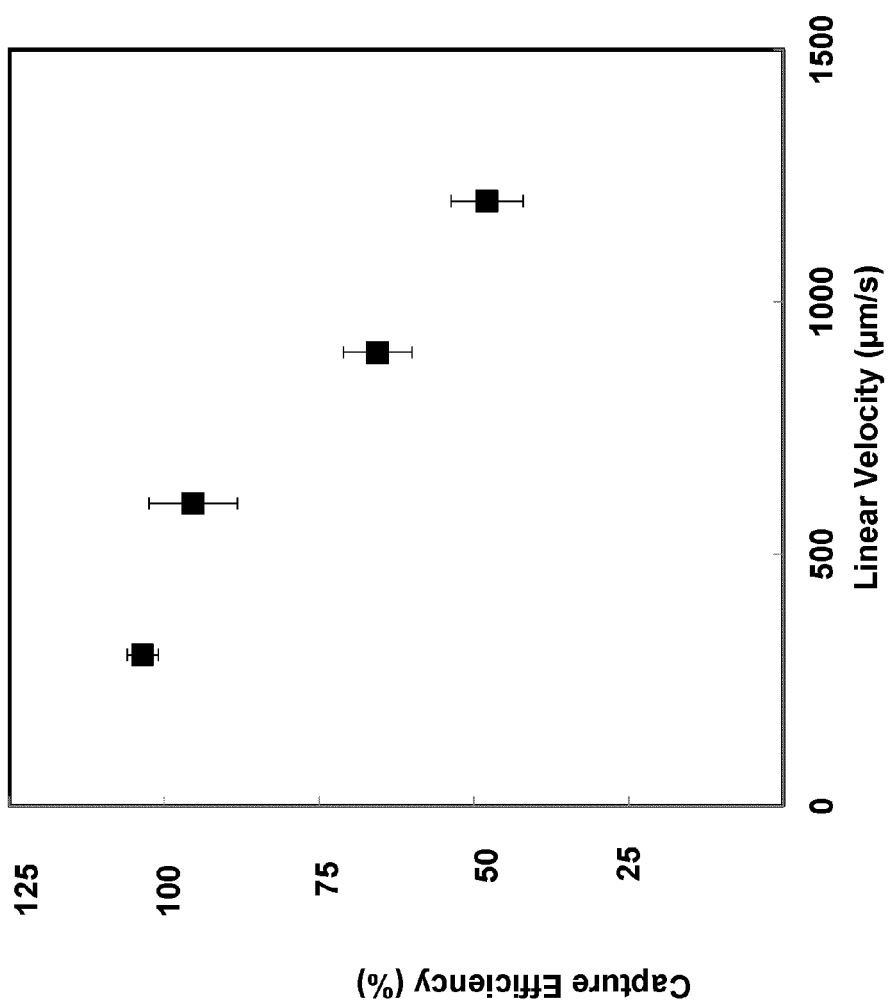
FIG. 2C is a chart showing example results illustrating the relationship between capture efficiency and linear flow velocity.
Figure 2E:
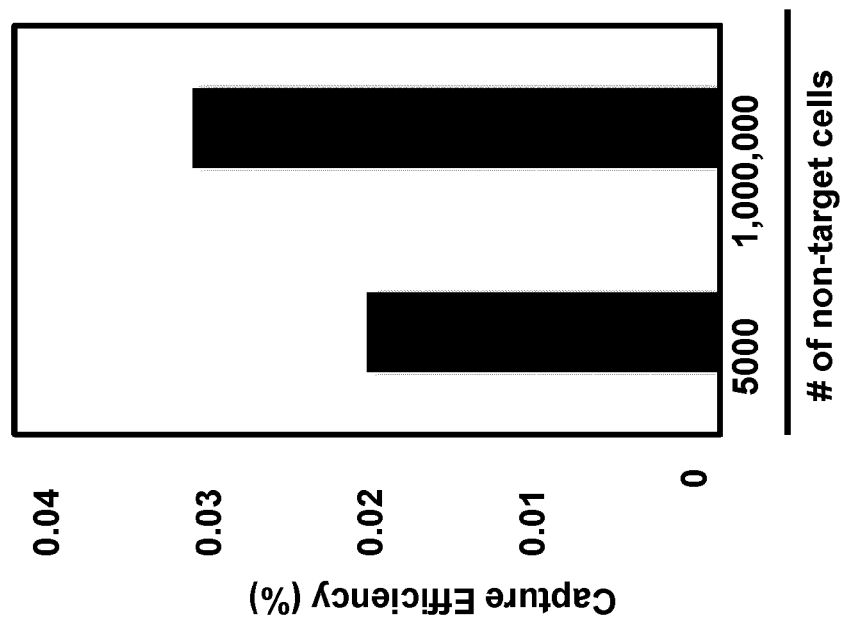
FIGS. 2D and 2E are charts showing example results comparing the capture efficiency of target cells vs. non-target cells by an example of the disclosed device.
Figure 2D:
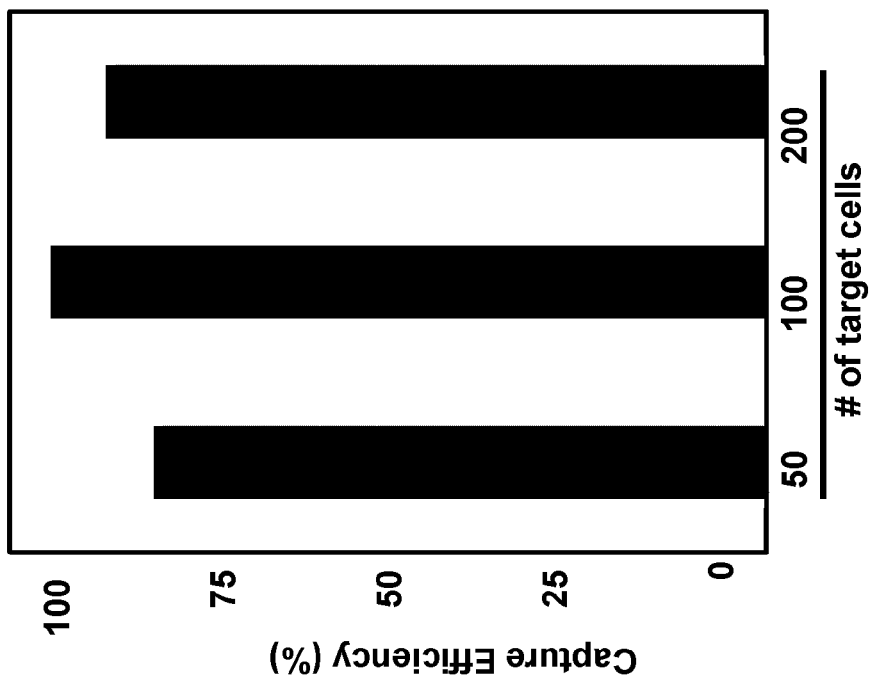

FIG. 2C is a chart showing capture efficiency of the example device as a function of linear velocity of flow through the device. The example results indicate that the capture efficiency was relatively high (about 100%) and decreased when the linear velocity of flow was over about 600 microns/second. FIGS. 2D and 2E are charts comparing capture efficiency of target cells versus non-target cells. The example results indicate that capture efficiency was relatively high (above 75%) at even low cell counts for the cells that were targeted with magnetic nanobeads, but were low (below 0.05%) for non-target cells even at high cell counts.

The capture efficiency of the target cells was found to be more than three orders of magnitude greater than that of the non-target cells. These results indicate that the example device was able to process a 2 mL through a flow chamber volume of about 5 µL at a flow velocity sufficiently fast to enable the entire sample to be processed by the device in about 1 hour.

Figure 2F:
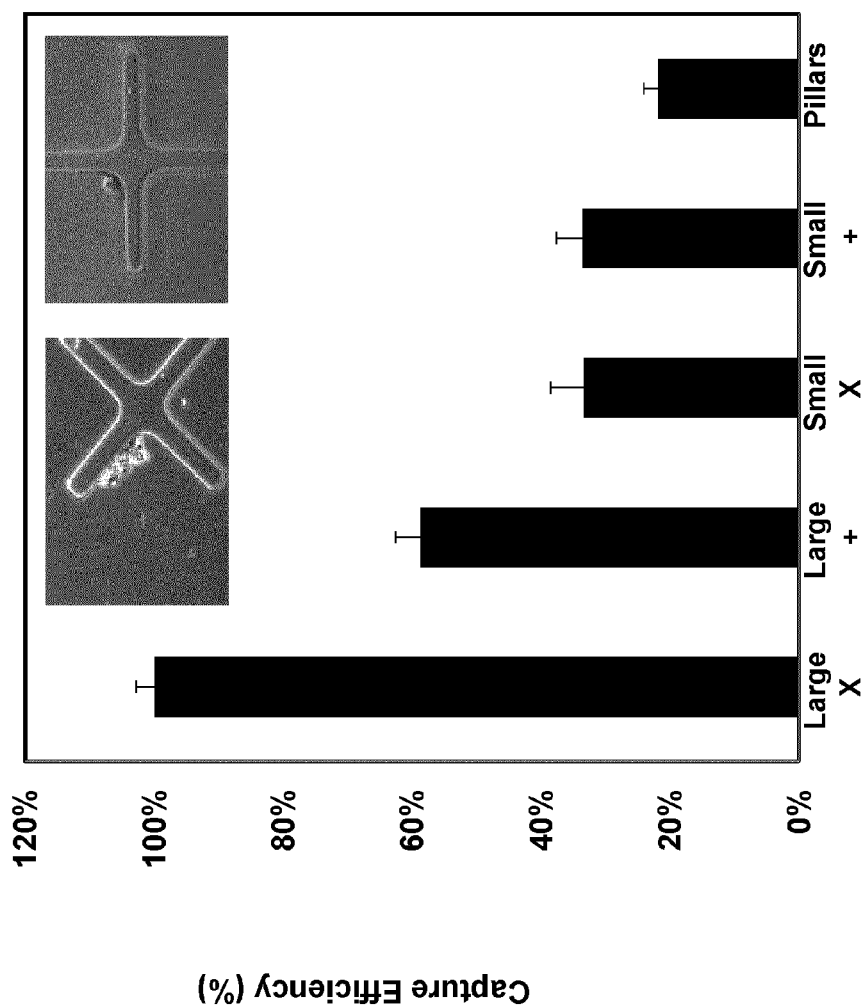
FIG. 2F is a chart showing example capture efficiencies of different example configurations of flow rate-reducing structures.

The example study also included validation of the simulations discussed above by fabricating devices having different configurations of flow-reducing structures, specifically where the flow-reducing structures were configured as large and small X-shaped, large and small plus-shaped, and pillar-shaped structures. Using a single set of experimental conditions, as described above, the capture efficiencies of the different flow-reducing structures were observed. FIG. 2F shows example results comparing the capture efficiency of flow-reducing structures having different configurations (in this case, X-shaped, cross-shaped and pillars, of different dimensions). The large-X configuration was found to have the highest capture efficiency of the configurations tested. These example results closely match the simulation results shown in FIG. 1B.

It was found that the capture efficiency followed a trend matching the fraction of the flow landscape where the flow rate was lower than the capture threshold (found to be about 0.09 mL/h) necessary for capture and retention. That is, the greater the percentage of the flow chamber where the flow rate is lower than the capture threshold, the greater the capture efficiency of the device. The example results indicate that the capture efficiency of the larger structures was superior to that of the smaller structures, and the X-orientation produced a greater fraction of low-flow region in the flow chamber, resulting in better capture efficiency.

Figure 3B:
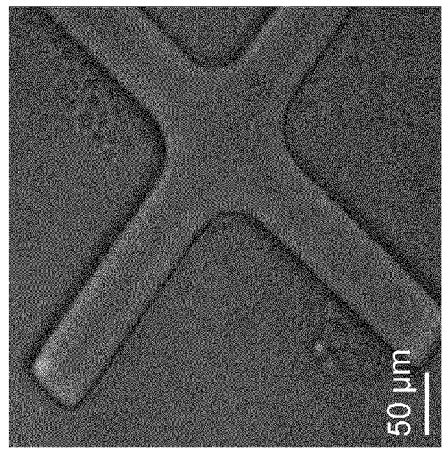
FIGS. 3B and 3C are optical and immunostained images of target cells captured in an example of the disclosed device.
Figure 3A:
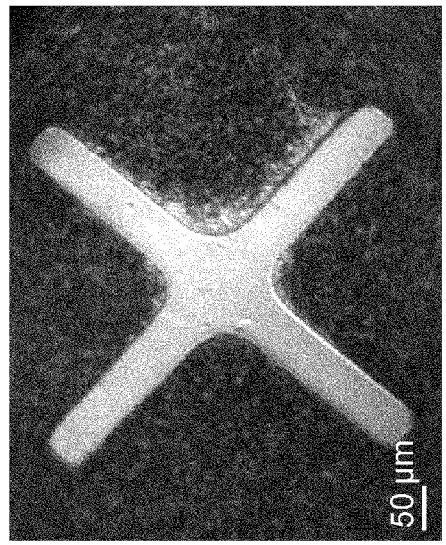
FIG. 3A is an image showing a blood sample in an example of the disclosed device.

In the next stage of the study, the performance of the example device was studied using a more complex sample, namely whole, undiluted blood. The example device was studied using whole blood samples spiked with different numbers of target cancer cells. FIG. 3A shows an example image of a whole blood sample passing through the example device.

The samples were mixed with paramagnetic nanobeads (about 50 nm in diameter) coated with anti-EpCAM, an antibody against the epithelial cell adhesion molecule that is often over-expressed in cancer cells and found on the surfaces of many types of CTCs. In this example, about 40 µL of anti-EpCAM Nano-Beads (from MACS) were added to about 2 mL of blood sample. This was done to selectively label CTCs in the samples with the paramagnetic nanobeads. The sample was then introduced to the example device, at flow rate of 2 mL/h using a syringe pump. Next, about 200 µL PBS-EDTA was introduced into the device at a rate of about 2 mL/h (over about 6 min) to remove non-target cells.

The captured cells were fixed and immunostained to distinguish non-target cells, in this case nucleated white blood cells (WBC), from target cells, in this case EpCAM-positive cells.

The non-specific red blood cells stopped in the device were washed out by introducing about 100 µL RBC lysis buffer (at a rate of about 2 mL/h, over about 3 min) into the example device, followed by 2 wash steps with PBS (about 200 µL each, at a rate of about 2 mL/h, over about 6 min).

For immunostaining, after passing the sample through the device, cells were fixed with 4% paraformaldehyde, and subsequently permeabilized with 0.2% Triton X-100 (from Sigma-Aldrich) in PBS. Cells were immunostained with primary antibodies, rabbit polyclonal Anti-CD45 (from Invitrogen, CA) and APC anti-human PSMA (from Biolegend, CA) followed by Alexa 594-Anti-Mouse (from Invitrogen) and Biotin-XX Goat Anti-Rabbit (from Invitrogen, CA) (at about 20 µg/mL) and Yellow-nanoB-Avidin (at about 1:500). All of the antibodies were prepared in about 100 µL PBS and stained for about 30 minutes at a flow rate of about 0.2 mL/h. The devices were washed between each staining step using about 200 µL 0.1% Triton X-100 in PBS, at about 0.6 mL/h for about 10 min. Nuclei were stained with about 100 µL DAPI ProLong Gold reagent (from Invitrogen, CA) at about 0.6 mL/h. After completion of staining, all devices were washed with PBS and stored at about 4° C. before scanning.

After immunostaining, the devices were scanned using a 10× objective and a Ziess microscope equipped with an automated stage controller and a cooled CCD (from Hamamatsu, Japan). Images were acquired with Volocity (from PerkinElmer, Waltham, Mass.) software. Bright field, as well as red, green and blue fluorescence images were recorded. The captured images were then analyzed using a macro prepared in ImageJ[31] and target and non-target cells were counted.

Figure 3E:
FIGS. 3D and 3E are optical and immunostained images showing non-target cells are not captured in an example of the disclosed device.
Figure 3D:
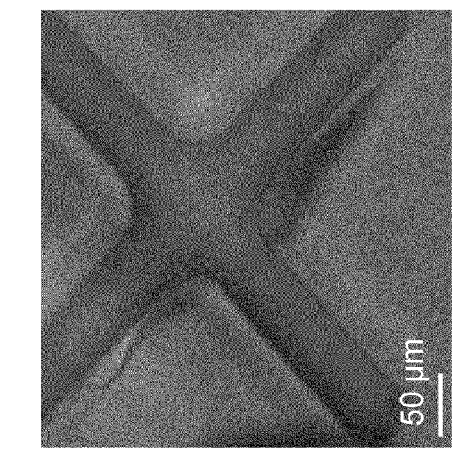
Figure 3C:
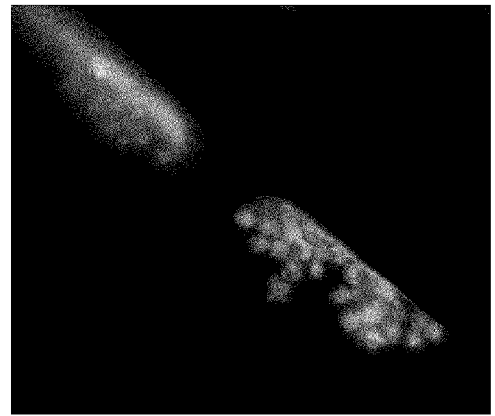
Figure 3F:
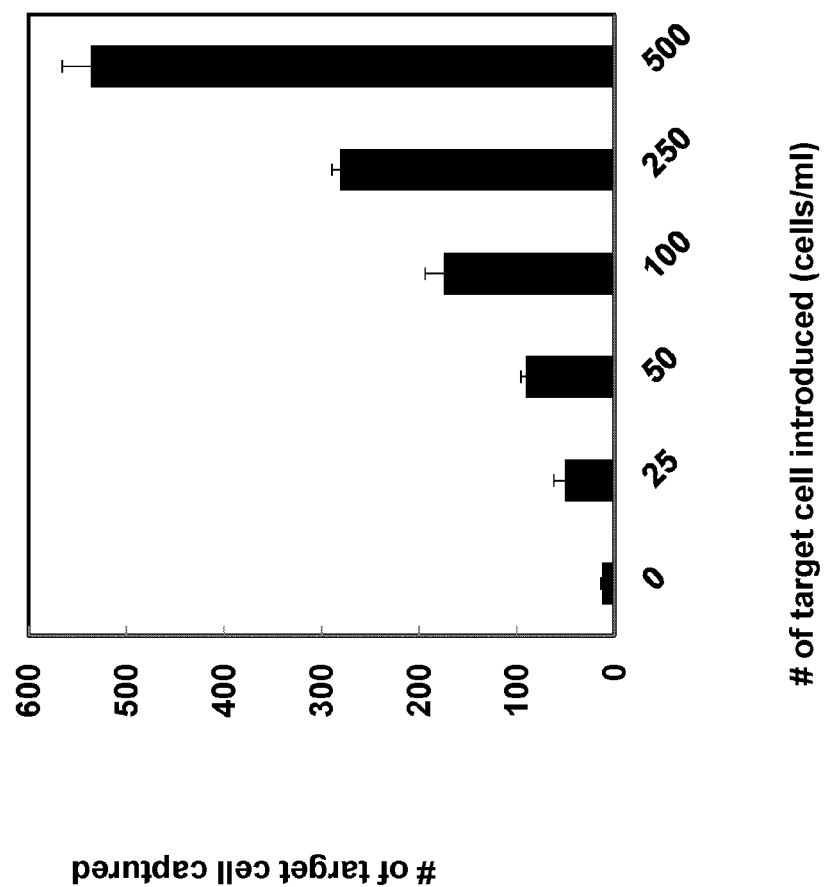
FIG. 3F is a chart showing example results illustrating capture efficiency of target cells in a whole blood sample, using an example of the disclosed device.

It was observed, using both bright field imaging (FIG. 3D shows an example image) and immunostained imaging (FIG. 3E shows an example image) that in control blood samples that did not contain spiked EpCAM-positive cells, cells were not captured by the flow-reducing structures. When VCaP cells were present in the sample, a significant number of stained cells were visible, as observed using bright field imaging (FIG. 3B shows an example image) and immunostained imaging (FIG. 3C shows an example image). To study this quantitatively, VCaP cells were introduced at levels ranging from 2-1000 cells per milliliter, and relatively high capture efficiencies were observed at every concentration studied (Table 2). FIG. 3F is a chart showing example results quantifying capture efficiencies of the example device for VCap cells spiked into whole blood.

mRNA Analysis

Although immunostaining may be commonly used for detecting CTCs, this may be a labor intensive and slow process, and may not provide specific information about the genetic features of cells. A chip-based approach to mRNA analysis may be relatively fast and sensitive[25-28], and may be applicable to the analysis of captured CTCs. Such an approach may be used to augment the information provided after capture of cells using the disclosed device.

The chip-based approach to mRNA detection may rely on the use of 3D nanostructured microelectrodes (NMEs) that can be coupled with electrocatalytic readout for mRNA analysis. PNA probes with sequences complementary to the mRNA encoding the prostate-specific antigen may be attached to NMEs. Given that the target cells studied in this example are prostate cancer cells, detecting this marker may enable specific identification of prostate CTCs.

Figure 4B:
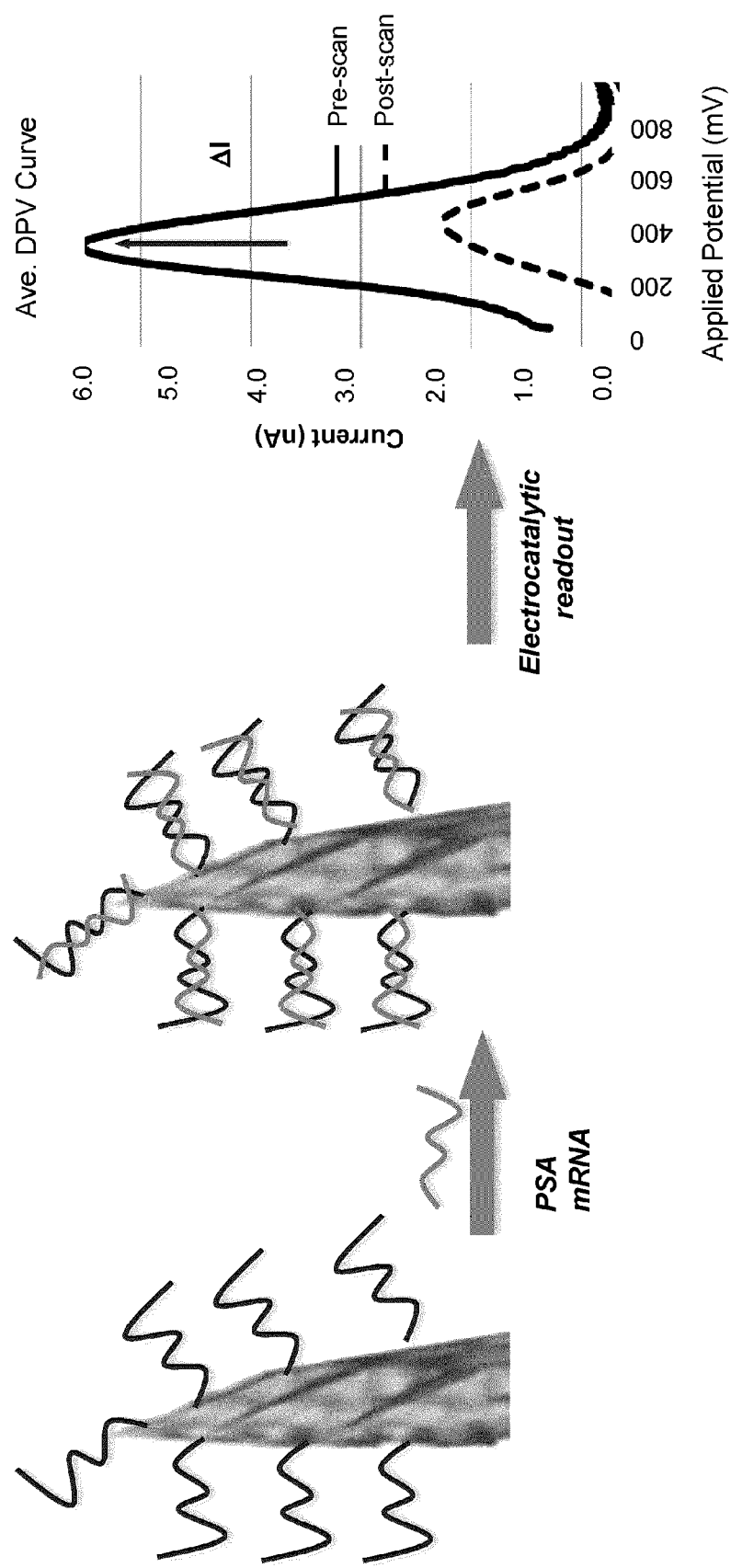
FIG. 4B is a schematic illustrating an example nanostructured microelectrode suitable for a detection chip.

FIG. 4A is a schematic showing an example system 200 comprising the example device 100 coupled to an electrochemical detection device 210. The detection device 210 may include NMEs 220 for mRNA analysis. FIG. 4B is a schematic illustrating how PSA mRNA may be sensed by a NME. As shown, PSA mRNA hybridizes to PNA probes immobilized on the surface of NMEs. This may lead to an increase in current as measured with differential pulse voltammetry after hybridization with PSA mRNA. Any other suitable configuration of the detection device 210 may be used. Such a system 200 may be suitable for chip-based electrochemical genetic analysis of mRNA from cells captured by the example device 100. In the example system 200, there may be no fluid communication between the device 100 and the detection device 210, necessitating the manual transfer of fluid from the device 100 to the detection device 210. In other examples, fluid communication between the device 100 and the detection device 210 may be possible (e.g., through the use of microchannels or tubing), which may be used for flow-through sensing, for example. Whether with or without fluid communication between the device 100 and the detection device 210, the device 100 and the detection device 210 may be provided together on the same base substrate or chip. Such an arrangement may be referred to as an integrated chip.

Although NMEs are described as a possible way to detect for a target particle, other sensing modalities may also be used. For example, the detection device 210 may implement any other suitable sensing electrode, including any suitable electrical or electrochemical sensing electrode, which may or may not include nanostructures.

An example method for fabricating the detection device 210 is described below. Other suitable methods and/or variations may be used. In this example, detection devices 210 were fabricated using thin silicon wafers passivated with a thick thermally grown silicon oxide layer. First, a positive photoresist was patterned to the desired electrical contact and lead structure using standard photolithographic methods. Subsequently, a 500 nm gold layer was deposited using electron-beam assisted gold evaporation and a standard lift-off process was used to expose the desired contact and lead structure. Next, a second layer of 500 nm silicon dioxide was deposited to passivate the lead structure using chemical vapor deposition. Finally, 5 µm apertures were etched into the second passivating silicon dioxide layer, exposing the gold layer at the end of each lead structure.

The layered structures were washed by sonicating in acetone for 5 min and rinsing with IPA and water. Nanostructured microelectrodes (NMEs) were electroplated using a standard three-electrode system comprising a Ag/AgCl reference, a Pt auxiliary and a 5 µm aperture Au working electrode. An electroplating solution containing 20 mM HAuCl4 in 0.5M HCl was used. NMEs were plated on the layered structure using an applied potential of 0 mV for 100 s. For finely nanostructured overlayer, a second electroplating solution was used (5 mM H2PdCl4 in 0.5M HClO4). The second electroplating was performed with an applied potential −250 mV for 10 s.

PNA probes were synthesized using a Protein Technologies Prelude peptide synthesizer. The following probe sequences are specific to PSA mRNA (P12) PSA (NH2-C-G-D-gtc-att-gga-aat-aac-atg-gag-D-CONH2). After the synthesis the probes were purified by HPLC. The probe concentration was determined by NanoDrop instrument. The molar excitation coefficients were calculated with "PNA calculator ver-2.0" program. A solution of 100 nM PNA probe in PBS was deposited on the NMEs surface in a dark humidity chamber overnight at RT. The detection device 210 may then be ready for use.

An example study was carried out to investigate this example system.

Small numbers of target cells, in this case VCaP cells, were spiked into two milliliters of blood. The example device 100 was used to capture the target cells. The captured cells were lysed inside the device 100 with an alkaline solution (about 15 µL of about 20 mM NaOH (for about 5 min) and neutralized with about 3 µL HCl (at about 100 mM)). This crude lysate was analyzed by recording electrochemical signals generated by a $Ru(NH_3)_6^{3+}/Fe(CN)_6^{3-}$ reporter system[29] before and after exposure to the sample.

Electrochemical measurements were made using an Epsilon potentiostat. After probe deposition and washing the free probe at 37° C. for 30 min and twice at room temperature for 5 min. The background signal (from the probe) was scanned in electrocatalytic solution (10 μM Ru(NH3)63+ and 1 mM Fe(CN)63−) in PBS. NMEs were incubated with purified total RNA, from cultured cells or CTCs, diluted with 0.3× PBS, at 37° C. for 1 hour. After hybridization the devices were washed twice with 0.3×PBS at RT for 5 min. The same catalytic solution was used for the device scanning before and after hybridization.

Figure 4C:
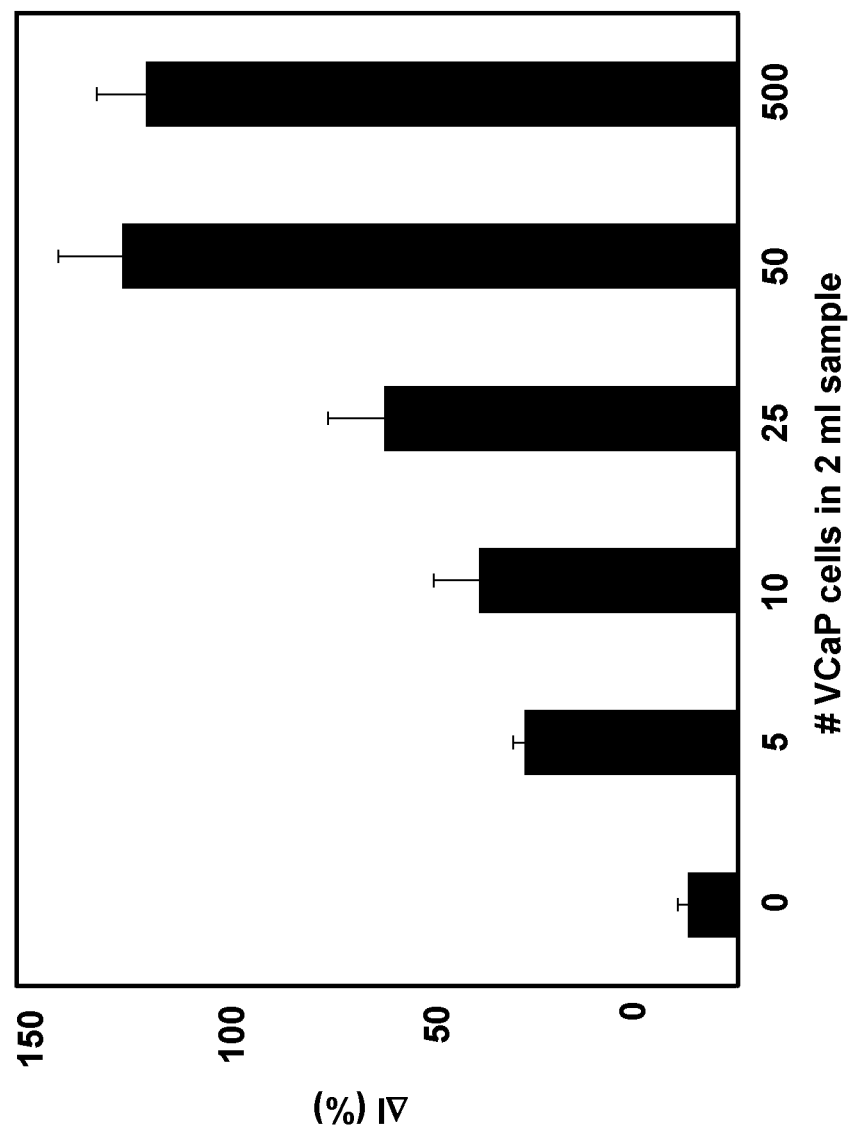
FIG. 4C is a chart showing example results of signal change as a function of target cells in a blood sample.

FIG. 4C is a chart showing example results of electrochemical signal change as a function of the number of VCaP cells spiked into a 2 mL blood. As shown in the example results, when as few as 5 cells were present in a 2 mL sample of blood, a statistically significant signal change was measured. The signal increased with the concentration of cells until it saturated when 50 cells were present. This low detection limit, which would allow the detection of a small number of CTCs in blood, indicated that CTCs in patient samples should be detectable using the example device, coupled with electrochemical readout.

Figure 4E:
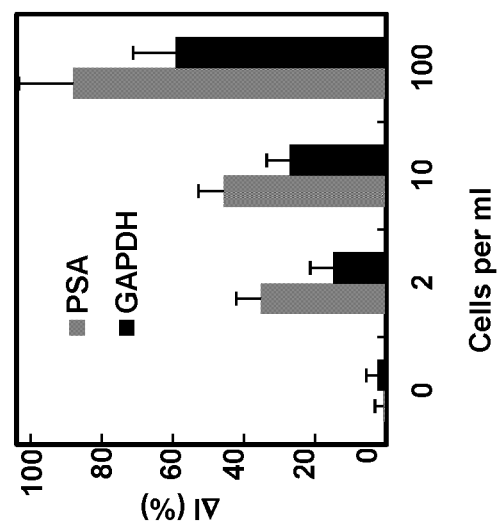
FIG. 4E shows example results from testing of specificity, to differentiate different cell lines, of an example of the disclosed device.
Figure 4D:
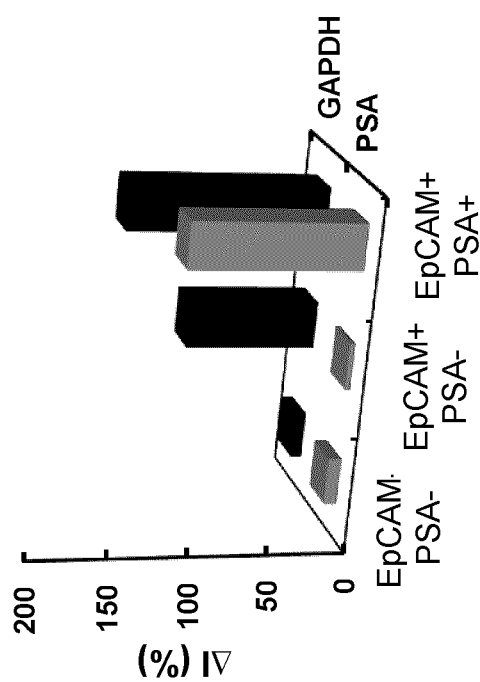
FIG. 4D shows example results from detection of two types of mRNA using an example of the disclosed device.

FIG. 4D shows example results in which two types of PNA probes, specific to PSA mRNA (specific to cancer cells) and specific to GAPDH mRNA (specific to all cells), were immobilized on the surface of NMEs in two different sensing wells of an example integrated chip. It was found that there was an increase in current after hybridization, as measured with differential pulse voltammetry.

FIG. 4E shows example results in which specificity of an example integrated chip was tested, using cell lines expressing both EpCAM and PSA (Vcap cell line), expressing only EpCAM but not PSA (DU-145), and expressing neither EpCAM nor PSA (U937). The example results showed that the example integrated chip enabled differentiation of cancer cells from nonspecific cells.

Polymerase chain reaction (PCR) was also tested as a readout strategy.

Lysate which was collected from the example device was used for cDNA synthesis with the First Strand DNA synthesis kit (Invitrogen) and Superscript III reverse transcriptase and random hexamers according the manufacturer's protocol. Then 2 μL cDNA was used in a 50 μL PCR reaction with 1 μL of 100 μM gene specific primers (specific to TMP/ERG Type III gene fusion and PSA gene). The two PCR primer-pairs were design to have annealing temperature of 57° C., which allows one RNA sample to be tested for TMP/ERG Type III mRNA and PSA mRNA at the same time. The PCR program was as follows: First, template denaturing at 94° C. for 3 min. following by 35 cycles: template denaturing at 95° C. for 30 s., primer annealing at 57° C. for 30 s. and DNA chain extension at 72° C. for 1 min. Then the PCR reaction was incubated at 72° C. for another 10 min. The PCR products were visualized using agarose gel electrophoresis. PCR primers for PSA gene (200 bp PCR product). Forward primer: (5'-gat-gac-tcc-agc-cac-gac-3') and Reverse primer: (5'-gtc-att-gga-aat-aac-atg-gag-gtc-c-3')

Figures 8, 9:
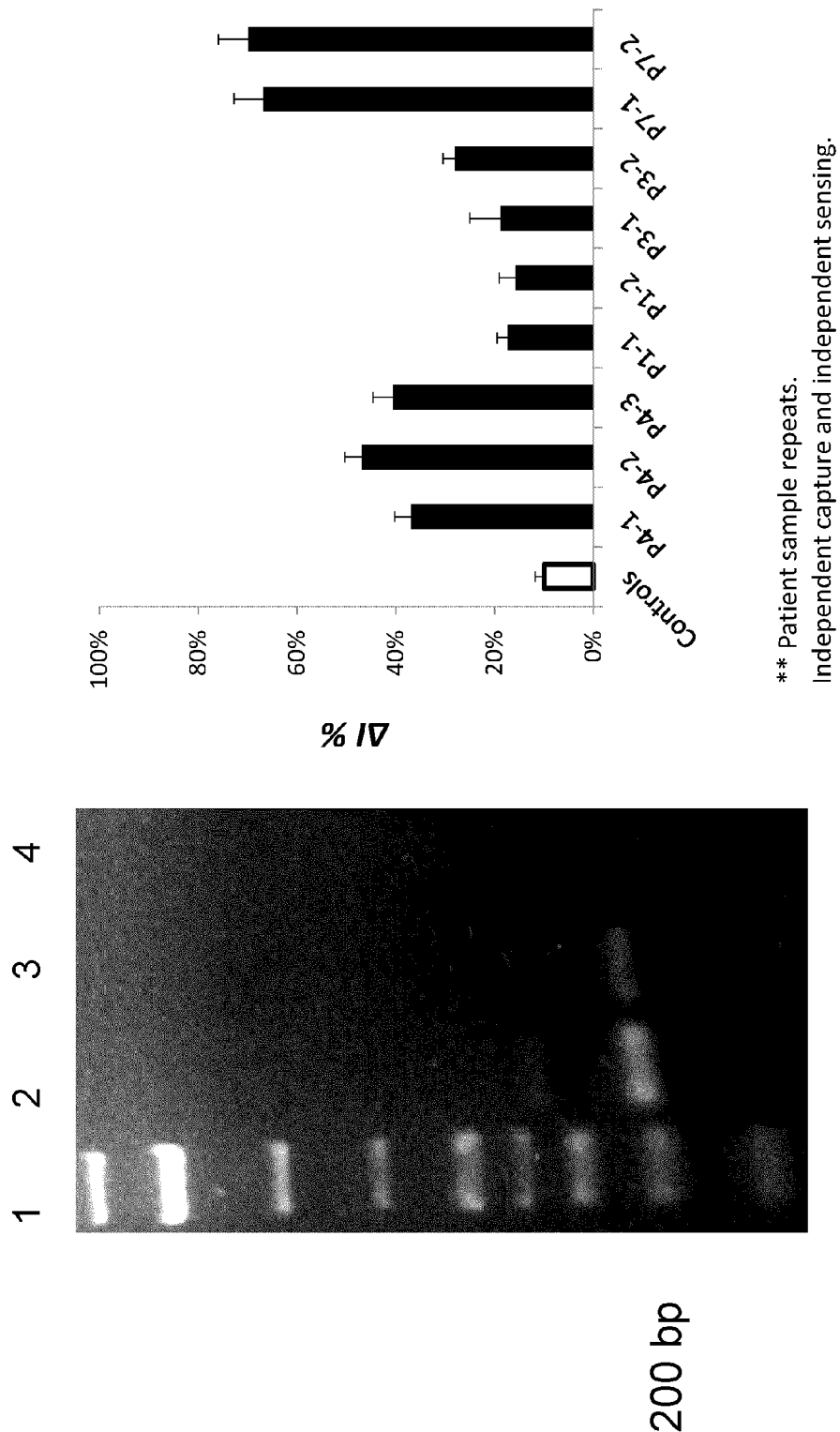
FIG. 8 is an image of an example gel electrophoresis comparing the cDNA of captured target cells to positive and negative controls.
FIG. 9 is a chart illustrating reproducibility of cell capture and electrochemical detection using an example of the disclosed device with an example detection chip.

FIG. 8 is an image of an example agarose gel electrophoresis of cDNA prepared from lysate of 1000 Vcap cells spiked in 2 mL blood and captured in the example device. In FIG. 8, lane 1 is the result from a 1 kb marker, lane 2 is the result from purified PSA cDNA (positive control), lane 3 is the result from Vcap cells spiked in blood, and lane 4 is the result from blood only (negative control).

Table 2 below shows the detection of target Vcap cells spiked in blood samples using different detection techniques—namely, RT-PCR, immunostaining and NME detection. It was found that PCR did not produce results comparable to immunostaining or NME detection at low cell counts. It may be that the magnetic nanobeads used for capture inhibited enzymatic amplification.

TABLE 2

Detection of VCaP cells spiked in 1 ml blood with different detection techniques

| Vcap Cells Spiked in 1 ml Blood | RT-PCR- gel electrophoresis on lysate | QPCR on purified mRNA* | Immuno-staining | NME (Electrochemical detection of PSA-mRNA) |
| --- | --- | --- | --- | --- |
| 0 | — | — | — | — |
| 2 | — | — | ✓ | ✓ |
| 5 | — | ✓ | ✓ | ✓ |
| 10 | — | ✓ | ✓ | ✓ |
| 25 | — | ✓ | ✓ | ✓ |
| 50 | ✓ | ✓ | ✓ | ✓ |
| 100 | ✓ | ✓ | ✓ | ✓ |
| 250 | ✓ | ✓ | ✓ | ✓ |
| 5,00 | ✓ | ✓ | ✓ | ✓ |
| 1000 | ✓ | ✓ | ✓ | ✓ |

*When PCR was done on crude lysate the detection was limited to 50 captured cells. A Dynabeads mRNA direct micro Kit (Invitrogen, CA) was then used to purify mRNA and using the purified mRNA in QPCR enabled a detection limit of 5 cells.

After testing the example device and confirming its capacity for efficient capture of target cancer cells spiked in blood, patient samples (6 biopsy-positive prostate cancer patients, and 5 healthy controls) were analyzed. Patient blood samples were collected with consent prior to prostate biopsy or radical prostatectomy. The characteristics of these patients are outlined in Table 1 below.

TABLE 1

Information on prostate cancer patient samples.

| Patient # | AGE AT DRAW | PSA AT DRAW | GLEASON SCORE AT DRAW |
| --- | --- | --- | --- |
| P1 | 70 | 721.0 | G8 (4 + 4) |
| P2 | 70 | 14.6 | G6 (3 + 3) |
| P3 | 66 | 1.3 | G8 (4 + 4) |
| P4 | 66 | 3.7 | G7 (3 + 4) |
| P5 | 61 | 4.8 | G7 (3 + 4) |
| P6 | 67 | 12.9 | G6 (3 + 3) |
| P7 | 83 | 7.4 | G9 (4 + 5) |
| P8 | 57 | 29 | G7 (4 + 3) |
| P9 | 61 | 4.67 | G7 (3 + 4) |
| P10 | 57 | 6.59 | G7 (3 + 4) |
| P11 | 68 | 5.32 | G7 (4 + 3) |
| P12 | 64 | 3.98 | G7 (3 + 4) |
| P13 | 72 | 9.7 | G9 (4 + 5) |
| P14 | 62 | 9.92 | G7 (3 + 4) |
| P15 | 67 | 4.51 | G6 (3 + 3) |

All blood samples were analyzed within a few hours from sample collection. The patient samples (2 mL) were incubated with the magnetic nanobeads and introduced directly into the example device. In this example study, multiple copies of the device were used, separate ones being used for immunostaining and for electrochemical analysis. Immunostained cells were counted as described above, and were observed at levels of 24 cells per milliliter and above for all the patient samples. In healthy controls, low cell counts were observed.

FIGS. 5A-5E show example images of CTC detection in patient samples. FIG. 5A shows an optical microscopy image of captured cells on a flow rate-reducing structure. FIGS. 5B-5D show corresponding fluorescent microscopy images, where cells are labeled with DAPI (in FIG. 5D), CTCs are stained for PSMA (in FIG. 5B), and WBCs for CD45 (in FIG. 5C). A captured CTC is marked with an arrow. FIG. 5E is a composite image combining FIGS. 5A-5D.

FIG. 5F is a chart of results of the example study, showing quantitation of CTCs counted in patient samples (n=6) and healthy controls (n=5) after immunostaining. FIG. 5G is a chart of results of the example study, showing electrochemical sensing of PSA mRNA of captured cells in the example device (same samples as in 5B). Each point shown is average of 1 to 3 independent capture experiments (2 mL blood/capture) and 6 to 10 electrochemical trials per capture.

When the PSA mRNA analysis was performed on the blood samples, a statistically significant signal change was observed for all 6 patient samples relative to the control. On several of the patient samples, multiple runs were performed with the same sample, and excellent run-to-run reproducibility was obtained. FIG. 9 is a chart illustrating the reproducibility of cell capture and electrochemical detection. Independent capture and sensing runs on the same patient sample give acceptable agreement in the electrochemical signal change.

These results indicate that the disclosed device, coupled with an electrochemical detection strategy (e.g., using a NME detection device), can be used to detect CTCs and confirm their identify using a specific genetic marker.

Example Device with Multiple Sorting Zones

Since capture of target particles may be flow rate-dependent, as discussed in the present disclosure, a mixture of particles may be sorted using an example device having multiple different flow rate zones. In a mixture of particles, those particles that are more susceptible to capture (e.g., more susceptible to an attraction force, such as magnetic attraction) may be captured in a high flow rate zone while those particles having a lower susceptibility to capture may be captured in a lower flow rate zone.

Although flow rate is discussed as an example, different sorting mechanisms (e.g., different attractive forces) may be used by different sorting zones in a single device, in order to sort the target particles. For example, different zones of the device may be subjected to magnetic fields of different strength. Different zones may also be coated with different coatings (e.g., complementary antigens) for capturing different target particles. Other such differences in attractive forces may be exhibited in different sorting zones within the same device, and these different types of attractive forces may be used in combination. In the example discussed below, sorting is carried out using different flow rates, although other sorting mechanisms may be similarly implemented, with or without different flow rates.

A device with different sorting zones may be useful for sorting particles that are labeled with different numbers of labels. For example, cells different amounts of magnetic nanoparticles may have different levels of susceptibility to capture by a magnetic attractive force. For example, thousands of nanoparticles may bind to a cell expressing a target surface marker (e.g., expression of a gene), and the exact number of nanoparticles bound to a cell may depend on expression levels of the target surface marker. Thus, different cells having different levels of expression may be sorted using an example device having multiple sorting zones, for example different flow rate zones. Such a capability may allow heterogeneous populations of cells, such as CTCs, to be separated and analyzed. This may be useful as there is evidence that circulating cells have variable expression profiles that may have clinical significance[32, 23, 24].

Figure 30:
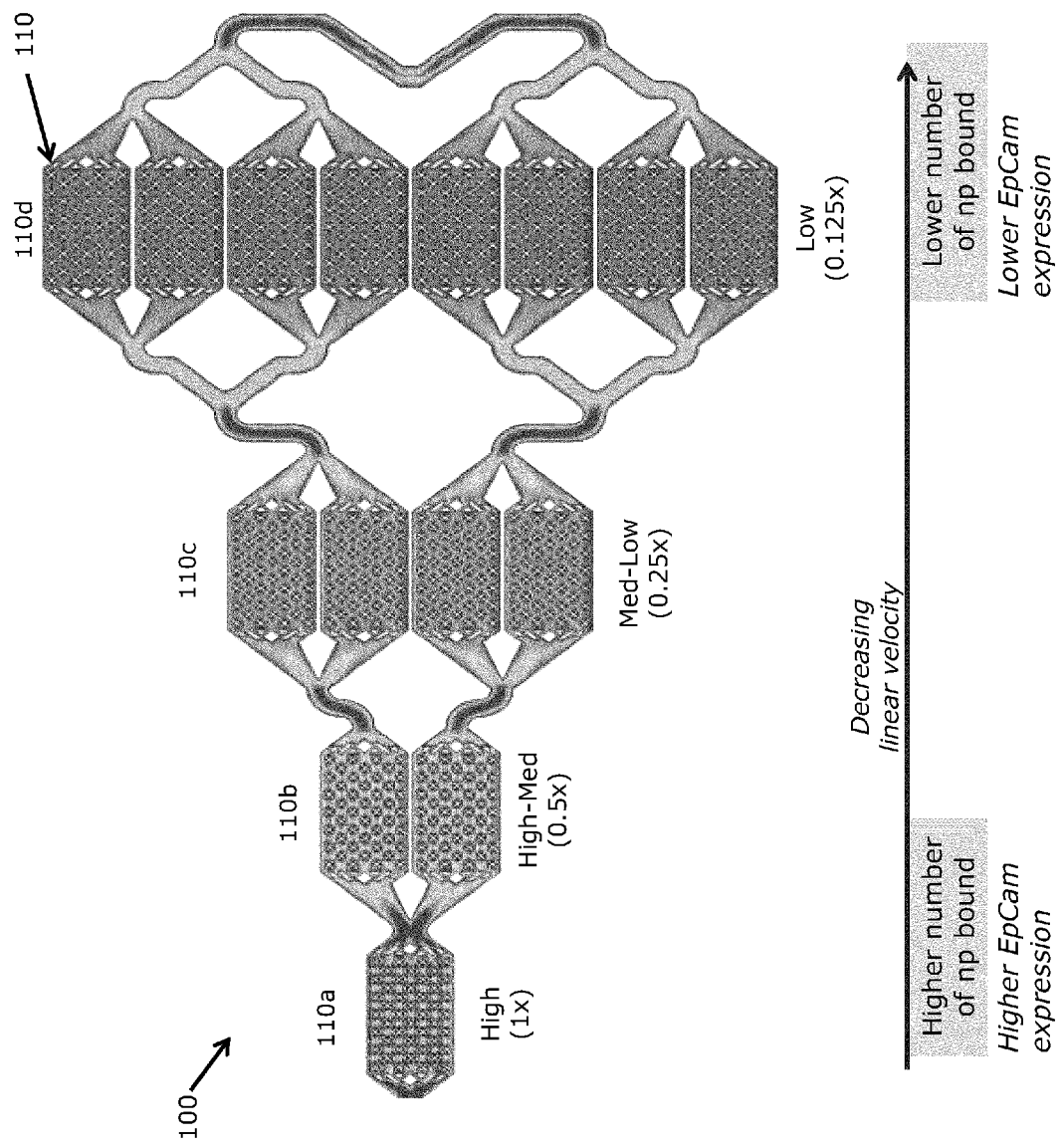
FIG. 30 shows an example multistep version of the disclosed device.

FIG. 30 shows a schematic of an example of the disclosed device 100 having multiple sorting zones, in this case multiple flow rate zones. The device may be referred to as a multistep device, and may be implemented as a microfluidic chip. The example device 100 of FIG. 30 may enable sorting of cells based on gene expression (e.g., EpCAM expression). The device 100 may include a flow chamber 110 comprising multiple compartments 110a, 110b, 110c, 110d. In this example, each of the compartments 110a, 110b, 110c, 110d may be configured to have different linear velocity profiles. Each compartment 110a, 110b, 110c, 110d may represent a different sorting zone, which may be referred to as Zone I, Zone II, Zone III and Zone IV, respectively, in the example shown. In this example, the inlet (not shown) is located to the left of the leftmost compartment 110a and the outlet (not shown) is located to the right of the rightmost compartment 110d.

The example of FIG. 30 shows different compartments 110a, 110b, 110c, 110d corresponding to different sorting zones, where the compartments 110a, 110b, 110c, 110d are discrete from each other. In other examples, different sorting zones may be provided without discrete compartments (e.g., where different portions of the flow chamber 110 are coated with different complementary antigens).

In this example, the first compartment 110a (that is, the compartment 110a closest to the inlet) may be designed to have a relatively high linear velocity that would only retain particles (e.g., cells) with relatively high susceptibility to attractive forces (in this case, a relatively high expression of EpCAM, resulting in a high magnetic nanoparticle population). The following three compartments 110b, 110c, 110d may be designed to have velocities that decreased stepwise by a factor of two. That is, the first compartment 110a has a relatively high average flow rate of about 600 μm/s (indicated as 1×), the second compartment 110b has an average flow rate half of that in the first compartment 110a (indicated as 0.5×), the third compartment 110c has an average flow rate a quarter of that in the first compartment 110a (indicated as 0.25×) and the fourth compartment 110d has an average flow rate an eighth of that in the first compartment 110d (indicated as 0.125×). The flow rate of 600 μm/s is provided as an example, and higher or lower flow rates may be selected based on the sample being analyzed, for example. The stepwise halving of flow rate is provided as an example, and other changes to flow rate across the compartments 110a, 110b, 110c, 110d, including increase or decrease by other factors, may be suitable.

In example studies (discussed below), the example device of FIG. 30 was used to capture cells exhibiting different levels of EpCAM expression. Cells with higher EpCAM expression may be expected to be captured in compartment 110a (Zone I). Although described as having a high flow rate, the first compartment 110a may be designed to have a velocity profile with areas of reduced flow rate that is still low enough to capture cells with high EpCAM expression (and hence higher population of magnetic nanoparticles attached) but that is too high to capture cells with lower EpCAM expression (and hence lower population of magnetic nanoparticles attached). Cells with lower EpCAM expression may be expected to travel longer in the device and be captured in subsequent compartments 110b, 110c, 110d. Compartment 110d (Zone IV) may be designed to exhibit a linear speed (and therefore dragging force) that is 8 times lower than in Zone I. Although described as having a low flow rate, the last compartment 110d may be designed to have a velocity profile that is still high enough to flush out non-target particles (e.g., cells having no EpCAM expression).

Figure 31A:
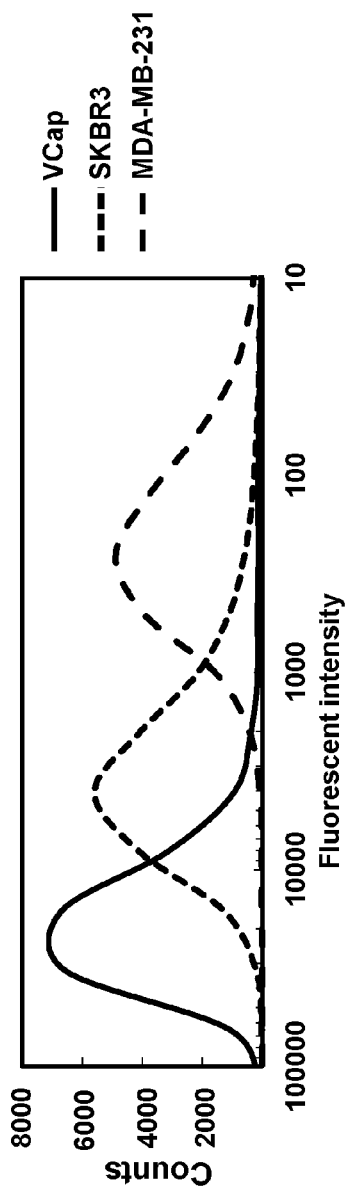
FIG. 31A is a chart illustrating expression of EpCAM on three example cell lines tested using an example of the disclosed device.
Figure 31B:
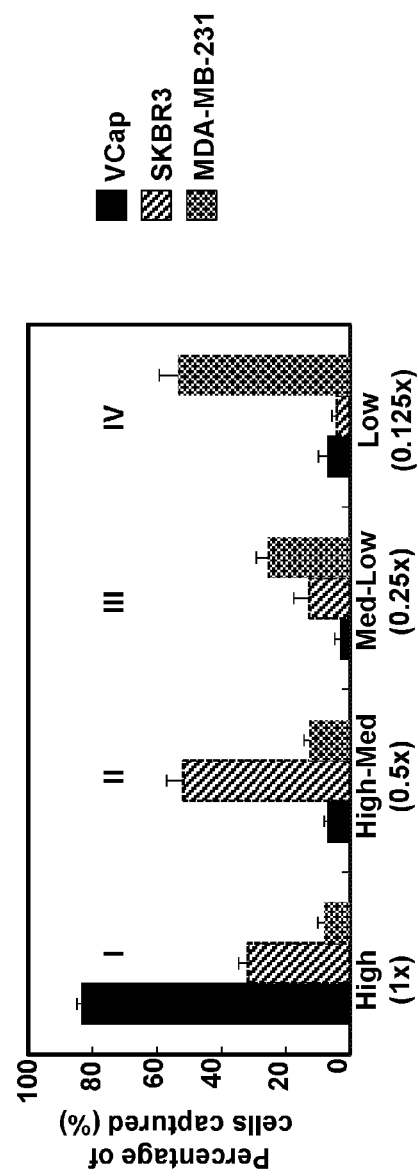
FIG. 31B is a chart illustrating capture of the example cell lines of FIG. 31A, in different zones of an example of the disclosed device.

In an example study, three cell lines that were known and validated to have different EpCAM expression levels (see FIG. 31A, illustrating different expression of EpCAM) were introduced into the example device of FIG. 30, and immunofluorescence was used to count the cells that were captured in each zone corresponding to each compartment of the device (see FIG. 31B, illustrating the percentage of cells captured in each Zone). The three different cell lines with different levels of EpCAM showed a distinctly different, and reproducible pattern of distribution within the device. VCap cells, which have a relatively high level of EpCAM expression, were mainly found in Zone I, as the relatively high number of nanoparticles bound to their surfaces allowed them to be retained despite a relatively high flow velocity. SKBR3 cells, which have approximately 10-fold lower level of EpCAM expression, were found predominantly in Zones I and II. MDA-MB-231 cells, which have EpCAM levels reduced about another 10-fold, were found mainly in Zones III and IV. These results indicate that cells can be sorted according to expression levels of a surface marker, using the example device, and that even cells with relatively low EpCAM expression may be captured. The device may be modified to have more (or less) sorting zones if a finer (or coarser) separation of particles was desired. Different attractive forces, such as described above (e.g., different surface antigens) may be employed for different sorting mechanisms, for example depending on the cells and/or markers.

Figure 32B:
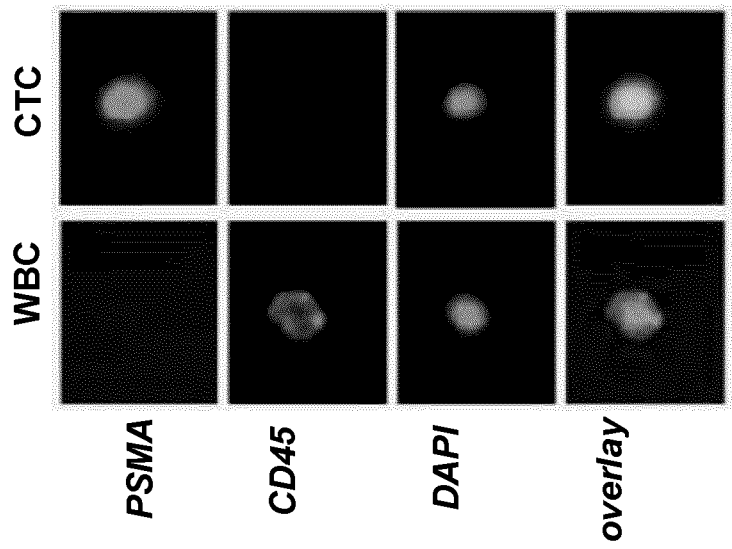
FIG. 32B shows images from optical and fluorescent microscopy of an example captured CTC.
Figure 32A:
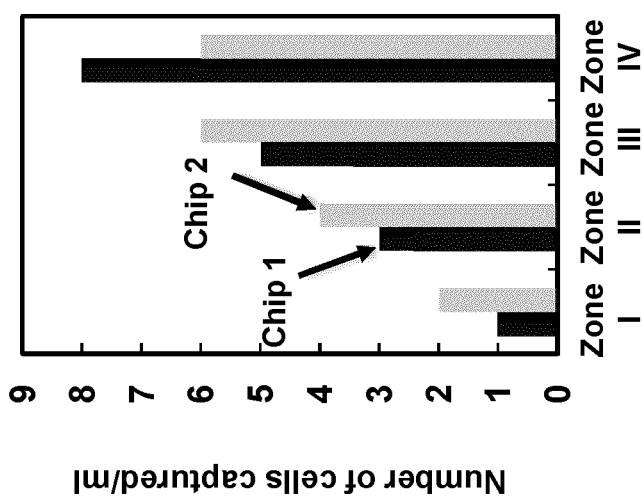
FIG. 32A is a chart illustrating two repeats of cell capture performed on samples from the same patient using an example of the disclosed device.

In another example study, a small set of patient samples was also analyzed using an example device having multiple sorting zones, along with immunostaining, to demonstrate effectiveness of the disclosed device with clinical samples, and to determine whether different patients exhibited variations in expression of EpCAM. A single sample collected from a patient with prostate cancer was sorted using two identical devices to first determine whether the data obtained from patient samples was reproducible (see FIGS. 32A and 32B), and it was found that a single sample yielded a relatively consistent profile in the two identical devices, even when very small numbers of cells were discovered. FIG. 32A is a chart illustrating a similar pattern of CTC capture for the sample passed through two identical devices. FIG. 32B shows images from optical and fluorescent microscopy of an example captured CTC. Nuclei are stained with DAPI, CTCs are stained for PSMA, and WBCs for CD45.

Figure 33A:
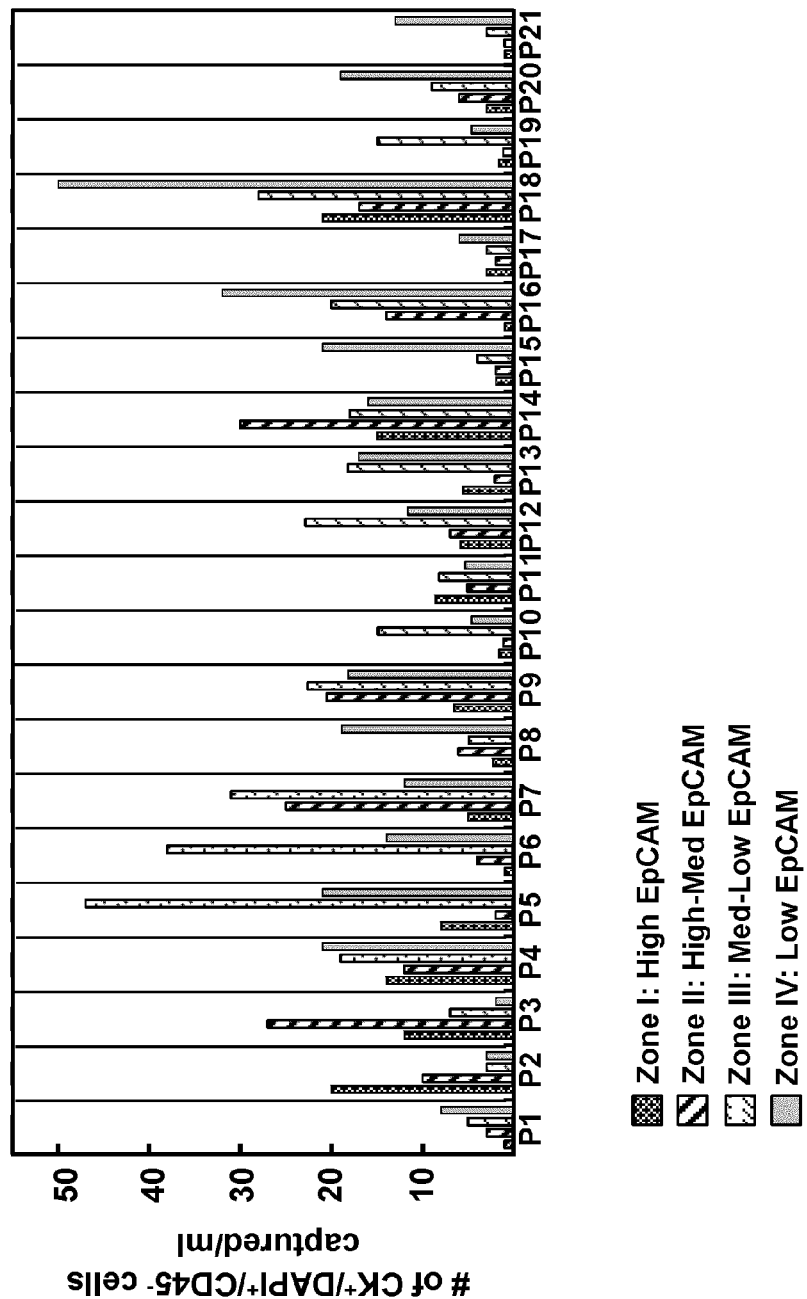
FIGS. 33A, 33B and 33C are charts showing different EpCAM expression patterns from CTCs captured from 24 different patient samples, using an example of the disclosed device.
Figure 33B:
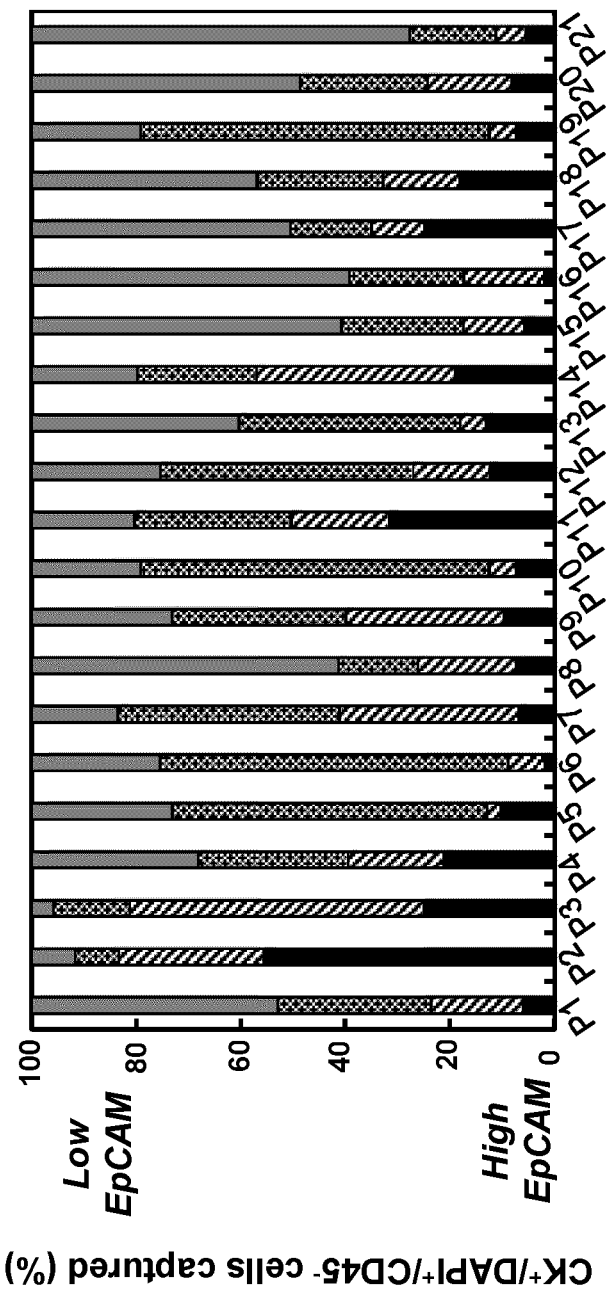

In another example study, a set of 24 prostate cancer patient samples was analyzed using the example device of FIG. 30. FIG. 33A and FIG. 33B are charts showing the number and percentages of cells captured in different Zones. The results show distinctly different profiles for each sample, indicating a relatively high degree of heterogeneity within a single patient's CTCs. One sample (P2) exhibited the highest percentage of cells captured in Zone I, while another (P1) had the highest percentage of cells captured in Zone IV. The fact that these patient samples all exhibited different profiles may be because prostate CTCs are thought to undergo the epithelial-to-mesenchymal transition, where expression of epithelial markers like EpCAM would be expected to decrease. It may be clinically relevant to monitor this transition, as prostate cancer CTCs are thought to be more likely to create metastases if they have become mesenchymal[32]. Each Zone's attractive force (in this example, a magnetic field) can also be chosen independently to further facilitate characterization of these different subpopulations.

Figure 33C:
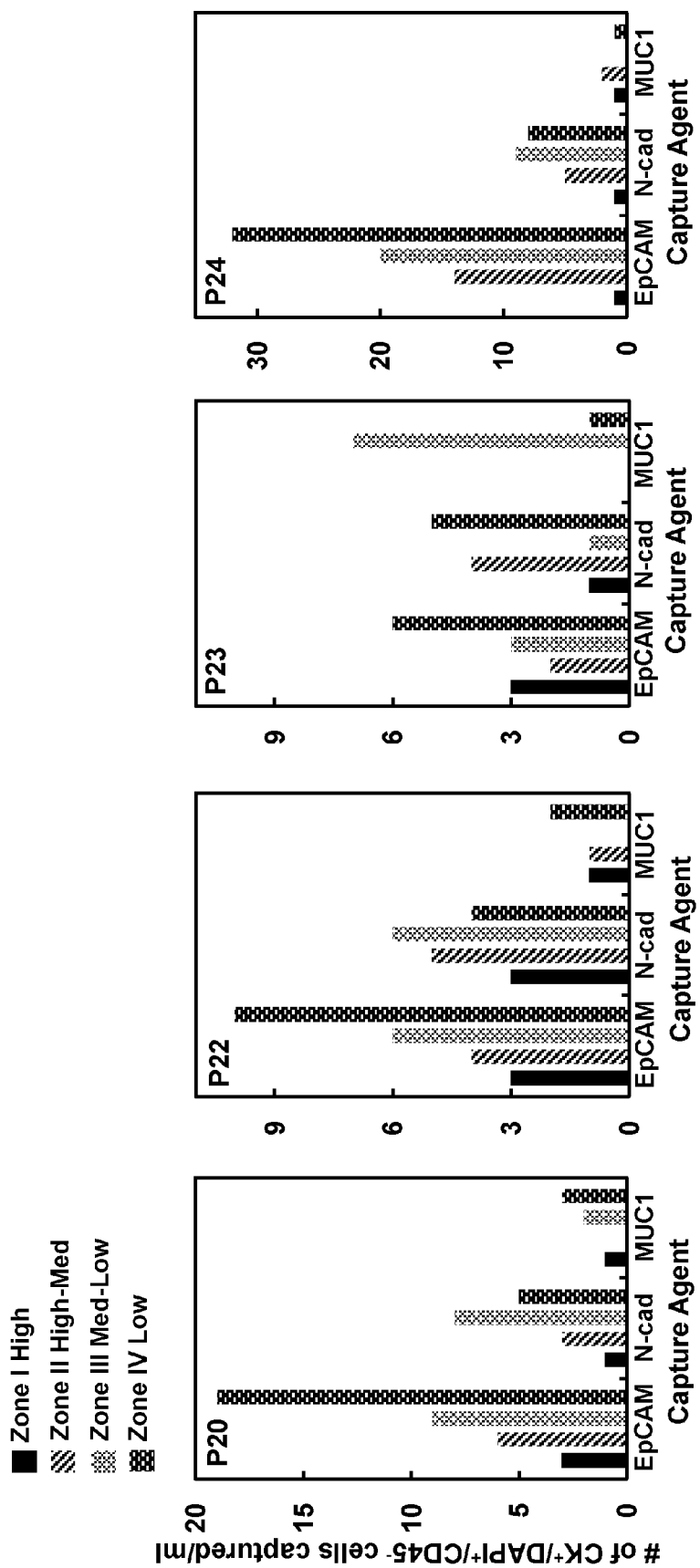

In FIG. 33C, prostate cancer patient samples were divided into 3 aliquots and treated with magnetic nanoparticles functionalized with anti-EpCAM, anti-N-cadherin, or anti-MUC1. Samples were run through the example device and subjected to immunofluorescence analysis to reveal the presence of CK (Cytokeratin), CD45, and DAPI. CTCs were counted if they were DAPI+/CK+/CD45−. These example results indicated that the example device could be used for detection using antibodies other than anti-EpCAM antibodies.

The present disclosure provides a microfluidic device having flow rate-reducing structures in a flow chamber. By creating microscale regions of low flow rate within a fluidic device, an attraction force (e.g., magnetic force) may be sufficient to allow the capture of target particles (e.g., cancer cells that have been labeled by magnetic nanobeads). The present disclosure may provide a method for capturing target particles, in particular particles that are present in small amounts in a sample. The capture of target particles may be relatively non-destructive and fast, and may be suitable for the study and analysis of circulating tumor cells and other rare cell types.

In various example embodiments, the present disclosure provides a device for capture of target particles in a flow, where the device may include: a flow chamber in fluid communication with a flow inlet and a flow outlet; and a plurality of flow rate-reducing structures in the flow chamber, each structure comprising a trapping surface shaped to reduce flow rate in a vicinity of the trapping surface; wherein reduced flow rate in the vicinity of the trapping surface is non-zero and has a magnitude lower than that of flow rate in other regions of the flow chamber; and wherein the reduced flow rate is sufficiently low for an attraction force acting on the target particles to overcome drag force on the target particles, to promote capture of particles in the vicinity of the trapping surface.

In some examples, the attraction force may be a magnetic force.

In some examples, the device may include at least one magnet for generating the magnetic force.

In some examples, there may be a plurality of magnets arranged in pairs of opposing polarity, one half of each pair being arranged in a first array and a remaining half of each pair being arranged in a corresponding second array, the flow chamber being positioned between the first and second arrays.

In some examples, the at least one magnet may be configured to generate a magnetic field gradient over the flow chamber.

In some examples, the trapping surface of at least one flow rate-reducing structure may include at least one concave surface, the concave surface being concave towards a direction of flow from the inlet to the outlet.

In some examples, the trapping surface of at least one flow rate-reducing structure may be defined by two joined arms defining an angle.

In some examples, the flow rate-reducing structures may include at least one X-shaped structure or cross-shaped structure, wherein the trapping surface is defined by two arms of the X-shaped or cross-shaped structure.

In some examples, the structures may be regularly spaced in the flow chamber.

In some examples, the structures may be arranged in a plurality of rows substantially perpendicular to the direction of flow, the rows being staggered with respect to each other.

In various example embodiments, the present disclosure provides a method for capturing target particles in a sample, where the method may include: introducing the sample containing the target particles to an example of the disclosed device, the target particles being susceptible to a magnetic attraction force; applying a magnetic field to the flow chamber while flowing the sample through the flow chamber, the magnetic field having a gradient over the flow chamber; removing the magnetic field; and eluting the target particles captured in the flow chamber.

In some examples, the target particles may be labeled with magnetically susceptible nanobeads.

In various example embodiments, the present disclosure provides a system for detecting target particles in a sample, where the system may include: an example of the disclosed device; and a detection device comprising sensing electrodes; wherein the sensing electrodes generate an electrical signal in response to contact of the target particles with the sensing electrodes.

In some examples, the sensing electrodes may include a sensing surface including an electrical or electrochemical reporter system targeted towards the target particles.

In some examples, the sensing electrodes may be nanostructured microelectrodes (NMEs) comprising surface groups complementary to the target particles.

The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entirety.

REFERENCES

1. Tibbe, a G. et al. Optical tracking and detection of immunomagnetically selected and aligned cells. *Nat. Biotechnol.* 17, 1210-3 (1999).
2. Galanzha, E. I. et al. In vivo magnetic enrichment and multiplex photoacoustic detection of circulating tumour cells. *Nat. Nanotechnol.* 4, 855-60 (2009).
3. Pantel, K. & Brakenhoff, R. H. Dissecting the metastatic cascade. *Nat. Rev. Cancer* 4, 448-56 (2004).
4. Steeg, P. S. Tumor metastasis: mechanistic insights and clinical challenges. *Nat. Medicine* 12, 895-904 (2006).
5. Pantel, K., Brakenhoff, R. H. & Brandt, B. Detection, clinical relevance and specific biological properties of disseminating tumour cells. *Nat. Rev. Cancer* 8, 329-40 (2008).
6. Nagrath, S. et al. Isolation of rare circulating tumour cells in cancer patients by microchip technology. *Nature* 450, 1235-9 (2007).
7. Adams, A. A et al. Highly efficient circulating tumor cell isolation from whole blood and label-free enumeration using polymer-based microfluidics with an integrated conductivity sensor. *J. Am. Chem. Soc.* 130, 8633-41 (2008).
8. Stott, S. L. et al. Isolation of circulating tumor cells using a microvortex-generating herringbone-chip. *Proc. Natl. Acad. Sci., U.S.A.* 107, 18392-7 (2010).
9. Lien, K.-Y. et al. Rapid isolation and detection of cancer cells by utilizing integrated microfluidic systems. *Lab on Chip* 10, 2875-86 (2010).
10. Saliba, A.-E. et al. Microfluidic sorting and multimodal typing of cancer cells in self-assembled magnetic arrays. *Proc. Natl. Acad. Sci., U.S.A.* 107, 14524-9 (2010).
11. Wang, S. et al. Highly efficient capture of circulating tumor cells by using nanostructured silicon substrates with integrated chaotic micromixers. *Angew. Chem. Intl Ed.* 50, 3084-8 (2011).
12. Hoshino, K. et al. Microchip-based immunomagnetic detection of circulating tumor cells. *Lab on a Chip* 11, 3449-57 (2011).
13. Kang, J. H. et al. A combined micromagnetic-microfluidic device for rapid capture and culture of rare circulating tumor cells. *Lab on a Chip* 12, 2175-81 (2012).
14. Schiro, P. G. et al. Sensitive and high-throughput isolation of rare cells from peripheral blood with ensemble-decision aliquot ranking. *Angew. Chem. Intl Ed.* 51, 4618-22 (2012).
15. Gleghorn, J. P. et al. Capture of circulating tumor cells from whole blood of prostate cancer patients using geometrically enhanced differential immunocapture (GEDI) and a prostate-specific antibody. *Lab on a Chip* 10, 27-9 (2010).
16. Tan, S. J., Yobas, L., Lee, G. Y. H., Ong, C. N. & Lim, C. T. Microdevice for the isolation and enumeration of cancer cells from blood. *Biomedical Microdevices* 11, 883-92 (2009).
17. Zheng, S. et al. 3D microfilter device for viable circulating tumor cell (CTC) enrichment from blood. *Biomedical Microdevices* 13, 203-13 (2011).
18. McCloskey, K. E., Chalmers, J. J. & Zborowski, M. Magnetic Cell Separation: Characterization of Magnetophoretic Mobility to enrich or deplete cells of interest from a heterogeneous. *Anal. Chem.* 75, 6868-6874 (2003).
19. Estes, M. D., Ouyang, B., Ho, S. & Ahn, C. H. Isolation of prostate cancer cell subpopulations of functional interest by use of an on-chip magnetic bead-based cell separator. *J. Micromech. Microeng.* 19, 095015 (2009).
20. Talasaz, A. H. et al. Isolating highly enriched populations of circulating epithelial cells and other rare cells from blood using a magnetic sweeper device. *Proc. Natl. Acad. Sci., U.S.A.* 106, 3970-5 (2009).
21. McCloskey, K. E., Chalmers, J. J. & Zborowski, M. Magnetophoretic mobilities correlate to antibody binding capacities. *Cytometry* 40, 307-15 (2000).
22. Teste, B. et al. Magnetic core shell nanoparticles trapping in a microdevice generating high magnetic gradient. *Lab on a Chip* 11, 833-40 (2011).
23. Baccelli, I. et al. Identification of a population of blood circulating tumor cells from breast cancer patients that initiates metastasis in a xenograft assay *Nat. Biotechnol.* 31, 539-544 (2013).
24. Zhang, L. et al. The Identification and Characterization of Breast Cancer CTCs Competent for Brain Metastasis *Sci. Transl. Med.* 5, 180ra48 (2013).

25. Soleymani, L., Fang, Z., Sargent, E. H. & Kelley, S. O. Programming the detection limits of biosensors through controlled nanostructuring. *Nature Nanotechnol.* 4, 844-8 (2009).
26. Soleymani, L. et al. Hierarchical nanotextured microelectrodes overcome the molecular transport barrier to achieve rapid, direct bacterial detection. *ACS Nano* 5, 3360-6 (2011).
27. Fang, Z. et al. Direct profiling of cancer biomarkers in tumor tissue using a multiplexed nanostructured microelectrode integrated circuit. *ACS Nano* 3, 3207-3213 (2009).
28. Vasilyeva, E. et al. Direct Genetic Analysis of Ten Cancer Cells: Tuning Sensor Structure and Molecular Probe Design for Efficient mRNA Capture. *Angew. Chem. Intl Ed.* 50, 4137-4141 (2011).
29. Lapierre, M. A., O'Keefe, M. M., Taft, B. J. & Kelley, S. O. Electrocatalytic detection of pathogenic DNA sequences and antibiotic resistance markers. *Anal. Chem.* 75, 6327-6333 (2003).
30. Xia, Y. and Whitesides, G. M. Soft Lithography. *Angew. Chem. Intl Ed.* 37, 550-575 (1998).
31. Schneider, C. A., Rasband, W. S., Eliceiri, K. W. NIH Image to ImageJ: 25 years of image analysis. *Nat. Methods* 9, 671-675, (2012).
32. Armstrong, A. J. et al. Breast cancer display both epithelial and mesenchymal markers circulating tumor cells from patients with advanced prostate and breast cancer. *Mol. Cancer Res.* 9, 997-1007 (2011).

The invention claimed is:

1. A device for capture of target particles in a flow, the device comprising:
a flow chamber for receiving a main flow from a flow inlet to a flow outlet;
a plurality of flow rate-reducing structures in the flow chamber and positioned within the main flow, each structure comprising a trapping surface shaped to reduce flow rate in a vicinity of the trapping surface;
wherein the trapping surface of at least one flow rate-reducing structure includes at least one concave surface, the concave surface being concave towards a direction of flow from the inlet to the outlet;
wherein reduced flow rate in the vicinity of the trapping surface is non-zero and has a magnitude lower than that of flow rate in other regions of the flow chamber; and
at least one magnet for generating an attraction force at least in the vicinity of the trapping surface;
wherein the reduced flow rate caused by the flow rate-reducing structure is sufficiently low for the attraction force acting on the target particles to overcome drag force on the target particles, and wherein combination of the reduced flow rate due to the flow rate-reducing structure and the attraction force together promotes capture of particles in the vicinity of the trapping surface.

2. The device of claim 1, wherein there is a plurality of magnets arranged in pairs of opposing polarity, one half of each pair being arranged in a first array and a remaining half of each pair being arranged in a corresponding second array, the flow chamber being positioned between the first and second arrays.

3. The device of claim 1, wherein the at least one magnet is configured to generate a magnetic field gradient over the flow chamber.

4. The device of claim 1, wherein the concave surface of the at least one flow rate-reducing structure is defined by two joined arms defining an angle.

5. The device of claim 1, wherein the flow rate-reducing structures comprise at least one X-shaped structure or cross-shaped structure, wherein the concave surface is defined by two arms of the X-shaped or cross-shaped structure.

6. The device of claim 1, wherein the structures are regularly spaced in the flow chamber.

7. The device of claim 1, wherein the structures are arranged in a plurality of rows substantially perpendicular to the direction of flow, the rows being staggered with respect to each other.

8. The device of claim 1, wherein a plurality of sorting portions are defined in the flow chamber, each sorting portion including a respective plurality of flow rate-reducing structures, wherein each sorting portion promotes capture of respective different target particles experiencing respective different amounts and/or types of attraction force.

9. The device of claim 8 wherein each sorting portion has a different respective reduced flow rate.

10. The device of claim 9 wherein each sorting portion has a different respective average flow rate.

11. The device of claim 8 wherein the sorting portions are defined as discrete compartments in fluid communication with each other.

12. A method for capturing target particles in a sample, the method comprising:
introducing the sample containing the target particles to a device, the target particles being susceptible to a magnetic attraction force;
wherein the device includes:
a flow chamber for receiving a main flow from a flow inlet to a flow outlet;
a plurality of flow rate-reducing structures in the flow chamber and positioned within the main flow, each structure comprising a trapping surface shaped to reduce flow rate in a vicinity of the trapping surface;
wherein the trapping surface of at least one flow rate-reducing structure includes at least one concave surface, the concave surface being concave towards a direction of flow from the inlet to the outlet;
wherein reduced flow rate in the vicinity of the trapping surface is non-zero and has a magnitude lower than that of flow rate in other regions of the flow chamber; and
at least one magnet for generating the attraction force at least in the vicinity of the trapping surface;
wherein the reduced flow rate caused by the flow rate-reducing structure is sufficiently low for the attraction force acting on the target particles to overcome drag force on the target particles, and wherein combination of the reduced flow rate due to the flow rate-reducing structure and the attraction force together promotes capture of particles in the vicinity of the trapping surface;
using the at least one magnet, applying a magnetic field to the flow chamber while flowing the sample through the flow chamber, the magnetic field having a gradient over the flow chamber;
removing the magnetic field; and
eluting the target particles captured in the flow chamber.

13. The method of claim 12, wherein the target particles are labeled with magnetically susceptible nanobeads.

14. The method of claim 12, wherein the target particles include particles having different magnetic properties; and wherein a plurality of sorting portions are defined in the flow chamber of the device, each sorting portion including a respective plurality of flow rate-reducing structures, and each sorting portion promotes capture of respective different particles according to respective different amounts of magnetic attraction force experienced by the respective different particles.

15. The method of claim 14, wherein the particles include magnetically labeled cancer cells in a patient sample.

16. The method of claim 14, wherein the target particles are labeled with magnetically susceptible nanobeads, and wherein each sorting portion promotes capture of respective different particles based on the number of magnetically susceptible nanobeads bonded to the respective different particles.

17. A system for detecting target particles in a sample, the system comprising:
   a capture device including:
      a flow chamber for receiving a main flow from a flow inlet to a flow outlet;
      a plurality of flow rate-reducing structures in the flow chamber and positioned within the main flow, each structure comprising a trapping surface shaped to reduce flow rate in a vicinity of the trapping surface;
      wherein the trapping surface of at least one flow rate-reducing structure includes at least one concave surface, the concave surface being concave towards a direction of flow from the inlet to the outlet;
      wherein reduced flow rate in the vicinity of the trapping surface is non-zero and has a magnitude lower than that of flow rate in other regions of the flow chamber; and
      at least one magnet for generating the attraction force at least in the vicinity of the trapping surface;
      wherein the reduced flow rate caused by the flow rate-reducing structure is sufficiently low for the attraction force acting on the target particles to overcome drag force on the target particles, and wherein combination of the reduced flow rate due to the flow rate-reducing structure and the attraction force together promotes capture of particles in the vicinity of the trapping surface; and
   a detection device comprising sensing electrodes;
   wherein the sensing electrodes generate an electrical signal in response to contact of the target particles with the sensing electrodes.

18. The system of claim 17 wherein the sensing electrodes comprise a sensing surface including an electrical or electrochemical reporter system targeted towards the target particles.

19. The system of claim 18 wherein the sensing electrodes are nanostructured microelectrodes (NMEs) comprising surface groups complementary to the target particles.

20. The system of claim 19 wherein the surface groups complementary to the target particles include antibodies complementary to one or more target proteins.

21. The system of claim 20 wherein the one or more target proteins include one or more cancer-specific proteins.

22. The system of claim 17 wherein the system is provided as a single integrated chip.

23. The system of claim 17 wherein the capture device and the sensing device are in fluid communication with each other, for facilitating transfer of any target particles captured by the capture device, from the capture device to the detection device.

* * * * *